(12) United States Patent
Kato et al.

(10) Patent No.: US 8,103,368 B2
(45) Date of Patent: Jan. 24, 2012

(54) INFORMATION PROCESSING SYSTEM USING NUCLEOTIDE SEQUENCE-RELATED INFORMATION

(75) Inventors: Takamasa Kato, Tokorozawa (JP); Takeo Morimoto, Koshigaya (JP)

(73) Assignee: Hitachi, Ltd., Tokyo (JP)

( * ) Notice: Subject to any disclaimer, the term of this patent is extended or adjusted under 35 U.S.C. 154(b) by 297 days.

(21) Appl. No.: 10/372,923

(22) Filed: Feb. 26, 2003

(65) Prior Publication Data

US 2003/0125883 A1 Jul. 3, 2003

Related U.S. Application Data

(63) Continuation of application No. 10/153,691, filed on May 24, 2002, now Pat. No. 7,912,650.

(30) Foreign Application Priority Data

May 25, 2001 (JP) .................................. 2001-156943

(51) Int. Cl.
| | |
|---|---|
| G06F 17/00 | (2006.01) |
| C12Q 1/68 | (2006.01) |
| G01N 33/48 | (2006.01) |
| G06G 7/58 | (2006.01) |

(52) U.S. Cl. .................. 700/90; 435/6; 702/19; 702/20; 703/11

(58) Field of Classification Search ........................ None
See application file for complete search history.

(56) References Cited

U.S. PATENT DOCUMENTS

| | | | |
|---|---|---|---|
| 5,523,208 | A | 6/1996 | Kohler et al. |
| 5,834,189 | A | 11/1998 | Stevens et al. |
| 5,970,500 | A | 10/1999 | Sabatini et al. |
| 6,572,564 | B2 | 6/2003 | Ito et al. |
| 2002/0010552 | A1 | 1/2002 | Rienhoff, Jr. et al. |
| 2002/0019746 | A1 | 2/2002 | Rienhoff et al. |
| 2002/0133495 | A1 | 9/2002 | Rienhoff et al. |
| 2002/0192647 | A1 | 12/2002 | Smith |
| 2003/0208454 | A1 | 11/2003 | Rienhoff et al. |
| 2004/0091912 | A1 | 5/2004 | Smith |

FOREIGN PATENT DOCUMENTS

| | | |
|---|---|---|
| JP | 10-151125 | 6/1998 |
| JP | 2002-24416 | 1/2002 |
| JP | 2002-183153 | 6/2002 |
| JP | 2002-318858 | 10/2002 |
| WO | WO 01/01218 A2 | 1/2001 |
| WO | WO 01/16857 A2 | 3/2001 |
| WO | WO 01/26029 A2 | 4/2001 |
| WO | WO 01/28415 A1 | 4/2001 |
| WO | WO 01/31551 A1 | 5/2001 |
| WO | WO 01/69430 A1 | 9/2001 |

OTHER PUBLICATIONS

The American Heritage Dictionary of the English Language, definition for "imply," printed on Dec. 9, 2005 from http://www.bartleby.com/61/17/I0061700.html.*
STN International, Biosequence Searching for the USPTO, May 1996.*
Dawson, E, "New Collaborations Make Pharmacogenomics a SNP", Molecular Medicine Today, Jul. 1999, vol. 5, No. 7, p. 280.
S.T. Sherry et al. "dbSNP: the NCBI database of genetic variation," Nucleic Acids Research, vol. 29, No. 1, 2001, pp. 308-311.

* cited by examiner

*Primary Examiner* — Shubo Zhou
(74) *Attorney, Agent, or Firm* — Dickstein Shapiro LLP

(57) ABSTRACT

A system for processing information for providing semantic information and/or information associated with the semantic information useful for each individual organism through effective utilization of differences in nucleotide sequence-related information among individual organisms is constructed. The method for processing information on a nucleotide sequence comprises: (a) receiving request information for an object and/or service; (b) obtaining positional information in accordance with the request information from a memory having positional information representing a position in a nucleotide sequence memorized therein; and (c) obtaining nucleotide sequence-related information corresponding to the positional information obtained in (b) above, and obtaining semantic information implied by the nucleotide sequence-related information and/or information associated with the semantic information.

5 Claims, 30 Drawing Sheets

Fig. 3

| Polymorphism address | ...... | Polymorphism type | Polymorphism pattern | Classification (name of disease) | Annotative information on polymorphism pattern (morbidity rate) | ...... | Level of disclosure (disclosability) |
|---|---|---|---|---|---|---|---|
| 123456 | ...... | SNP | A | hypertension | a | ...... | O |
| 123456 | ...... | SNP | G | hypertension | b | ...... | O |
| 223456 | ...... | SNP | G | large-boowel cancer | (i) | ...... | O |
| 223456 | ...... | SNP | A | large-bowel cancer | (ii) | ...... | O |
| 234567 | ...... | SNP | G | stomach cancer | c | ...... | O |
| 234567 | ...... | SNP | A | stomach cancer | d | ...... | O |
| 334567 | ...... | SNP | A | asthma | (iii) | ...... | O |
| 334567 | ...... | SNP | G | asthma | (iv) | ...... | O |
| 345678 | ...... | SNP | C | diabetes | e | ...... | O |
| 345678 | ...... | SNP | T | diabetes | f | ...... | O |
| 445678 | ...... | SNP | T | lung cancer | (I) | ...... | O |
| 445678 | ...... | SNP | C | lung cancer | (II) | ...... | O |
| 456789 | ...... | SNP | T | pollinosis | g | ...... | O |
| 456789 | ...... | SNP | C | pollinosis | h | ...... | O |
| 456789 | ...... | SNP | T | hypertension | i | ...... | O |
| 456789 | ...... | SNP | C | hypertension | j | ...... | O |
| : | : | microsatellite | 14 times | immedicable disease | — | : | × |
| : | : | microsatellite | 9 times | immedicable disease | — | : | × |
| : | : | deletion | G | : | : | : | O |
| : | : | deletion | deletion | : | : | : | O |

| Gno. | Date of birth |
|---|---|
| 0001 | ++.++.++++ |

II

| Polymorphism address | Polymorphism pattern | Comment |
|---|---|---|
| 000001 | G | ...... |
| 000002 | T | ...... |
| : | : | : |
| 123456 | A | ...... |
| : | : | : |
| 223456 | G | ...... |
| : | : | : |
| 234567 | G | ...... |
| : | : | : |
| 334567 | G | ...... |
| : | : | : |
| 345678 | C | ...... |
| : | : | : |
| 445678 | T | ...... |
| : | : | : |
| 456789 | T | ...... |
| 456790 | G | ...... |
| 456791 | 14 times | ...... |
| 456792 | deletion | ...... |
| : | : | : |

III

| Anamnesis |
|---|
| infantile asthma |
| gout |
| pollinosis |
| gastric ulcer |
| atopy |
| hypertension |
| diabetes |
|  |
|  |
|  |

IV

| Characteristics | Record |
|---|---|
| blood type | type A |
| body height | ...... |
| weight | ...... |
| vision | ...... |
| running ability | ...... |
| psychological test | ...... |
| : | : |
| : | : |
| : | : |
| : | : |
| : | : |

V ......

| (clinical record, etc.) |
|---|
| ...... |
| ...... |
| ...... |
| ...... |
| ...... |
| ...... |
| ...... |
| ...... |
| ...... |
| ...... |
| ...... |

Fig. 10

| Poly-morphism address | Poly-morphism type | Poly-morphism pattern | Major classification | Middle classification (medicament category) | Minor classification | Drug type | Level of disclosure 1 | Level of disclosure 2 |
|---|---|---|---|---|---|---|---|---|
| 123456 | SNP | A | responsiveness to drug | cold remedy | runny nose | a | A (clinical) | B (non-prescription drug) |
| 123456 | SNP | G | responsiveness to drug | cold remedy | runny nose | b | A | B |
| 223456 | SNP | G | responsiveness to drug | antipruritic | pruritus | (i) | A | B |
| 223456 | SNP | A | responsiveness to drug | antipruritic | pruritus | (ii) | A | B |
| 234567 | SNP | G | side-effect | cold remedy | runny nose | c | A | B |
| 234567 | SNP | A | side-effect | cold remedy | runny nose | d | A | B |
| 334567 | SNP | A | side-effect | antipruritic | pruritus | (iii) | A | B |
| 334567 | SNP | G | side-effect | antipruritic | pruritus | (iv) | A | B |
| 345678 | SNP | C | responsiveness to drug | cold remedy | cough | e | A | B |
| 345678 | SNP | T | responsiveness to drug | cold remedy | cough | f | A | B |
| 445678 | SNP | T | responsiveness to drug | gastrointestinal drug | stomachache | (I) | A | B |
| 445678 | SNP | C | responsiveness to drug | gastrointestinal drug | stomachache | (II) | A | B |
| 456789 | SNP | T | side-effect | cold remedy | cough | g | A | B |
| 456789 | SNP | C | side-effect | cold remedy | cough | h | A | B |
| : | microsatellite | 14 times | : | : | : | — | disclosure forbidden | — |
| : | microsatellite | 9 times | : | : | : | — | disclosure forbidden | — |
| : | deletion | G | : | : | : | : | A | — |
| : | deletion | deletion | : | : | : | : | A | — |

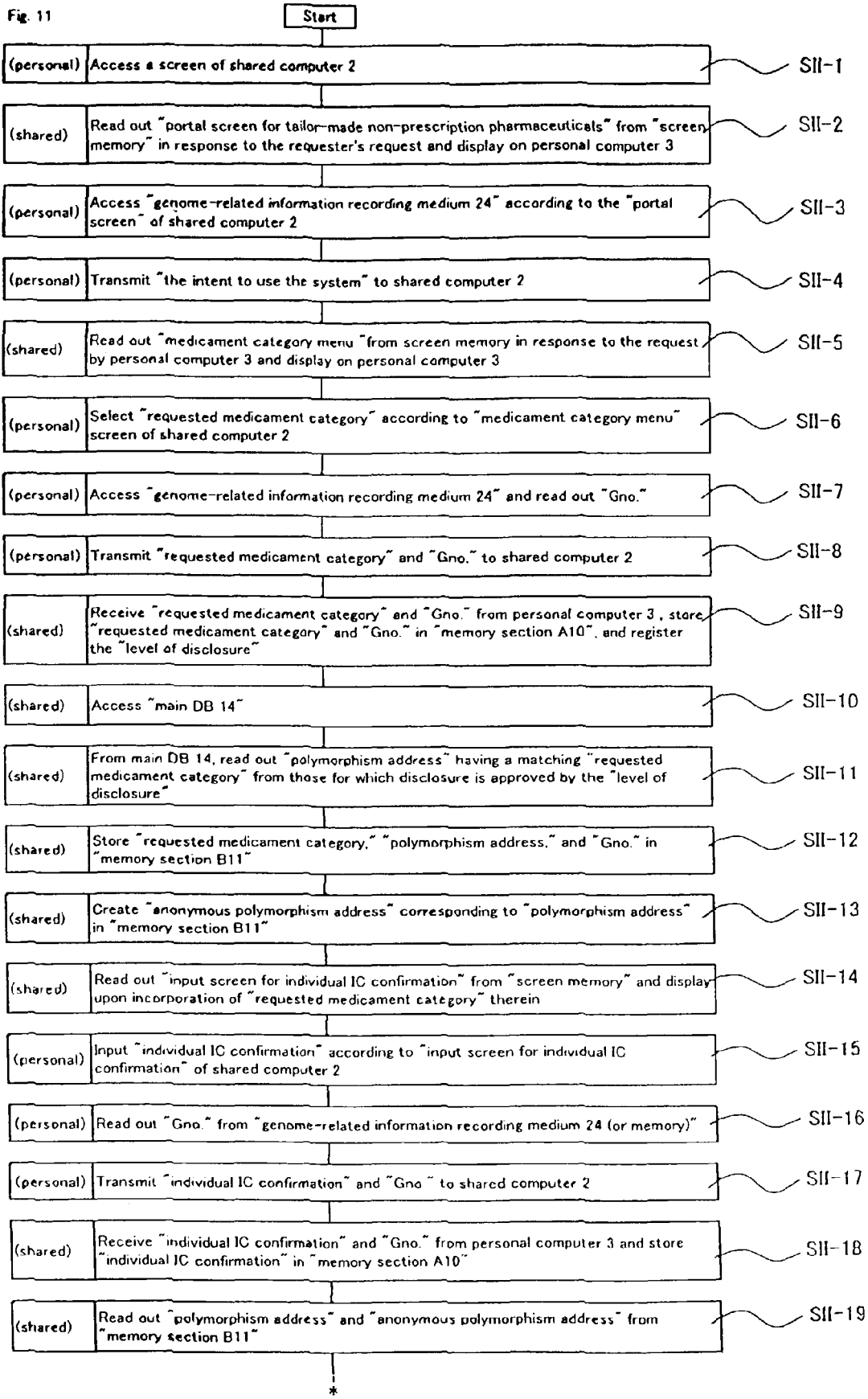

Fig. 16

```
○○ Pharmaceuticals' "My first-aid kit"   About medicine suitable for your diathesis
● "Cold remedy" relatively suitable for your diathesis is as follows:

① Name of medicine:「△△△」「a,c,e,g…」type
    <it works at once and is less likely to cause drowsiness or constipation>
② Benefits: Relief of headache, cough, runny nose, sore throat, chillness, fervescence, aching joint, and
aching muscle
③ Ingredients: ******, ******, ****, ******
④ Dose: Three tablets at a time for those over 15 years old, two tablets at a time for those from 11 to 14
years old, one tablet at a time for those from 5 to 10 years old
⑤ Direction: Preferably take within 30 minutes after meal, three times a day
⑥ Precautions: Refer to "Precautions for use" on the next page      [ Next page        ]
                                                                    [ (Precautions for use) ]
Please click "order screen" below to order the above medicine.

[ Order screen ]                                                    [ Cancel ]
```

Fig. 17

| G no. | Requested medicament | I C | Order information |
|-------|---------------------|-----|-------------------|
| 0001  | cold remedy         | ○   | ……                |
| 0002  | :                   | :   | :                 |
| :     | :                   | :   | :                 |

Fig. 18

| G no. | Requested medicament | Polymorphism address | Anonymous polymorphism address | Polymorphism pattern | Drug type |
|-------|---------------------|---------------------|-------------------------------|---------------------|-----------|
| 0001  | cold remedy         | 123456              | 1                             | A                   | a         |
| 0001  | cold remedy         | 234567              | 2                             | G                   | c         |
| 0001  | cold remedy         | 345678              | 3                             | C                   | e         |
| 0001  | cold remedy         | 456789              | 4                             | T                   | g         |
| :     | :                   | :                   | :                             | :                   | :         |

Fig. 19

| Order No. | Medicament name | Type      | Number of tablets | Number of boxes | …… |
|-----------|-----------------|-----------|-------------------|-----------------|-----|
| 111111    | △△△             | a,c,e,g…  | 100 tablets       | 1 box           | …… |
| :         | :               | :         | :                 | :               | :   |

Fig. 20

| Polymorphism address | Polymorphism type | Polymorphism pattern | Major classification | Middle classification (category of disease) | Minor classification (name of disease) | Annotative information on polymorphism pattern (morbidity rate) (responsiveness, side-effect) | Level of disclosure (disclosability) 1 | Level of disclosure (disclosability) 2 |
|---|---|---|---|---|---|---|---|---|
| 123456 | SNP | A | morbidity rate | hypertension | hypertension | 4 | A (clinical) | B (medical examination) |
| 123456 | SNP | G | morbidity rate | hypertension | hypertension | 2 | A | B |
| 223456 | SNP | G | morbidity rate | cancer | large-bowel cancer | 4 | A | B |
| 223456 | SNP | A | morbidity rate | cancer | large-bowel cancer | 2 | A | B |
| 234567 | SNP | G | morbidity rate | cancer | stomach cancer | Z | A | B |
| 234567 | SNP | A | morbidity rate | cancer | stomach cancer | Z | A | B |
| 334567 | SNP | A | responsiveness to drug | respiratory organs | asthma | a type | A | — |
| 334567 | SNP | G | responsiveness to drug | respiratory organs | asthma | b type | A | — |
| 345678 | SNP | C | responsiveness to drug | diabetes | I type | c type | A | — |
| 345678 | SNP | T | responsiveness to drug | diabetes | I type | d type | A | — |
| 445678 | SNP | T | morbidity rate | digestive organs | gastric ulcer | Z | A | B |
| 445678 | SNP | C | morbidity rate | digestive organs | gastric ulcer | Z | A | B |
| 456789 | SNP | T | morbidity rate | liver | hepatopathy | 1 | A | B |
| 456789 | SNP | C | morbidity rate | liver | hepatopathy | 4 | A | B |
| 500001 | SNP | A | morbidity rate | circulatory organs | arrhythmia | 3 | A | B |
| 500001 | SNP | G | morbidity rate | circulatory organs | arrhythmia | 4 | A | B |
| 500500 | SNP | C | morbidity rate | cancer | stomach cancer | Y | A | B |
| 500500 | SNP | T | morbidity rate | cancer | stomach cancer | Y | A | B |
| 600001 | SNP | A | morbidity rate | respiratory organs | asthma | 1 | A | — |
| 600001 | SNP | G | morbidity rate | respiratory organs | asthma | 4 | A | — |
| 600600 | SNP | T | morbidity rate | cancer | stomach cancer | Y | A | B |
| 600600 | SNP | C | morbidity rate | cancer | stomach cancer | Y | A | B |
| 700001 | SNP | C | drug side-effect | renal diseases | O type | g type | A | — |
| 700001 | SNP | T | drug side-effect | renal diseases | O type | h type | A | — |
| 700700 | SNP | T | morbidity rate | digestive organs | gastric ulcer | Y | A | B |
| 700700 | SNP | C | morbidity rate | digestive organs | gastric ulcer | Y | A | B |
| 800001 | SNP | T | morbidity rate | cancer | lung cancer | 2 | A | B |
| 800001 | SNP | C | morbidity rate | cancer | lung cancer | 4 | A | B |
| 800800 | SNP | T | morbidity rate | lipid | hyperlipemia | 4 | A | B |
| 800800 | SNP | C | morbidity rate | lipid | hyperlipemia | 1 | A | B |
| 900001 | microsatellite | 14 times | morbidity rate | immedicable disease | ○○ disease | 5 | A | — |
| 900001 | microsatellite | 9 times | morbidity rate | immedicable disease | ○○ disease | 1 | A | — |
| 900900 | deletion | G | morbidity rate | leukemia | △ type | 1 | A | — |
| 900900 | deletion | deletion | morbidity rate | leukemia | △ type | 5 | A | — |
| : | : | : | : | : | : | : | : | : |
| : | : | : | : | : | : | : | : | : |

Fig. 21

| Polymorphism address Z | Pattern Z | Polymorphism address Y | Pattern Y | Morbidity rate |
|---|---|---|---|---|
| 234567 | G | 500500, 600600 | C, T | 2 |
| 234567 | G | 500500, 600600 | C, C | 2 |
| 234567 | G | 500500, 600600 | T, T | 4 |
| 234567 | G | 500500, 600600 | T, C | 2 |
| 234567 | A | 500500, 600600 | C, T | 2 |
| 234567 | A | 500500, 600600 | C, C | 2 |
| 234567 | A | 500500, 600600 | T, T | 1 |
| 234567 | A | 500500, 600600 | T, C | 2 |
| 445678 | T | 700700 | T | 4 |
| 445678 | T | 700700 | C | 2 |
| 445678 | C | 700700 | T | 2 |
| 445678 | C | 700700 | C | 4 |
| : | : | : | : | : |

| Gno. | Date of birth |
|---|---|
| 0001 | ** ** **** |

II

| Polymorphism address | Polymorphism pattern | Comment |
|---|---|---|
| 000001 | G | ...... |
| 000002 | T | ...... |
| : | : | : |
| 123456 | A | ...... |
| : | : | : |
| 223456 | G | ...... |
| : | : | : |
| 234567 | G | ...... |
| : | : | : |
| 334567 | G | ...... |
| : | : | : |
| 345678 | C | ...... |
| : | : | : |
| 445678 | T | ...... |
| : | : | : |
| 456789 | T | ...... |
| : | : | : |
| 50001 | A | ...... |
| : | : | : |
| 500500 | T | ...... |
| : | : | : |
| 600001 | A | ...... |
| : | : | : |
| 600600 | T | ...... |
| : | : | : |
| 700001 | C | ...... |
| : | : | : |
| 700700 | T | ...... |
| : | : | : |
| 800001 | T | ...... |
| : | : | : |
| 800800 | C | ...... |
| : | : | : |
| 900001 | 14 times | ...... |
| 900900 | G | ...... |
| : | : | : |

III

| Anamnesis |
|---|
| infantile asthma |
| gout |
| pollinosis |
| gastric ulcer |
| atopy |
| hypertension |
| diabetes |

IV

| Characteristics | Record |
|---|---|
| blood type | type A |
| body height | ...... |
| weight | ...... |
| vision | ...... |
| running ability | ...... |
| psychological test | ...... |
| : | : |

V ......

| (clinical record, etc.) |
|---|
| ...... |
| ...... |
| ...... |
| ...... |
| ...... |
| ...... |
| ...... |
| ...... |

Fig. 27

| Major classification | Middle classification (category of disease) | Minor classification (name of disease) | Examination method | Examination items | Examinee's preparation | Inquiry items | ... |
|---|---|---|---|---|---|---|---|
| basic | infectious disease | infectious disease | blood sampling (hematology) | white blood cell count | — | — | ... |
| basic | anemia | anemia | blood sampling (hematology) | red blood cell count | — | ****** | ... |
| basic | anemia | anemia | blood sampling (hematology) | hemoglobin content | — | ****** | ... |
| : | : | : | : | : | : | : | : |
| basic | liver function | hepatopathy | blood sampling (biochemistry) | total protein level | — | ****** | ... |
| basic | liver function | hepatopathy | blood sampling (biochemistry) | total bilirubin level | — | ****** | ... |
| : | : | : | : | : | : | : | : |
| basic | sugar | diabetes | urinalysis (paper test) | urinary sugar | ****** | ****** | ... |
| : | : | : | : | : | : | : | : |
| basic | hypertension | hypertension | hemo-dynamometer | blood pressure level | ****** | ****** | ... |
| morbidity rate | hypertension | hypertension | hemo-dynamometer | blood pressure level | — | ****** | ... |
| morbidity rate | cancer | large-bowel cancer | stool examination (protein chip) | ○○ protein | collection of stool | ****** | ... |
| morbidity rate | cancer | stomach cancer | blood sampling (protein chip) | ×× protein | — | ****** | ... |
| morbidity rate | cancer | lung cancer | blood sampling (protein chip) | △△ protein | — | ****** | ... |
| : | : | : | : | : | : | : | : |
| morbidity rate | liver | hepatopathy | blood sampling (biochemistry) | ZTT | — | ****** | ... |
| morbidity rate | liver | hepatopathy | blood sampling (biochemistry) | LDH | — | ****** | ... |
| : | : | : | : | : | : | : | : |
| morbidity rate | circulatory organs | arrhythmia | electrocardiogram (rest) | myocardinal action potential | — | ****** | ... |
| : | : | : | : | : | : | : | : |
| morbidity rate | lipid | hyperlipemia | blood sampling (biochemistry) | neutral fat | — | ****** | ... |
| : | : | : | : | : | : | : | : |

<OO Medical Care Center>
About "informed consent" in "My check-up ! Entrusted check-up course"
~ Please let us confirm your consent to the following. ~

① In order to perform "My check-up! Entrusted check-up course", you will first provide us, OO Medical Care Center, with only a part of your genomic information with which your "susceptibility" to various cancers, liver disfunction, heart disease, brain disease, hypertension, diabetes ... can be distinguished from your genomic information.

② The genomic information you provide is made anonymous and then checked with the "causal relation between polymorphism information and morbidity rate" prepared by "****" to determine your susceptibility to the diseases in ① above.

Examination items associated with diseases with a "susceptibility" exceeding a given standard※ are selected as examination items peculiar to you and are examined in addition to general examination items, and reflected in to guidance for better living.

※ Basic calculation of "susceptibility" and details on setting of standard are displayed by following screens ③ Regarding diseases associated with examination items not selected in "Entrusted check-up course", susceptibility is merely relatively low, and it does not indicate that there is no morbidity rate.

Also, you do not necessarily suffer from the disease selected, and instead, you may be able to prevent it by awareness and life style improvements.

● Please click "OK" below upon confirmation and consent to the above.

| OK | | Cancel |

Fig. 29

| Gno. | Middle classification (category of disease) | Minor classification (name of disease) | Polymorphism address | Anonymous polymorphism address | Polymorphism pattern | Morbidity rate |
|---|---|---|---|---|---|---|
| 0001 | hypertension | hypertension | 123456 | 1 | A | 4 |
| 0001 | cancer | large-bowel cancer | 223456 | 2 | G | 4 |
| 0001 | cancer | stomach cancer | 234567 | 3 | G | 4 |
| 0001 | cancer | stomach cancer | 500500 | 4 | T | - |
| 0001 | cancer | stomach cancer | 600600 | 5 | T | - |
| 0001 | cancer | lung cancer | 800001 | 6 | T | 2 |
| 0001 | digestive organs | gastric ulcer | 445678 | 7 | T | 4 |
| 0001 | digestive organs | gastric ulcer | 700700 | 8 | T | - |
| 0001 | liver | hepatopathy | 456789 | 9 | T | 1 |
| 0001 | circulatory organs | arrhythmia | 500001 | 10 | A | 3 |
| 0001 | lipid | hyperlipemia | 800800 | 11 | C | 1 |
| : | : | : | : | : | : | : |

Fig. 30

| Gno. | Name of check-up | IC confirmation |
|---|---|---|
| 0001 | entrusted | O |
| 0002 | . | : |
| : | : | : |

Fig. 31

| Gno. | Chart No. | Name | Sex | Date of birth | Date of examination | Medical institution admitting examinees | |
|---|---|---|---|---|---|---|---|
| | | | | | | | |

| Category of examination | Examination method | Examination purpose | Mor-bidity | No. | Examination items | Category | Inquiry items | Preparation | Inquiry result/remarks |
|---|---|---|---|---|---|---|---|---|---|
| 1. Blood sampling | hematology | infectious disease | | 1 | white blood cell count | basic | ****** | ****** | |
| | | anemia | | 2 | red blood cell count | basic | ****** | ****** | |
| | | | | 3 | hemoglobin content | basic | ****** | ****** | |
| | | | | 4 | hematocrit value | basic | ****** | ****** | |
| | | coagulation system | | 5 | platelet count | basic | ****** | ****** | |
| | biochemistry | hepatopathy | | 6 | total protein level | basic | ****** | ****** | |
| | | | | 7 | total bilirubin level | basic | ****** | ****** | |
| | | | | 8 | GOT | basic | ****** | ****** | |
| | | | | 9 | GPT | basic | ****** | ****** | |
| | | | | 10 | ALP | basic | ****** | ****** | |
| | | | | 11 | γ−GTP | basic | ****** | ****** | |
| | | | | 12 | cholinesterase | basic | ****** | ****** | |
| | | hyperlipemia | | 13 | neutral fat | basic | ****** | ****** | |
| | | | | 14 | total cholesterol | basic | ****** | ****** | |
| | | | | 15 | HDL cholesterol | basic | ****** | ****** | |
| | | | | 16 | LDL cholesterol | basic | ****** | ****** | |
| | | nephropathy | | 17 | urea nitrogen | basic | ****** | ****** | |
| | | | | 18 | creatinine count | basic | ****** | ****** | |
| | | diabetes | | 19 | blood glucose level | basic | ****** | ****** | |
| | | electrolyte | | 20 | serum sodium (Na) | basic | ****** | ****** | |
| | | | | 21 | serum potassium (K) | basic | ****** | ****** | |
| | | | | 22 | serum chlor (Cl) | basic | ****** | ****** | |
| | protein chip | stomach cancer | 4 | 23 | ×× protein | specific | ****** | ****** | |
| 2. Urinalysis | paper test | diabetes | | 24 | urinary sugar | basic | ****** | ****** | |
| | | nephropathy | | 25 | urine protein | basic | ****** | ****** | |
| | | | | 26 | urine occult blood | basic | ****** | ****** | |
| | | hepatopathy | | 27 | urobilinogen | basic | ****** | ****** | |
| 3. Stool examination | orthotolidine | digestive organs | 4 | 28 | stool occult blood | basic | ****** | ****** | |
| | protein chip | large-bowel cancer | 4 | 29 | OO protein | specific | ****** | ****** | |
| 4. Electro-cardiogram | rest | arrhythmia | | 30 | myocardinal action potential | basic | ****** | ****** | |
| 5. Blood pressure | hemo-dynamometer | hypertension | 4 | 31 | blood pressure level | basic | ****** | ****** | |
| 6. Chest X-ray | X-ray | lung disease | | 32 | lung X-ray image | basic | ****** | ****** | |
| 7. Eyeground | retinal camera | diabetes, arteriosclerosis | | 33 | retinal camera image | basic | ****** | ****** | |
| 8. Visual acuity/audibility | direct examination | visual acuity/audibility | | 34 | direct visual acuity/audibility test | basic | ****** | ****** | |
| 9. Measurement | direct measurement | obesity index | | 35 | body height, weight | basic | ****** | ****** | |

Fig. 32

| Classification | Polymorphism address | | Polymorphism pattern | | Individual property type | Compatible type | Level of disclosure (disclosability) |
|---|---|---|---|---|---|---|---|
| | 1 | 2 | 1 | 2 | | | |
| Given property | 1000 | 2000 | A | C | a | b | A |
| Given property | 1000 | 2000 | G | T | a | b | A |
| Given property | 1000 | 2000 | G | C | b | a | A |
| Given property | 1000 | 2000 | A | T | b | a | A |
| Other property | 3000 | 4000 | G | C | (i) | (i) | B |
| Other property | 3000 | 4000 | deletion | T | (ii) | (ii) | B |
| : | : | : | : | : | : | : | : |

| Gno. | Date of birth |
|---|---|
| 0001 | ..**** |

II

| Polymorphism address | Polymorphism pattern | Comment |
|---|---|---|
| 0001 | G | ...... |
| 0002 | T | ...... |
| : | : | : |
| 1000 | A | ...... |
| : | : | : |
| 2000 | C | ...... |
| : | : | : |
| 3000 | deletion | ...... |
| : | : | : |
| 4000 | T | ...... |
| : | : | : |

III

| Anamnesis |
|---|
| infantile asthma |
| gout |
| pollinosis |
| gastric ulcer |
| atopy |
| hypertension |
| diabetes |
|  |
|  |
|  |
|  |

IV

| Characteristics | Record |
|---|---|
| blood type | type A |
| body height | ...... |
| weight | ...... |
| vision | ...... |
| running ability | ...... |
| psychological test | ...... |
| : | : |
| : | : |
| : | : |
| : | : |

V ......

| (clinical record, etc.) |
|---|
| ...... |
| ...... |
| ...... |
| ...... |
| ...... |
| ...... |
| ...... |
| ...... |
| ...... |
| ...... |
| ...... |

Fig. 35

| Gno. | Classification | Polymorphism address | | Polymorphism pattern | | ... |
|---|---|---|---|---|---|---|
| | | 1 | 2 | 1 | 2 | |
| 0001 | Given property | 1000 | 2000 | A | C | ... |
| 0002 | Given property | 1000 | 2000 | G | T | ... |
| 0003 | Given property | 1000 | 2000 | G | C | ... |
| 0004 | Given property | 1000 | 2000 | A | T | ... |
| : | : | : | : | : | : | : |

US 8,103,368 B2

INFORMATION PROCESSING SYSTEM USING NUCLEOTIDE SEQUENCE-RELATED INFORMATION

This application is a continuation of application Ser. No. 10/153,691, filed on May 24, 2002, now U.S. Pat. No. 7,912,650, which is incorporated by reference herein.

FIELD OF THE INVENTION

The present invention relates to an information processing system that provides information through a communication network.

BACKGROUND TECHNIQUE

Currently, genomic nucleotide sequences of various organisms including humans are being rapidly determined and information on genomic nucleotide sequences is being accumulated in various databases. For example, currently in progress is the construction of a system which will enable various research institutes and researchers to utilize information on genomic nucleotide sequences accumulated in databases through an information network such as the Internet.

At the same time, research for the purpose of genomic drug discovery and analysis of genetic information and the like have been actively conducted using nucleotide sequences contained in such information on genomic nucleotide sequences, and differences in nucleotide sequences among individual organisms represented by the single nucleotide polymorphism are attracting attention. In general, differences in nucleotide sequences among individual organisms refer to a polymorphism defined by existence of a predetermined nucleotide difference at a frequency of 1% or more in an individual species and a variation defined by a predetermined nucleotide difference of less than 1% in an individual species. In particular, known polymorphisms are SNP (single nucleotide polymorphism), in which there is one nucleotide difference among individual organisms; an insertion/deletion polymorphism, in which one to several tens of nucleotides (sometimes several thousands of nucleotides) have been deleted or inserted; VNTR (variable number of tandem repeat), in which the number of repetitions of a sequence comprising two to several tens of nucleotides as one unit varies; and a microsatellite polymorphism (a repetition sequence having about two to four nucleotides).

Such polymorphisms sometimes affect, for example, differences in amino acid sequences of proteins among individual organisms or differences in expression efficiency concerning predetermined genes among individual organisms. Such influences cause, for example, differences in the morbidity rate of predetermined diseases among individual organisms or differences in sensitiveness to predetermined medicaments among individual organisms.

A system, however, which provides semantic information useful for each organism among a plurality of individual organisms through effective utilization of differences in nucleotide sequence-related information, such as a polymorphism, is not yet constructed.

Under the above circumstances, the present invention is directed to construction of a system for processing information for providing semantic information and/or information associated with the semantic information useful for each individual organism through effective utilization of differences in nucleotide sequence-related information among individual organisms.

SUMMARY OF THE INVENTION

The present invention, whereby the above objects have been accomplished, includes the following features:

1. A method for processing information on a nucleotide sequence comprising steps of:
   (a) receiving request information for an object and/or service;
   (b) obtaining positional information in accordance with the request information from a memory having positional information representing a position in a nucleotide sequence memorized therein; and
   (c) obtaining, from among nucleotide sequence-related information associated with positional information, nucleotide sequence-related information corresponding to the positional information obtained in step (b) above, and obtaining semantic information implied by the nucleotide sequence-related information and/or information associated with the semantic information.

2. The method for processing information on a nucleotide sequence according to (1), the semantic information and/or the information associated with the semantic information obtained in step (c) above is transmitted to an information processor which provided the request information in step (a) above and/or a user of the semantic information and/or the information associated with the semantic information.

3. The method for processing information on a nucleotide sequence according to (1), at least step (d) transmitting the positional information obtained in step (b) above is further comprised and, in step (c) above, from among nucleotide sequence-related information associated with positional information, nucleotide sequence-related information corresponding to the positional information transmitted in step (d) above is received, and semantic information implied by the received nucleotide sequence-related information and/or information associated with the semantic information is then obtained.

4. The method for processing information on a nucleotide sequence according to (3), in step (d) above, secondary positional information corresponding to the positional information obtained in step (b) above is set and the positional information obtained in step (b) above is transmitted in association with the secondary positional information, and in step (c) above, the nucleotide sequence-related information is received in association with the secondary positional information, and semantic information implied by the nucleotide sequence-related information associated with the positional information through the secondary positional information and/or information associated with the semantic information is then obtained.

5. The method for processing information on a nucleotide sequence according to (3), from a memory having memorized therein a plurality of pieces of positional information, a plurality of pieces of nucleotide sequence-related information associated with each of the plurality of pieces of positional information, and semantic information implied by each of the plurality of pieces of nucleotide sequence-related information, respectively, semantic information associated with nucleotide sequence-related information corresponding to the positional information transmitted in step (d) above is extracted to obtain semantic information implied by the nucleotide sequence-related information received in step (c) above.

6. The method for processing information on a nucleotide sequence according to (1), in step (c) above, a plurality of pieces of nucleotide sequence-related information corresponding to the positional information obtained in step (b)

above is obtained, and semantic information implied by each of the plurality of pieces of nucleotide sequence-related information and/or information associated with the semantic information is obtained.

7. The method for processing information on a nucleotide sequence according to (1), at least step (d) receiving nucleotide sequence-related information associated with positional information is further comprised and, in step (c) above, using the nucleotide sequence-related information received in step (d) above, nucleotide sequence-related information corresponding to the positional information obtained in step (b) above is obtained.

8. The method for processing information on a nucleotide sequence according to (7), from a memory having memorized therein a plurality of pieces of positional information, a plurality of pieces of nucleotide sequence-related information associated with each of the plurality of pieces of positional information, and semantic information implied by each of the plurality of pieces of nucleotide sequence-related information, respectively, semantic information associated with nucleotide sequence-related information corresponding to the nucleotide sequence-related information received in step (d) above is extracted to obtain semantic information implied by the nucleotide sequence-related information obtained in step (c) above.

9. The method for processing information on a nucleotide sequence according to (1), whether transmission of the semantic information and/or the information associated with the semantic information is approved or not is determined.

10. The method for processing information on a nucleotide sequence according to (1), in step (b) above, a plurality of pieces of positional information in accordance with the request information is obtained, and in step (c) above, from among nucleotide sequence-related information associated with positional information, nucleotide sequence-related information corresponding to each of the plurality of pieces of positional information obtained in step (b) above is obtained, and semantic information implied by a combination of the nucleotide sequence-related information and/or information associated with the semantic information is obtained.

11. The method for processing information on a nucleotide sequence according to (1) comprising steps of: asking the provider of the request information for consent to the provision of nucleotide sequence-related information; and/or asking the provider of the request information for consent regarding the content of semantic information and/or information associated with the semantic information.

12. The method for processing information on a nucleotide sequence according to (1), the semantic information comprises at least one piece of information selected from the group consisting of information on medical examination items, information on a morbidity rate of a disease, information on the production of objects, information on the selection of types of objects, and information on compatibility with other individual organisms.

13. The method for processing information on a nucleotide sequence according to (1), additional information on the provider of the request information is obtained and the additional information is associated with the semantic information and/or the information associated with the semantic information obtained in step (c) above.

14. A method for processing information on a nucleotide sequence comprising steps of:
(a) receiving request information for an object and/or service;
(b) obtaining positional information in accordance with the request information from a memory having positional information representing a position in a nucleotide sequence memorized therein;
(c) transmitting at least the positional information obtained in step (b) above; and
(d) receiving nucleotide sequence-related information corresponding to the positional information transmitted in step (c) above.

15. The method for processing information on a nucleotide sequence according to (14) comprising steps of: asking the provider of the request information for consent to the provision of nucleotide sequence-related information; and/or asking the provider of the request information for consent regarding the content of semantic information implied by the nucleotide sequence-related information which is received in step (d) above and/or information associated with the semantic information.

16. The method for processing information on a nucleotide sequence according to (14), in step (c) above, secondary positional information corresponding to the positional information obtained in step (b) above is set and the positional information obtained in step (b) above is transmitted in association with the secondary positional information, and in step (d) above, the nucleotide sequence-related information is received in association with the secondary positional information.

17. A method for processing information on a nucleotide sequence comprising steps of:
(a) receiving nucleotide sequence-related information associated with positional information, in accordance with request information for an object and/or service, representing a position in a nucleotide sequence; and
(b) obtaining semantic information implied by the nucleotide sequence-related information received in step (a) above and/or information associated with the semantic information.

18. The method for processing information on a nucleotide sequence according to (17), in step (b) above, from a memory having memorized therein a plurality of pieces of positional information, a plurality of pieces of nucleotide sequence-related information associated with each of the plurality of pieces of positional information, and semantic information implied by each of the plurality of pieces of nucleotide sequence-related information, respectively, semantic information associated with nucleotide sequence-related information corresponding to the nucleotide sequence-related information which is received in step (a) above is extracted to obtain semantic information implied by the nucleotide sequence-related information.

19. The method for processing information on a nucleotide sequence according to (17), the semantic information and/or the information associated with the semantic information obtained in step (b) above is transmitted to at least one of: an information processor which provided the nucleotide sequence-related information in step (a) above; an information processor which provided the request information; and a user of the semantic information and/or the information associated with the semantic information.

20. The method for processing information on a nucleotide sequence according to (17), whether transmission of the semantic information and/or the information associated with the semantic information is approved or not is determined.

21. The method for processing information on a nucleotide sequence according to (17), in step (a) above, nucleotide sequence-related information associated with each of a plurality of pieces of positional information in accordance with request information is received and, in step (b) above, semantic information implied by a combination of the nucleotide sequence-related information and/or information associated with the semantic information is obtained.

22. A method for processing information on a nucleotide sequence comprising steps of:

(a) obtaining semantic information on a predetermined individual organism that is implied by nucleotide sequence-related information associated with positional information, in accordance with a request for an object and/or service, representing a position in a nucleotide sequence; and (b) searching semantic information on an other individual organism(s) from a memory having semantic information implied by nucleotide sequence-related information on the other individual organism(s) memorized therein, and judging the compatibility between the semantic information on the predetermined individual organism and the semantic information on the other individual organism(s).

23. The method for processing information on a nucleotide sequence according to (22), information on the judgment obtained in step (b) above is transmitted to the requester of the object and/or the service and/or a user of the information on the judgment.

24. A method for processing information on a nucleotide sequence comprising steps of:

(a) obtaining semantic information that is implied by nucleotide sequence-related information associated with positional information, in accordance with a request for an object and/or service, representing a position in a nucleotide sequence and that interrelates information on a predetermined individual organism and information on an other individual organism;

(b) extracting nucleotide sequence-related information associated with positional information, with which semantic information containing information on a predetermined individual organism which is recognized as in conformity with information on an other individual organism contained in the semantic information obtained in step (a) above is associated; and (c) from a memory having memorized therein information for discriminating an individual organism in association with nucleotide sequence-related information associated with positional information, extracting information for discriminating an individual organism associated with the nucleotide sequence-related information extracted in step (b) above.

25. The method for processing information on a nucleotide sequence according to (24), the result of extraction obtained in step (c) above is transmitted to the requester of the object and/or the service and/or a user of the result of extraction.

26. A method for processing information on a nucleotide sequence comprising steps of:

(a) receiving positional information representing a position in a nucleotide sequence in accordance with a request for an object and/or service;

(b) obtaining nucleotide sequence-related information associated with positional information corresponding to the positional information received in step (a) above; and (c) transmitting the nucleotide sequence-related information obtained in step (b) above.

27. The method for processing information on a nucleotide sequence according to (26), in step (b) above, nucleotide sequence-related information is obtained from a recording medium.

28. The method for processing information on a nucleotide sequence according to (26), in step (c) above, the nucleotide sequence-related information is transmitted to an information processor which provided the positional information.

29. The method for processing information on a nucleotide sequence according to (26), in step (a) above, the positional information as well as secondary positional information which is set according to the positional information are received, and in step (c) above, the nucleotide sequence-related information obtained in step (b) above is transmitted in association with the secondary positional information.

30. The method for processing information on a nucleotide sequence according to (26) comprising, prior to step (a) above, step (d) transmitting the request information for the object and/or the service and, after step (c) above, step (e) receiving semantic information implied by the nucleotide sequence-related information transmitted in step (c) above and/or information associated with the semantic information.

31. A method for processing information on a nucleotide sequence comprising steps of:

(a) receiving positional information, in accordance with a request for an object and/or service, representing a position in a nucleotide sequence; a plurality of pieces of nucleotide sequence-related information associated with the positional information; and semantic information and/or information associated with the semantic information, which is associated with each of the plurality of pieces of nucleotide sequence-related information respectively; and (b) from among a plurality of combinations of the positional information and the nucleotide sequence-related information received in step (a) above, selecting a combination corresponding to a combination of positional information and nucleotide sequence-related information possessed by the requester, and extracting semantic information and/or information associated with the semantic information, which is associated with nucleotide sequence-related information contained in the selected combination.

32. A method for processing information on a nucleotide sequence comprising steps of:

(a) transmitting positional information representing a position in a nucleotide sequence, and nucleotide sequence-related information associated with the positional information;

(b) transmitting request information for an object and/or service; and (c) receiving semantic information implied by nucleotide sequence-related information corresponding to positional information in accordance with the request information and/or information associated with the semantic information.

33. A program for processing information on a nucleotide sequence which allows a computer to execute processes including:

(a) receiving request information for an object and/or service through a transmitter/receiver;

(b) from a memory having positional information representing a position in a nucleotide sequence memorized therein, obtaining through a controller positional information in accordance with the request information; and (c) from among nucleotide sequence-related information associated with positional information, obtaining through a controller nucleotide sequence-related information corresponding to the positional information obtained in process (b) above, and obtaining through a controller semantic information implied by the nucleotide sequence-related information and/or information associated with the semantic information.

34. The program for processing information on a nucleotide sequence according to (33), the semantic information and/or the information associated with the semantic information obtained in process (c) above is transmitted through a transmitter/receiver to an information processor which provided the request information in process (a) above and/or a user of the semantic information and/or the information associated with the semantic information.

35. The program for processing information on a nucleotide sequence according to (33), at least process (d) transmitting, through a transmitter/receiver, the positional information obtained in process (b) above is further comprised, and in process (c) above, from among nucleotide sequence-related information associated with positional information, nucleotide sequence-related information corresponding to the positional information transmitted in process (d) above is received, and semantic information implied by the received nucleotide sequence-related information and/or information associated with the semantic information is then obtained.

36. The program for processing information on a nucleotide sequence according to (35), in process (d) above, secondary positional information corresponding to the positional information obtained in process (b) above is set and the positional information obtained in process (b) above is transmitted in association with the secondary positional information, and in process (c) above, the nucleotide sequence-related information is received in association with the secondary positional information, and semantic information implied by the nucleotide sequence-related information associated with the positional information through the secondary positional information and/or information associated with the semantic information is then obtained.

37. The program for processing information on a nucleotide sequence according to (35), from a memory having memorized therein a plurality of pieces of positional information, a plurality of pieces of nucleotide sequence-related information associated with each of the plurality of pieces of positional information, and semantic information implied by each of the plurality of pieces of nucleotide sequence-related information, respectively, semantic information associated with nucleotide sequence-related information corresponding to the positional information transmitted in process (d) above is extracted to obtain semantic information implied by the nucleotide sequence-related information received in process (c) above.

38. The program for processing information on a nucleotide sequence according to (33), in process (c) above, a plurality of pieces of nucleotide sequence-related information corresponding to the positional information obtained in process (b) above is obtained, and semantic information implied by each of the plurality of pieces of nucleotide sequence-related information and/or information associated with the semantic information is obtained.

39. The program for processing information on a nucleotide sequence according to (33), at least process (d) receiving through a transmitter/receiver nucleotide sequence-related information associated with positional information is further comprised, and in process (c) above, using the nucleotide sequence-related information received in process (d) above, nucleotide sequence-related information corresponding to the positional information obtained in process (b) above is obtained.

40. The program for processing information on a nucleotide sequence according to (39), from a memory having memorized therein a plurality of pieces of positional information, a plurality of pieces of nucleotide sequence-related information associated with each of the plurality of pieces of positional information, and semantic information implied by each of the plurality of pieces of nucleotide sequence-related information, respectively, semantic information associated with nucleotide sequence-related information corresponding to the nucleotide sequence-related information received in process (d) above is extracted to obtain semantic information implied by the nucleotide sequence-related information obtained in process (c) above.

41. The program for processing information on a nucleotide sequence according to (33), whether transmission of the semantic information and/or the information associated with the semantic information is approved or not is determined through a controller.

42. The program for processing information on a nucleotide sequence according to (33), in process (b) above, a plurality of pieces of positional information in accordance with the request information is obtained and, in process (c) above, from among nucleotide sequence-related information associated with positional information, nucleotide sequence-related information corresponding to each of the plurality of pieces of positional information obtained in process (b) above is obtained, and semantic information implied by a combination of the nucleotide sequence-related information and/or information associated with the semantic information is obtained.

43. A program for processing information on a nucleotide sequence which allows a computer to execute processes including:
(a) receiving request information for an object and/or service through a transmitter/receiver;
(b) obtaining through a controller positional information in accordance with the request information from a memory having positional information representing a position in a nucleotide sequence memorized therein;
(c) transmitting through a transmitter/receiver, at least, the positional information obtained in process (b) above; and
(d) receiving through a transmitter/receiver nucleotide sequence-related information corresponding to the positional information transmitted in process (c) above.

44. The program for processing information on a nucleotide sequence according to (43), in process (c) above, secondary positional information corresponding to the positional information obtained in process (b) above is set and the positional information obtained in process (b) above is transmitted in association with the secondary positional information, and in process (d) above, the nucleotide sequence-related information is received in association with the secondary positional information.

45. A program for processing information on a nucleotide sequence which allows a computer to execute processes including:
(a) receiving through a transmitter/receiver nucleotide sequence-related information associated with positional information, in accordance with request information for an object and/or service, representing a position in a nucleotide sequence; and
(b) obtaining through a controller semantic information implied by the nucleotide sequence-related information received in process (a) above and/or information associated with the semantic information.

46. The program for processing information on a nucleotide sequence according to (45), in process (b) above, from a memory having memorized therein a plurality of pieces of positional information, a plurality of pieces of nucleotide sequence-related information associated with each of the plurality of pieces of positional information, and semantic information implied by each of the plurality of pieces of nucleotide sequence-related information, respectively, semantic information associated with nucleotide sequence-related information corresponding to the nucleotide sequence-related information which is received in step (a) above is extracted to obtain semantic information implied by the nucleotide sequence-related information.

47. The program for processing information on a nucleotide sequence according to (45), the semantic information and/or the information associated with the semantic information obtained in process (b) above is transmitted through a transmitter/receiver to at least one of: an information processor which provided the nucleotide sequence-related information in process (a) above; an information processor which provided the request information; and a user of the semantic information and/or the information associated with the semantic information.

48. The program for processing information on a nucleotide sequence according to (45), whether transmission of the semantic information and/or the information associated with the semantic information is approved or not is determined through a controller.

49. The program for processing information on a nucleotide sequence according to (45), in process (a) above, nucleotide sequence-related information associated with each of a plurality of pieces of positional information in accordance with request information is received and, in process (b) above, semantic information implied by a combination of the nucleotide sequence-related information and/or information associated with the semantic information is obtained.

50. A program for processing information on a nucleotide sequence which allows a computer to execute processes including:
(a) obtaining through a controller semantic information on a predetermined individual organism that is implied by nucleotide sequence-related information associated with positional information, in accordance with a request for an object and/or service, representing a position in a nucleotide sequence; and
(b) searching semantic information on an other individual organism(s) from a memory having semantic information implied by nucleotide sequence-related information on the other individual organism(s) memorized therein, and judging the compatibility between the semantic information on the predetermined individual organism and the semantic information on the other individual organism(s) through a controller.

51. The program for processing information on a nucleotide sequence according to (50), information on the judgment obtained in process (b) above is transmitted through a transmitter/receiver to the requester of the object and/or the service and/or a user of the information on the judgment.

52. A program for processing information on a nucleotide sequence which allows a computer to execute processes including:
(a) obtaining through a controller semantic information that is implied by nucleotide sequence-related information associated with positional information, in accordance with a request for an object and/or service, representing a position in a nucleotide sequence, and that interrelates information on a predetermined individual organism and information on an other individual organism;
(b) extracting through a controller nucleotide sequence-related information associated with positional information, with which semantic information containing information on a predetermined individual organism which is recognized as in conformity with information on an other individual organism contained in the semantic information obtained in process (a) above is associated; and
(c) from a memory having memorized therein information for discriminating an individual organism in association with nucleotide sequence-related information associated with positional information extracting through a controller information for discriminating an individual organism associated with the nucleotide sequence-related information extracted in process (b) above.

53. The program for processing information on a nucleotide sequence according to (52), the result of extraction obtained in process (c) above is transmitted to the requester of the object and/or the service and/or a user of the result of extraction through a transmitter/receiver.

54. A program for processing information on a nucleotide sequence which allows a computer to execute processes including:
(a) receiving through a transmitter/receiver positional information representing a position in a nucleotide sequence in accordance with a request for an object and/or service;
(b) obtaining through a controller nucleotide sequence-related information associated with positional information corresponding to the positional information received in process (a) above; and
(c) transmitting through a transmitter/receiver the nucleotide sequence-related information obtained in process (b) above.

55. The program for processing information on a nucleotide sequence according to (54), in process (b) above, nucleotide sequence-related information is obtained from a recording medium.

56. The program for processing information on a nucleotide sequence according to (54), in process (c) above, the nucleotide sequence-related information is transmitted to an information processor which provided the positional information.

57. The program for processing information on a nucleotide sequence according to (54), in process (a) above, the positional information as well as secondary positional information which is set according to the positional information are received and, in process (c) above, the nucleotide sequence-related information obtained in process (b) above is transmitted in association with the secondary positional information.

58. The program for processing information on a nucleotide sequence according to (54) comprising, prior to process (a) above, process (d) transmitting through a transmitter/receiver the request information for the object and/or the service and, after process (c) above, process (e) receiving semantic information implied by the nucleotide sequence-related information transmitted in process (c) above and/or information associated with the semantic information through a transmitter/receiver.

59. A program for processing information on a nucleotide sequence which allows a computer to execute processes including:
(a) receiving through a transmitter/receiver positional information, in accordance with a request for an object and/or service, representing a position in a nucleotide sequence; a plurality of pieces of nucleotide sequence-related information associated with the positional information; and semantic information and/or information associated with the semantic information, which is associated with each of the plurality of pieces of nucleotide sequence-related information respectively; and
(b) from among a plurality of combinations of the positional information and the nucleotide sequence-related information received in process (a) above, selecting a combination corresponding to a combination of positional information and nucleotide sequence-related information possessed by the requester, and extracting through a controller semantic information and/or information associated with the semantic information, which is associated with nucleotide sequence-related information contained in the selected combination.

60. A program for processing information on a nucleotide sequence which allows a computer to execute processes including:
(a) transmitting through a transmitter/receiver positional information representing a position in a nucleotide sequence, and nucleotide sequence-related information associated with the positional information;
(b) transmitting through a transmitter/receiver request information for an object and/or service; and
(c) receiving through a transmitter/receiver semantic information implied by nucleotide sequence-related information corresponding to positional information in accordance with the request information and/or information associated with the semantic information.

61. An apparatus for processing information on a nucleotide sequence comprising:
a transmitter/receiver that receives request information for an object and/or service; and
a controller that obtains: positional information in accordance with the request information from a memory having positional information representing a position in a nucleotide sequence memorized therein; nucleotide sequence-related information corresponding to the obtained positional information among nucleotide sequence-related information associated with positional information; and semantic information implied by the nucleotide sequence-related information and/or information associated with the semantic information.

62. The apparatus for processing information on a nucleotide sequence according to (61), the transmitter/receiver transmits the semantic information and/or the information associated with the semantic information to an information processor which provided the request information and/or a user of the semantic information and/or the information associated with the semantic information.

63. The apparatus for processing information on a nucleotide sequence according to (61), the transmitter/receiver at least transmits the obtained positional information, and the controller, followed by receiving nucleotide sequence-related information corresponding to the transmitted positional information from among nucleotide sequence-related information associated with positional information, obtains semantic information implied by the received nucleotide sequence-related information and/or information associated with the semantic information.

64. The apparatus for processing information on a nucleotide sequence according to (63), the controller sets secondary positional information corresponding to the obtained positional information, the transmitter/receiver transmits the obtained positional information in association with the secondary positional information, and the controller, followed by receiving the nucleotide sequence-related information in association with the secondary positional information, obtains semantic information implied by the nucleotide sequence-related information associated with the positional information through the secondary positional information and/or information associated with the semantic information.

65. The apparatus for processing information on a nucleotide sequence according to (63), the controller extracts, from a memory having memorized therein a plurality of pieces of positional information, a plurality of pieces of nucleotide sequence-related information associated with each of the plurality of pieces of positional information, and semantic information implied by each of the plurality of pieces of nucleotide sequence-related information, respectively, semantic information associated with nucleotide sequence-related information corresponding to the positional information transmitted through the transmitter/receiver, to obtain semantic information implied by the received nucleotide sequence-related information.

66. The apparatus for processing information on a nucleotide sequence according to (61), the controller obtains a plurality of pieces of nucleotide sequence-related information corresponding to the obtained positional information, and semantic information implied by each of the plurality of pieces of nucleotide sequence-related information and/or information associated with the semantic information.

67. The apparatus for processing information on a nucleotide sequence according to (61), the transmitter/receiver at least receives nucleotide sequence-related information associated with positional information, and the controller obtains nucleotide sequence-related information corresponding to the obtained positional information using the received nucleotide sequence-related information.

68. The apparatus for processing information on a nucleotide sequence according to (67), the controller extracts, from a memory having memorized therein a plurality of pieces of positional information, a plurality of pieces of nucleotide sequence-related information associated with each of the plurality of pieces of positional information, and semantic information implied by each of the plurality of pieces of nucleotide sequence-related information, respectively, semantic information associated with nucleotide sequence-related information corresponding to the nucleotide sequence-related information received through the transmitter/receiver, to obtain semantic information implied by the obtained nucleotide sequence-related information.

69. The apparatus for processing information on a nucleotide sequence according to (61), the controller determines whether transmission of the semantic information and/or the information associated with the semantic information is approved or not.

70. The apparatus for processing information on a nucleotide sequence according to (61), the controller obtains: a plurality of pieces of positional information in accordance with the request information; nucleotide sequence-related information corresponding to each of the plurality of pieces of the obtained positional information from among nucleotide sequence-related information associated with positional information; and semantic information implied by a combination of the nucleotide sequence-related information and/or information associated with the semantic information.

71. An apparatus for processing information on a nucleotide sequence comprising:
a controller that obtains positional information in accordance with request information for an object and/or service from a memory having positional information representing a position in a nucleotide sequence memorized therein; and
a transmitter/receiver that receives the request information, at least transmits the positional information obtained through the controller, and receives nucleotide sequence-related information corresponding to the transmitted positional information.

72. The apparatus for processing information on a nucleotide sequence according to (71), the controller sets secondary positional information corresponding to the obtained positional information, and the transmitter/receiver transmits the obtained positional information in association with the secondary positional information, and receives the nucleotide sequence-related information in association with the secondary positional information.

73. An apparatus for processing information on a nucleotide sequence comprising:
a transmitter/receiver that receives nucleotide sequence-related information associated with positional information, in accordance with request information for an object and/or service, representing a position in a nucleotide sequence; and
a controller that obtains semantic information implied by the nucleotide sequence-related information received through the transmitter/receiver and/or information associated with the semantic information.

74. The apparatus for processing information on a nucleotide sequence according to (73), the controller extracts, from a memory having memorized therein a plurality of pieces of positional information, a plurality of pieces of nucleotide sequence-related information associated with each of the plurality of pieces of positional information, and semantic information implied by each of the plurality of pieces of nucleotide sequence-related information, respectively, semantic information associated with nucleotide sequence-related information corresponding to the nucleotide sequence-related information which is received through the transmitter/receiver, to obtain semantic information implied by the nucleotide sequence-related information.

75. The apparatus for processing information on a nucleotide sequence according to (73), the transmitter/receiver transmits the semantic information and/or the information associated with the semantic information obtained through the controller to at least one of: an information processor which provided the nucleotide sequence-related information; an information processor which provided the request information; and a user of the semantic information and/or the information associated with the semantic information.

76. The apparatus for processing information on a nucleotide sequence according to (73), the controller determines whether transmission of the semantic information and/or the information associated with the semantic information is approved or not.

77. The apparatus for processing information on a nucleotide sequence according to (73), the transmitter/receiver receives nucleotide sequence-related information associated with each of a plurality of pieces of positional information in accordance with request information, and the controller obtains semantic information implied by a combination of the nucleotide sequence-related information and/or information associated with the semantic information.

78. An apparatus for processing information on a nucleotide sequence comprising:
a controller that obtains semantic information on a predetermined individual organism that is implied by nucleotide sequence-related information associated with positional information, in accordance with a request for an object and/or service, representing a position in a nucleotide sequence, searches semantic information on an other individual organism(s) from a memory having semantic information implied by nucleotide sequence-related information on the other individual organism(s) memorized therein, and judges the compatibility between the semantic information on the predetermined individual organism and the semantic information on the other individual organism(s).

79. The apparatus for processing information on a nucleotide sequence according to (78) comprising a transmitter/receiver that transmits information on the judgment obtained through the controller to the requester of the object and/or the service and/or a user of the information on the judgment.

80. An apparatus for processing information on a nucleotide sequence comprising:
a controller that obtains semantic information that is implied by nucleotide sequence-related information associated with positional information, in accordance with a request for an object and/or service, representing a position in a nucleotide sequence and that interrelates information on a predetermined individual organism and information on an other individual organism, extracts nucleotide sequence-related information associated with positional information, with which semantic information containing information on a predetermined individual organism which is recognized as in conformity with information on an other individual organism contained in the obtained semantic information is associated, and extracts from a memory having information for discriminating an individual organism in association with nucleotide sequence-related information associated with positional information memorized therein, information for discriminating an individual organism associated with the extracted nucleotide sequence-related information.

81. The apparatus for processing information on a nucleotide sequence according to (80) comprising a transmitter/receiver that transmits the result of extraction obtained through the controller to the requester of the object and/or the service and/or a user of the result of extraction.

82. An apparatus for processing information on a nucleotide sequence comprising:
a controller that controls reception of positional information, in accordance with a request for an object and/or service, representing a position in a nucleotide sequence, obtainment of nucleotide sequence-related information associated with positional information corresponding to the received positional information, and transmission of the obtained nucleotide sequence-related information.

83. The apparatus for processing information on a nucleotide sequence according to (82), the controller obtains nucleotide sequence-related information from a recording medium.

84. The apparatus for processing information on a nucleotide sequence according to (82) comprising a transmitter/receiver that transmits the nucleotide sequence-related information.

85. The apparatus for processing information on a nucleotide sequence according to (82), the controller controls reception of the positional information as well as secondary positional information which is set according to the positional information and transmission of the obtained nucleotide sequence-related information associated with the secondary positional information.

86. The apparatus for processing information on a nucleotide sequence according to (82), the controller controls transmission of the request information for the object and/or the service and reception of semantic information implied by the transmitted nucleotide sequence-related information and/or information associated with the semantic information.

87. An apparatus for processing information on a nucleotide sequence comprising:
a transmitter/receiver that receives positional information, in accordance with a request for an object and/or service, representing a position in a nucleotide sequence; a plurality of pieces of nucleotide sequence-related information associated with the positional information; and semantic information and/or information associated with the semantic information, which is associated with each of the plurality of pieces of nucleotide sequence-related information respectively; and
a controller that selects, from among a plurality of combinations of the positional information and the nucleotide sequence-related information which were received through the transmitter/receiver, a combination corresponding to a combination of positional information and nucleotide sequence-related information possessed by the requester, and extracts semantic information and/or information associated with the semantic information, which is associated with nucleotide sequence-related information contained in the selected combination.

88. An apparatus for processing information on a nucleotide sequence comprising:

a transmitter/receiver that transmits positional information representing a position in a nucleotide sequence and nucleotide sequence-related information associated with the positional information, transmits request information for an object and/or service, and receives semantic information implied by nucleotide sequence-related information corresponding to positional information in accordance with the request information and/or information associated with the semantic information.

89. A recording medium having a program for processing information on a nucleotide sequence recorded thereon which allows a computer to execute processes including:

(a) receiving request information for an object and/or service through a transmitter/receiver;

(b) from a memory having positional information representing a position in a nucleotide sequence memorized therein, obtaining through a controller positional information in accordance with the request information; and (c) from among nucleotide sequence-related information associated with positional information, obtaining through a controller nucleotide sequence-related information corresponding to the positional information obtained in process (b) above, and obtaining through a controller semantic information implied by the nucleotide sequence-related information and/or information associated with the semantic information.

90. A recording medium having a program for processing information on a nucleotide sequence recorded thereon which allows a computer to execute processes including:

(a) receiving request information for an object and/or service through a transmitter/receiver;

(b) obtaining through a controller positional information in accordance with the request information from a memory having positional information representing a position in a nucleotide sequence memorized therein;

(c) transmitting through a transmitter/receiver, at least, the positional information obtained in process (b) above; and (d) receiving through a transmitter/receiver nucleotide sequence-related information corresponding to the positional information transmitted in process (c) above.

91. A recording medium having a program for processing information on a nucleotide sequence recorded thereon which allows a computer to execute processes including:

(a) receiving through a transmitter/receiver nucleotide sequence-related information associated with positional information representing a position in a nucleotide sequence, in accordance with request information for an object and/or service; and (b) obtaining through a controller semantic information implied by the nucleotide sequence-related information received in process (a) above and/or information associated with the semantic information.

92. A recording medium having a program for processing information on a nucleotide sequence recorded thereon which allows a computer to execute processes including:

(a) receiving through a transmitter/receiver positional information representing a position in a nucleotide sequence in accordance with a request for an object and/or service;

(b) obtaining through a controller nucleotide sequence-related information associated with positional information corresponding to the positional information received in process (a) above; and (c) transmitting through a transmitter/receiver the nucleotide sequence-related information obtained in process,(b) above.

93. The recording medium having a program for processing information on a nucleotide sequence recorded thereon according to (92) comprising, prior to process (a) above, process (d) transmitting through a transmitter/receiver the request information for the object and/or the service and, after process (c) above, process (e) receiving semantic information implied by the nucleotide sequence-related information transmitted in process (c) above and/or information associated with the semantic information through a transmitter/receiver.

94. A recording medium having a program for processing information on a nucleotide sequence recorded thereon which allows a computer to execute processes including:

(a) receiving through a transmitter/receiver positional information, in accordance with a request for an object and/or service, representing a position in a nucleotide sequence; a plurality of pieces of nucleotide sequence-related information associated with the positional information; and semantic information and/or information associated with the semantic information, which is associated with each of the plurality of pieces of nucleotide sequence-related information respectively; and (b) from among a plurality of combinations of the positional information and the nucleotide sequence-related information received in process (a) above, selecting a combination corresponding to a combination of positional information and nucleotide sequence-related information possessed by the requester, and extracting through a controller semantic information and/or information associated with the semantic information, which is associated with nucleotide sequence-related information contained in the selected combination.

95. A recording medium having a program for processing information on a nucleotide sequence recorded thereon which allows a computer to execute processes including:

(a) transmitting through a transmitter/receiver positional information representing a position in a nucleotide sequence, and nucleotide sequence-related information associated with the positional information;

(b) transmitting through a transmitter/receiver request information for an object and/or service; and (c) receiving through a transmitter/receiver semantic information implied by nucleotide sequence-related information corresponding to positional information in accordance with the request information and/or information associated with the semantic information.

96. A system for processing information on a nucleotide sequence which comprises:

an information processor for a requester which transmits request information for an object and/or service, and which is capable of obtaining nucleotide sequence-related information; and an information processor for a provider which provides semantic information implied by nucleotide sequence-related information and/or information associated with the semantic information, and which is capable of obtaining positional information representing a position in a nucleotide sequence and semantic information implied by nucleotide sequence-related information corresponding to the positional information and/or information associated with the semantic information, and obtaining semantic information implied by nucleotide sequence-related information associated with positional information in accordance with the request information from the information processor for a requester and/or information associated with the semantic information.

97. A method for processing information on a nucleotide sequence comprising steps of:
(a) receiving request information for an object and/or service;
(b) obtaining positional information in accordance with the request information from a memory having positional information representing a position in a nucleotide sequence memorized therein; and
(c) obtaining nucleotide sequence-related information corresponding to the positional information obtained in step (b) above, and obtaining semantic information implied by the nucleotide sequence-related information and/or information associated with the semantic information.

98. A program for processing information on a nucleotide sequence which allows a computer to execute processes including:
(a) receiving request information for an object and/or service through a transmitter/receiver;
(b) from a memory having positional information representing a position in a nucleotide sequence memorized therein, obtaining through a controller positional information in accordance with the request information; and
(c) obtaining through a controller nucleotide sequence-related information corresponding to the positional information obtained in process (b) above, and obtaining through a controller semantic information implied by the nucleotide sequence-related information and/or information associated with the semantic information.

99. An apparatus for processing information on a nucleotide sequence comprising:
a transmitter/receiver that receives request information for an object and/or service; and
a controller that obtains: positional information in accordance with the request information from a memory having positional information representing a position in a nucleotide sequence memorized therein; nucleotide sequence-related information corresponding to the obtained positional information; and semantic information implied by the nucleotide sequence-related information and/or information associated with the semantic information.

100. A recording medium having a program for processing information on a nucleotide sequence recorded thereon which allows a computer to execute processes including:
(a) receiving request information for an object and/or service through a transmitter/receiver;
(b) from a memory having positional information representing a position in a nucleotide sequence memorized therein, obtaining through a controller positional information in accordance with the request information; and
(c) obtaining through a controller nucleotide sequence-related information corresponding to the positional information obtained in process (b) above, and obtaining through a controller semantic information implied by the nucleotide sequence-related information and/or information associated with the semantic information.

BRIEF DESCRIPTION OF THE DRAWINGS

FIG. 3 is a diagram showing construction of an embodiment of data that is recorded in a main database ("database" is hereinafter abbreviated to "DB").

FIG. 5 is a diagram showing construction of an embodiment of data recorded on a genome-related information recording medium.

FIG. 10 is a diagram showing construction of an embodiment of data recorded in a main DB that is utilized in a system for providing a medicament that is appropriate for the diathesis.

FIG. 11 is a flow chart showing processing in a shared computer and a personal computer in a system for providing a medicament that is appropriate for the diathesis.

FIG. 16 shows a screen image indicated as an example of a confirmation screen.

FIG. 17 is a diagram showing construction of data stored in memory section A in a system for providing a medicament that is appropriate for the diathesis.

FIG. 18 is a diagram showing construction of data stored in memory section B in a system for providing a medicament that is appropriate for the diathesis.

FIG. 19 is a diagram showing construction of information that is transmitted to a provider of a medicament in a system for providing a medicament that is appropriate for the diathesis.

FIG. 20 is a diagram showing construction of an embodiment of data recorded in a main DB used in a system for providing medical examination items depending on diathesis.

FIG. 21 is a diagram showing construction of an embodiment of data recorded in a link DB used in a system for providing medical examination items depending on the diathesis.

FIG. 22 is a diagram showing construction of an embodiment of data recorded on a genome-related information recording medium used in a system for providing medical examination items depending on the diathesis.

FIG. 27 is a diagram showing construction of an embodiment of data recorded in a medical examination table used in a system for providing medical examination items depending on the diathesis.

FIG. 28 shows a screen image indicated as an example of an input screen for individual IC confirmation.

FIG. 29 is a diagram showing construction of data stored in memory section B in a system for providing medical examination items depending on the diathesis.

FIG. 30 is a diagram showing construction of data stored in memory section A in a system for providing medical examination items depending on the diathesis.

FIG. 31 shows a screen image representing an example of an output format in a system for providing medical examination items depending on the diathesis.

FIG. 32 is a diagram showing construction of an embodiment of data recorded in a main DB used in a system for providing information on other individual organisms having properties compatible with a "given property" of the requestor.

FIG. 33 is a diagram showing construction of an embodiment of data recorded on a genome-related information recording medium used in a system for providing information on other individual organisms having properties compatible with a "given property" of the requestor.

FIG. 35 is a diagram showing construction of a donor DB constructed in a system for donor registration for registering an individual's own polymorphism pattern.

DESCRIPTION OF REFERENCE NUMERALS

1: communication network
2: shared computer
3: personal computer

EMBODIMENT FOR CARRYING OUT THE INVENTION

The present invention is described in detail below with reference to the drawings.

1. First Embodiment

First, a system for processing information which provides the morbidity rate of predetermined diseases to a user is described as a first embodiment to which the present invention has been applied. The present embodiment is directed to explanation of a system for providing the morbidity rate in accordance with the request information requested by a user and, thus, is explained as a simple model for the convenience of explanation.

Figure 1:
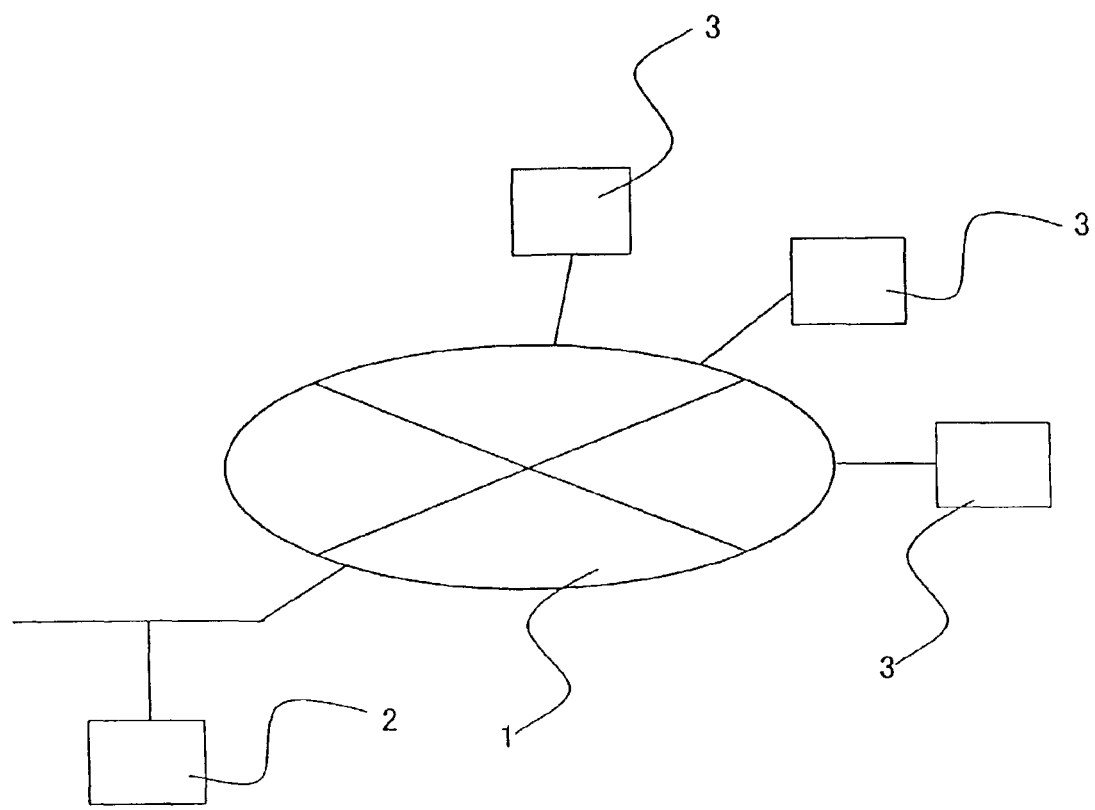
FIG. 1 is a schematic view showing a construction of a system for processing information to which the present invention has been applied.

As shown in FIG. 1, the system for processing information comprises a communication network 1, such as the Internet, a shared computer 2 connected to communication network 1, and a plurality of personal computers 3 connected to communication network 1, and enables data communication between shared computer 2 and personal computers 3 through communication network 1.

Figure 2:
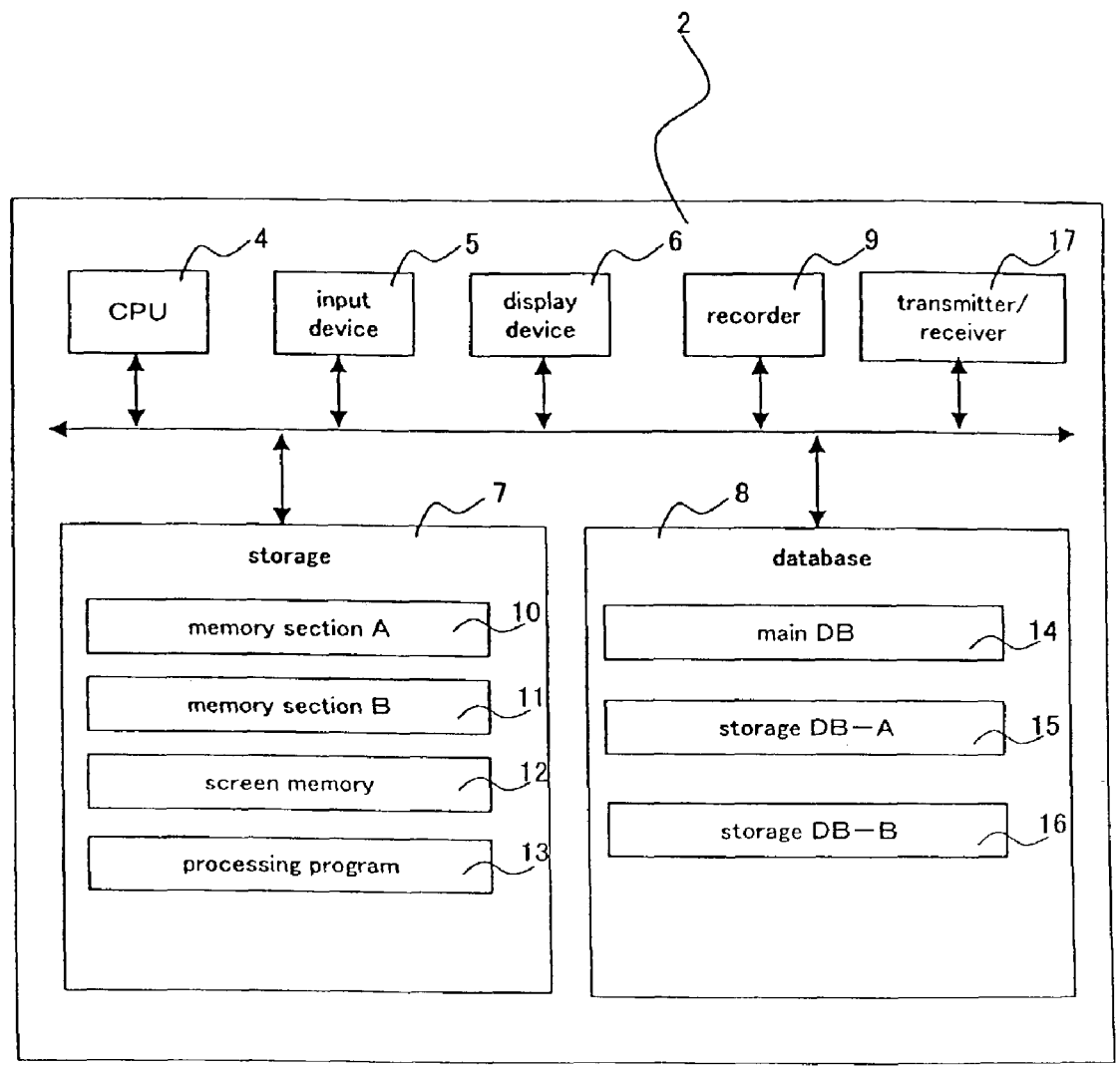
FIG. 2 is a schematic view showing a construction of a shared computer.

As shown in FIG. 2, shared computer 2 is constituted by a CPU 4 that totally controls the operation of the shared computer 2; an input device 5, such as a keyboard and a mouse, with which information, instructions for executing a program and the like can be input; a display device 6 such as a display apparatus; a storage 7 in which temporary information, unrewritable information and the like are recorded; a database 8 for storing various data; a recorder 9 for writing predetermined information in storage 7 and database 8; and a transmitter/receiver 17 for transmission and reception of information to and from personal computers 3 through communication network 1.

Storage 7 in shared computer 2 is constituted by a memory section A10 and a memory section B11 which respectively record different types of information; a screen memory 12 having recorded therein screen data displayed, for example, on personal computer 3 or display device 6; and a processing program 13 for operating the system. Shared computer 2 may have screen memory 12, processing program 13 and the like in an external recording apparatus (not shown) connected to shared computer 2 through communication network 1 instead of containing those in storage 7 inside shared computer 2.

Database 8 (described as "memory" in Claim) in shared computer 2 is constituted by a main DB 14 in which a polymorphism address, a polymorphism pattern, and semantic information are recorded; a storage DB-A15 for saving information recorded in memory section A10; and a storage DB-B16 for saving information recorded in memory section B11.

As shown in FIG. 3, polymorphism addresses, a plurality of possible polymorphism patterns in the polymorphism address respectively, and semantic information implied by each of the plurality of polymorphism patterns respectively are stored in association with one another in main DB 14. Main DB 14 may also have recorded therein semantic information implied by a combination of polymorphism patterns in a plurality of polymorphism addresses (such as haplotype).

The "polymorphism address (positional information)" refers to, at least, a position in a nucleotide sequence where a polymorphism is present. In general, the term "polymorphism" includes, for example, a so-called SNP (single nucleotide polymorphism), RFLP (restriction fragment length of polymorphism), VNTR (variable number of tandem repeat), and microsatellite. However, the term "polymorphism" used herein is not limited to these and also includes a variation in nucleotides and nucleotide sequences existing only at a frequency of less than 1% in an individual species. Therefore, "polymorphism address" also includes a position in a nucleotide sequence which indicates a variation of a nucleotide and nucleotide sequences existing only at a frequency of less than 1% in an individual species. Specifically, the "polymorphism address" indicates a position representing a polymorphism or the like by a combination of numerical values, letters, symbols, and the like. The polymorphism address is not particularly limited, for example, may be represented by a combination of a chromosome number, a symbol indicating a gene having a polymorphism therein, and a numerical value indicating a position of a polymorphism in the gene. Alternatively, it may be a combination of a symbol indicating a gene having polymorphism therein and a numerical value indicating a position of polymorphism in the gene.

Further, a "polymorphism address" may be a notation peculiar to a polymorphism imparted to each polymorphism. When the notation peculiar to a polymorphism is used as a polymorphism address, the polymorphism address does not directly indicate the position in the nucleotide sequence, instead, the position can be indirectly found by the notation peculiar to the polymorphism. Therefore, the "polymorphism address" includes the notation peculiar to the polymorphism.

A "polymorphism pattern (nucleotide sequence-related information)" is information on nucleotide sequences which differ among individual organisms, and contains, at least, a pattern of nucleotides or nucleotide sequences in a polymorphism. In addition, the "polymorphism pattern" includes a pattern of nucleotide and nucleotide sequences existing only at a frequency of less than 1% in an individual species and is not limited to a polymorphism. For example, in a polymorphism address known to have A or G, the "polymorphism pattern" is represented either by "A" or "G".

The "polymorphism pattern" may represent a heterozygote or homozygote in a homologous chromosome. For example, the "polymorphism pattern" can be represented by "AA", "GG", or "AG" in the polymorphism address known to have A or G.

Further, the "polymorphism pattern" may indirectly represent a possible pattern in the predetermined polymorphism address instead of direct representation of patterns. For example, in the polymorphism address known to have A or G the "polymorphism pattern" may be represented by "allele 1" when the polymorphism address has "A" or "allele 2" when the polymorphism address has "G". As described above, when the "polymorphism pattern" can be expressed as "AA", "GG", or "AG", the "polymorphism pattern" may be represented by "α" when expressed as "AA", it may be represented by "β" when expressed as "GG", and it may be represented by "γ" when expressed as "AG".

When the polymorphism is the microsateltite type the "polymorphism pattern" may be represented, for example, by numerical values indicating "the number of repetitions" and when the polymorphism is the insertion/deletion type the "polymorphism pattern" may be represented, for example, by symbols indicating "presence/absence".

The term "semantic information" used herein refers to information associated with the "polymorphism pattern," for example, information including responsiveness to medicaments, side-effect caused by medicaments, a risk against diseases and disorders, diatheses and properties, interaction among proteins, and various phenotypes caused by differences in polymorphism patterns. "Semantic information" is a type of information which is corrected and increases in the numbers of types accompanied by progress in research on genome and genetics, and constant updating is preferred. In other words, "semantic information" becomes more accurate through increases and decreases in the amount of information accumulated by updating a database/using the results of research on genome and genetics.

Information that is further induced from "semantic information" is "information associated with the semantic information" although it is not directly associated with the "polymorphism pattern." When "semantic information" is a risk against diseases, when the relevant risk exceeds a given standard, for example, specific "medical examination items" are derived. These specific "medical examination items" are "information associated with the semantic information."

In the present embodiment, semantic information is recorded in main DB 14 as "annotative information on the polymorphism pattern" associated with at least the predetermined "polymorphism address" and "polymorphism pattern" as shown in FIG. 3. Also, semantic information is associated with, for example, "polymorphism classification," "classification (name of diseases)" and the like corresponding to the predetermined "polymorphism address." Consequently, when a predetermined "polymorphism address" is a predetermined "polymorphism pattern," types of diseases and annotative information (semantic information) on the morbidity rates of diseases can be obtained. For example, semantic information can be associated with a combination of respective polymorphism patterns corresponding to a plurality of polymorphism addresses (such as haplotype). In other words, each combination of polymorphism patterns in a plurality of polymorphism addresses can be respectively associated with annotative information (semantic information) representing different morbidity rates for predetermined diseases. In this case, when a plurality of polymorphism addresses are a combination of predetermined polymorphism patterns, annotative information (semantic information) indicating the morbidity rate of a predetermined disease can be obtained.

Semantic information can be further associated with a "level of disclosure" which is set in accordance with a predetermined standard. For example, a standard in setting a "level of disclosure" can be determined by taking into consideration unpredictable disbenefits and the like for individuals that would be caused by disclosure of semantic information, i.e., the morbidity rate of "classification (name of disease)". In particular, in shared computer 2, a "level of disclosure" can be set such that semantic information, the disclosure of which is inappropriate from the view point of, for example, law, regulations, the behavioral norms of an organization having the shared computer 2 or a contract with the user, is not disclosed. In this case, with this system, annotative information representing a morbidity rate associated with a "level of disclosure" at which disclosure is not possible is not disclosed to users. This can prevent the provision of semantic information which could result in unpredictable disbenefit for users or the disclosure of semantic information to parties other than the contract party.

The system may disclose semantic information having a predetermined "level of disclosure" associated therewith to the user through approval by the user of disclosure of semantic information having a predetermined "level of disclosure" associated therewith through, for example, informed consent.

The "level of disclosure" can be set as a plurality of levels of three or more, for example, "1, 2, 3 . . . " or "a, b, c . . . ". In this case, the level can be set on the shared computer 2 side according to the type of user, such as the user's age, the user's qualification, and whether or not a contract exists with the user. The user can select the level of disclosure such that only annotative information is provided which represents the morbidity rate associated with the level of disclosure that is above (or below) the predetermined level of disclosure determined in accordance with the informed consent or the like.

In database 8, for example, data such as nucleotide sequence-related information that is the genetic information of the individual requester utilizing the system can be recorded in storage DB-B16. In storage DB-A15, for example, data such as information distinguishing the requester from others utilizing the system can be recorded. In this way, the separate recording of the genetic information of individuals and the information for specifying individuals in storage DB-A15 and storage DB-B16, respectively, makes it difficult to associate a user's genetic information with data that specifies the user.

Shared computer 2 is not limited to one having database 8 therein, and it may have an external database (not shown) connected to shared computer 2 through communication network 1. Shared computer 2 may have a plurality of databases 8 therein or may have an internal database 8 and an external database connected to shared computer 2 through communication network 1.

Figure 4:
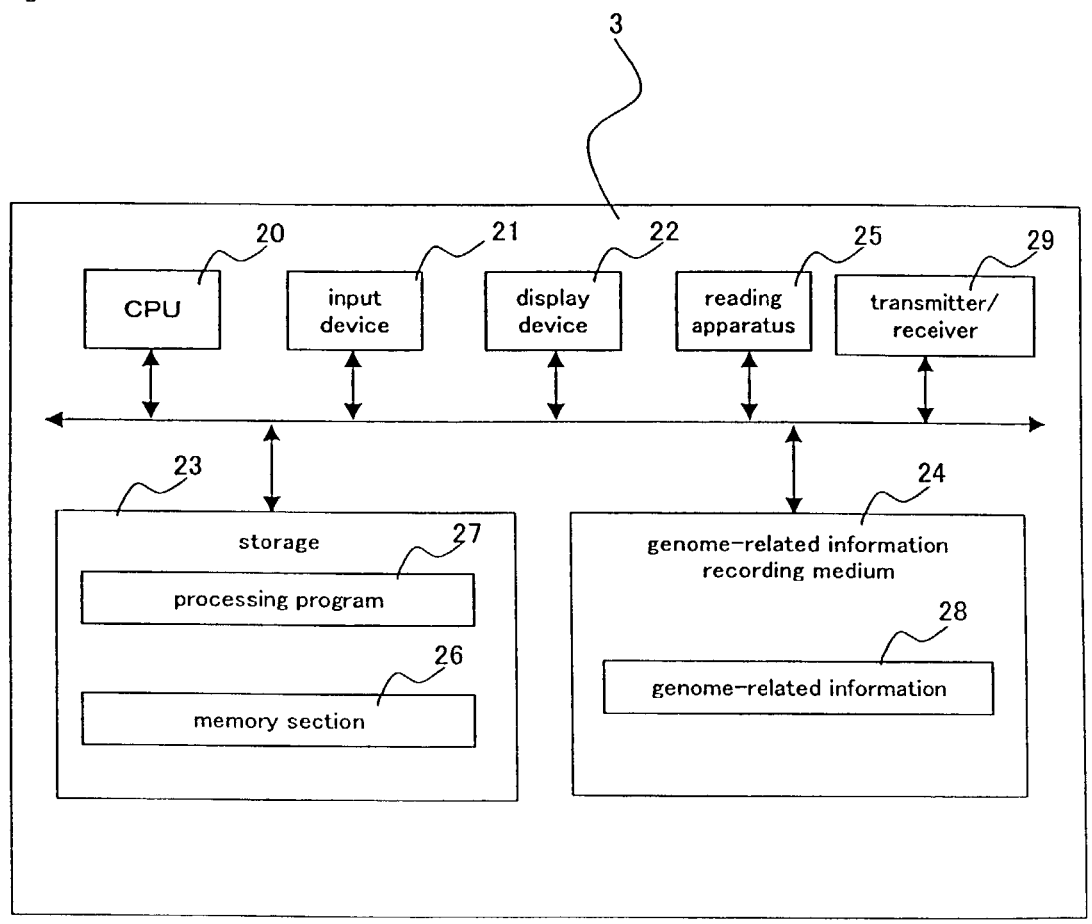
FIG. 4 is a schematic view showing a construction of a personal computer.

As shown in FIG. 4, personal computer 3 is constituted by CPU 20 that totally controls operation of personal computer 3, input device 21 such as a keyboard and a mouse with which information and instructions for executing a program are input, display device 22 such as a display apparatus, storage 23 having temporary information, rewritable information and the like recorded therein, reading apparatus 25 for reading data from genome-related information recording medium 24, and transmitter/receiver 29 for transmitting and receiving information to and from shared computer 2 through communication network 1. Personal computer 3 is not limited to a commonly used computer. For example, it may be any form of cellular phone, personal digital assistance, or other mobile communication tool.

Storage 23 in personal computer 3 has a memory section 26 for recording information provided from genome-related information recording medium 24 and the like, and is recorded a processing program 27 for operating the system for processing information.

Genome-related information recording medium 24 has genome-related information 28 of an individual recorded thereon. Genome-related information recording medium 24 includes, for example, a magnetic recording medium such as a magnetic disk or a magnetic card, an optical recording medium employing such as a magneto-optic recording system or a phase-change recording system, and a semiconductor memory. This genome-related information recording medium 24 may be in any form such as, for example, card, disk, stick, tape, or drum. Further, this genome-related information recording medium 24 may comprise genome-related information 28 of a single individual (an individual organism) recorded thereon. Alternatively, it may comprise a plurality of pieces of genome-related information 28 on a plurality of individuals (individual organisms) recorded thereon.

Genome-related information 28 contained in genome-related information recording medium 24 refers to, at least, a "polymorphism address" and a "polymorphism pattern" in the predetermined polymorphism address obtained as a result of analysis of an individual's (individual organism's) nucleotide sequences. Genome-related information 28 may contain various information, such as information concerning anamnesis, characteristics, an individual's clinical record, or a result of medical examination.

On genome-related information recording medium 24, recorded as genome-related information 28 is, for example, as shown in FIG. 5, the individual's number "Gno." (G number) peculiar to genome-related information 28 as well as the individual's information, such as date of birth, as data I; polymorphism addresses and polymorphism patterns as data II; anamnesis information as data III; characteristics as data IV; and information concerning the individual's clinical record and the like as data V. In other words, genome-related information 28 is constituted by data I, data II, data III, data IV, and data V. Data I and data II contain essential information and data III, data IV, and data V are respectively constituted by additional information.

In genome-related information 28, the "polymorphism address" corresponding to the position on the nucleotide sequence is linked with the "polymorphism pattern" in the polymorphism address and recorded. Additional information in a predetermined polymorphism address may be recorded in data II as a "comment" linked with a "polymorphism address". All the nucleotide sequences of a predetermined individual organism may be recorded in data II. Even when all the nucleotide sequences are recorded in data II, "polymorphism addresses" and "polymorphism patterns" are contained within data II.

According to the present invention, personal computer 3 and genome-related information recording medium 24 are not limited to the construction as shown in FIGS. 4 and 5 respectively. For example, a genome-related information recording medium may be equipped with a memory section having a processing program and a personal computer may have the genome-related information recording medium mounted thereon to operate the processing program. In this case, a personal computer can be operated in accordance with a processing program recorded in a memory section on a genome-related information recording medium.

Figure 6:
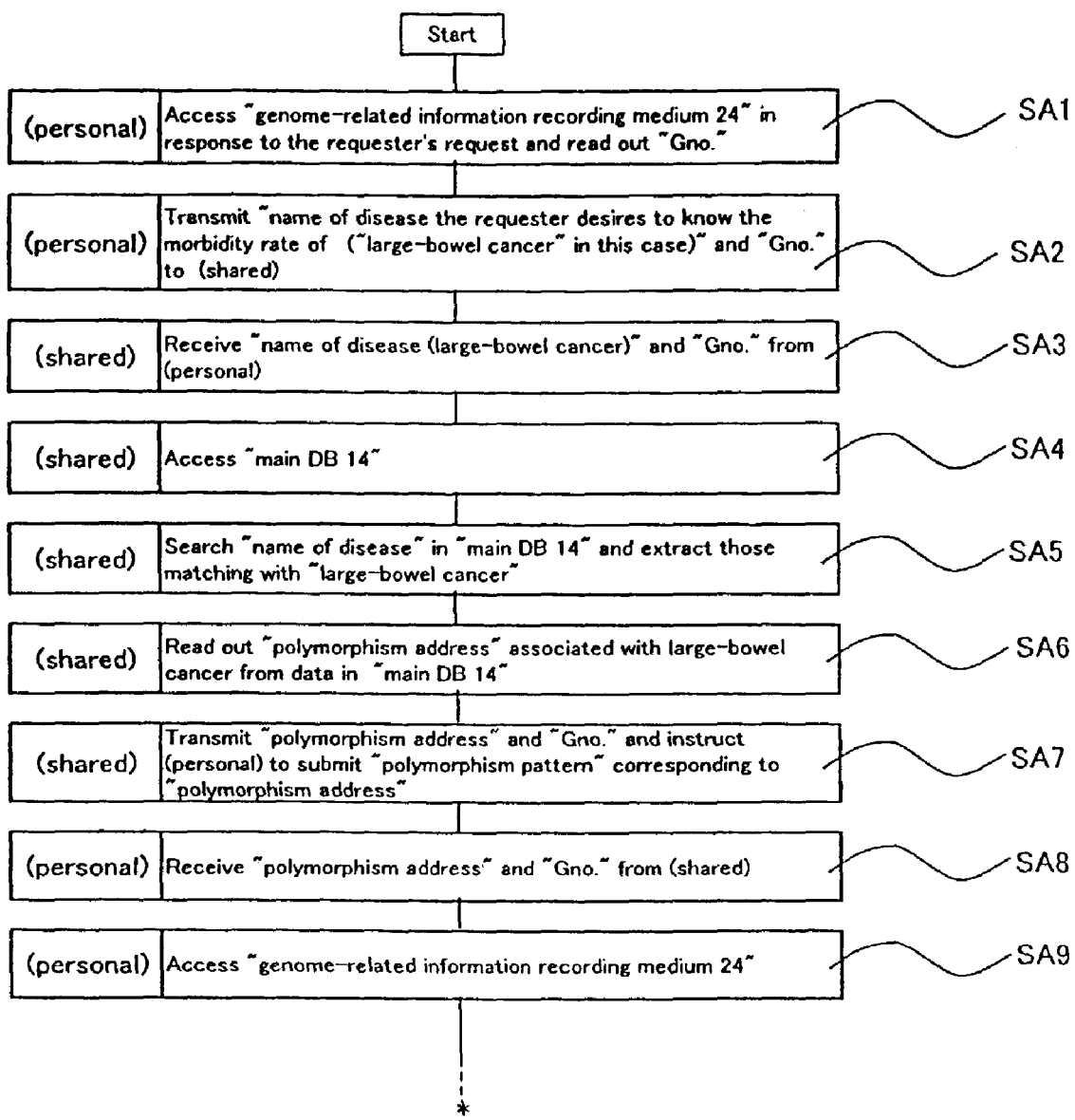
FIG. 6 is a flow chart showing processing in a shared computer and a personal computer in a system for providing a morbidity rate of a predetermined disease.
Figure 7:
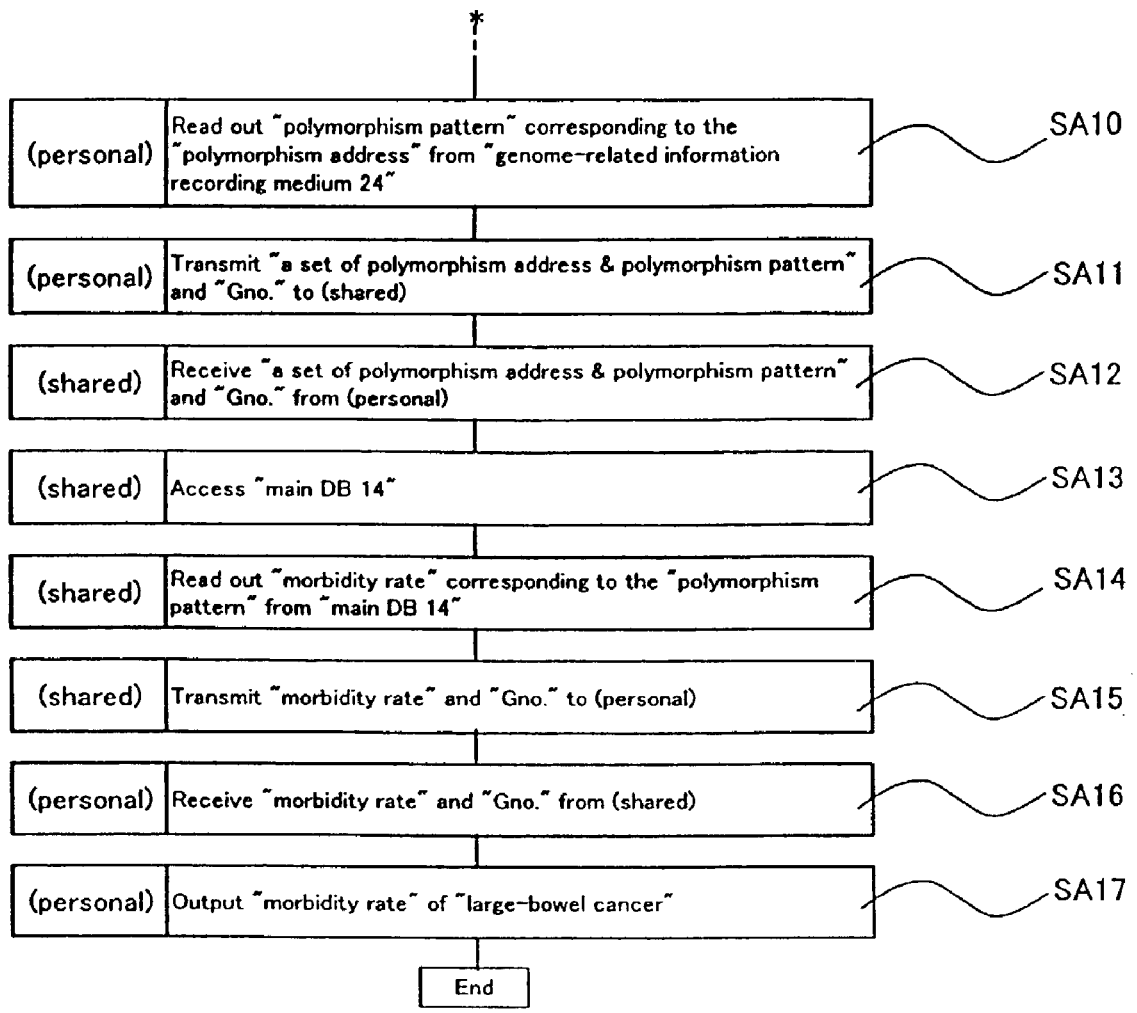
FIG. 7 is a flow chart, which is a continuation of FIG. 6, showing processing in a shared computer and a personal computer in a system for providing a morbidity rate of a predetermined disease.

In a system for processing information having the above construction, processing program 13 recorded in storage 7 in shared computer 2 and processing program 27 recorded in storage 23 in personal computer 3 process information in accordance with, for example, flow charts as shown in FIGS. 6 and 7. In the flow charts as shown in FIGS. 6 and 7, a step described as "(shared)" refers to processing in shared computer 2 and a step described as "(personal)" refers to processing in personal computer 3.

The system for processing information is a system in which an individual possessing genome-related information recording medium 24 accesses shared computer 2 using personal computer 3 through communication network 1 and utilizes semantic information recorded in main DB 14 in shared computer 2. The system for processing information may be a system comprising the genome-related information recording medium 24, having genome-related information 28 on a plurality of individuals recorded thereon, to which individuals respectively access.

In this case, when utilizing the system, the requester first starts processing program 27, which is recorded in storage 23, in step A1 (SA1). Processing program 27 drives reading apparatus 25 in personal computer 3 to access genome-related information recording medium 24. Thus, "Gno." recorded as data I on genome-related information recording medium 24 is read out and the read-out "Gno." is stored in memory section 26.

In step A2 (SA2), based on a screen image displayed by processing program 27 on display device 22, information, the provision of which is desired by the requester wishes to receive, for example, the "morbidity rate of large-bowel cancer" (requested information), is input to personal computer 3. At the same time, the "morbidity rate of large-bowel cancer" and "Gno." are transmitted to shared computer 2 from personal computer 3 through communication network 1. Alternatively, the requester writes the "morbidity rate of large-bowel cancer" and "Gno." in shared computer 2 from personal computer 3 through communication network 1.

In step A3 (SA3), shared computer 2 receives the "morbidity rate of large-bowel cancer" and "Gno." The received "morbidity rate of large-bowel cancer" and "Gno." are stored in memory section A10 as request information.

In step A4 (SA4), upon the reception of request information, processing program 13 recorded in storage 7 is started to access main DB 14. This processing program 13 performs processing in shared computer 2.

In step A5 (SA5), in accordance with processing program 13, "classification (name of disease)" recorded in main DB 14 is searched and information matching with the requested "morbidity rate of large-bowel cancer" (large-bowel cancer) is extracted.

In step A6 (SA6), from among data recorded in main DB 14, a "polymorphism address" associated with "classification (name of disease)" (large-bowel cancer) that matches with the "morbidity rate of large-bowel cancer" is read out. The read-out "polymorphism address" is stored as positional information associated with request information in memory section A10. Specifically, the "morbidity rate of large-bowel cancer" and "polymorphism address" are recorded in memory section A10 in association with a predetermined "Gno."

In step A7 (SA7), "Gno." and "polymorphism address" recorded in memory section A10 are transmitted to personal computer 3 and instruction information instructing submission of a "polymorphism pattern" corresponding to the transmitted "polymorphism address" is transmitted to personal computer 3. At this time, the submission of additional information such as that concerning anamnesis and characteristics may be optionally instructed depending on the types of request information.

In step A8 (SA8), "Gno.," "polymorphism address," and instruction information transmitted from shared computer 2, are received. The received "Gno." and "polymorphism address" are recorded in memory section 26.

In step A9 (SA9), data II recorded on genome-related information recording medium 24 is accessed in accordance with the received instruction information. In step A10 (SA10), in accordance with processing program 27, data II recorded on genome-related information recording medium 24 is searched, a polymorphism pattern in the instructed polymorphism address is read out, and the polymorphism pattern is then recorded in memory section 26 in association with the polymorphism address. In this case, whether the "Gno." received in step A8 is correct or not is preferably confirmed by accessing data I. In step A10, additional information recorded in data III, data IV, and data V is read out simultaneously with the polymorphism pattern and may be optionally recorded in memory section 26.

In step A11 (SA11), the temporarily-recorded polymorphism pattern associated with the polymorphism address and the optionally-recorded additional information in memory section 26 are output to shared computer 2 together with "Gno." through communication network 1. In step A12 (SA12), shared computer 2 receives the polymorphism pattern associated with the polymorphism address and the optionally-recorded additional information, and the received polymorphism pattern is recorded in memory section A10 in association with the polymorphism address.

In this embodiment, in step A7 shared computer 2 transmits instruction information instructing submission of the "polymorphism pattern", and in step A10 personal computer 3 reads out the polymorphism patterns from genome-related information recording medium 24 in accordance with instruction information. The system, however, may not transmit the instruction information in step A7. In this case, personal computer 3 searches data II in step A10 based on the polymorphism address received in step A8 and reads out polymorphism patterns of the received polymorphism address in accordance with processing program 27. Then, in step A11, personal computer 3 outputs polymorphism patterns and the like to shared computer 2. Also in this case, in step A12 shared computer 2 can obtain the polymorphism pattern of the "polymorphism address" associated with "classification (name of disease)" that matches the "morbidity rate of large-bowel cancer".

In step A13 (SA13), main DB 14 is accessed to search information matching with the received polymorphism address and polymorphism patterns. More specifically, a plurality of polymorphism patterns are recorded in main DB 14 for one polymorphism address. Thus, which polymorphism pattern in main DB 14 matches with the received polymorphism address and the polymorphism pattern thereof is searched.

In step A14 (SA14), the morbidity rate of large-bowel cancer which is associated with the polymorphism pattern matching the received polymorphism pattern is read out in accordance with processing program 13. Specifically, in step A14, the morbidity rate of large-bowel cancer of a requester can be read out in accordance with the polymorphism address and polymorphism pattern submitted by the requester. The read-out morbidity rate is stored in memory section A10 in association with the requester's "Gno." At this time, the morbidity rate of large-bowel cancer may be corrected in accordance with additional information and then stored. Alternatively, other information obtained from additional information may be stored in association with the requester's "Gno." Subsequently, in step A15 (SA15), the requester's "Gno." and morbidity rate, which are stored in memory section A10, are transmitted as semantic information to personal computer 3 through communication network 1. Personal computer 3 receives the requester's "Gno." and morbidity rate (semantic information) in step A16 (SA16). The received semantic information is recorded in memory section 26.

In step A17 (SA17), the morbidity rate of large-bowel cancer is displayed on display device 22 based on semantic information recorded in memory section 26 in accordance with processing program 27. Instead of steps A15 to A17, shared computer 2 can read out (prepare) a screen that displays semantic information in accordance with processing program 13, and display it on display device 22 of personal computer 3 through communication network 1. Also in this case, semantic information is considered to be transmitted from shared computer 2 to personal computer 3. As a result, the requester can obtain the morbidity rate of large-bowel cancer using genome-related information 28 recorded on genome-related information recording medium 24.

As described above, in this system, utilization of genome-related information recording medium 24, which has individuals' polymorphism patterns in association with polymorphism addresses recorded thereon, enables individuals to use semantic information recorded in main DB 14 through the polymorphism addresses. In other words, an individual utilizing this system does not have to record semantic information on a genome-related information recording medium. Instead, the individual can obtain various semantic information simply by possessing genome-related information 28 having the polymorphism pattern associated with the polymorphism address.

More particularly, as described above, semantic information is corrected and increases in the number of types. Thus, by updating main DB 14 the semantic information becomes more accurate and includes a wider range of information. According to this system, individuals can utilize the newest semantic information by updating main DB 14 in line with such increase, correction or the like of semantic information.

Further, utilization of genome-related information recording medium 24 having genome-related information 28 recorded thereon eliminates the need for the user to undergo an examination to obtain genome-related information every time he/she utilizes this system. More specifically, once genome-related information recording medium 24 is produced, thereafter the user can obtain the newest semantic information utilizing this system.

Retention by the user of genome-related information recording medium 24 on which the user's genome-related information 28 has been recorded can prevent apprehension in consigning an external organization to store the user's genome-related information 28 and the risk of leakage of genome-related information 28 through unauthorized access to the organization. On the other hand, when storage of genome-related information recording medium 24 having a plurality of pieces of genome-related information 28 of a plurality of individuals recorded thereon is consigned to an external organization, inefficient handling of genome-related information recording medium 24 or loss of genome-related information recording medium 24 can be prevented, unlike the case where each individual retains their own genome-related information recoding medium 24.

In particular, in accordance with the flow charts shown in FIGS. 6 and 7, all the genome-related information 28 recorded on genome-related information recording medium 24 is not necessarily output through communication network 1, and only the part of genome-related information 28 for which an instruction for the submission was received may be output. According to this system, leakage of highly confidential polymorphism addresses and polymorphism patterns peculiar to individuals can be prevented.

Also, in accordance with the flow charts shown in FIGS. 6 and 7, personal computer 3 does not need to handle information recorded in main DB 14 since shared computer 2 obtains semantic information to provide to the requester. Thus, in accordance with the flow charts shown in FIGS. 6 and 7, desired semantic information can be adequately obtained even if the capacity of personal computer 3 to process information is relatively low. Further, since personal computer 3 does not need to handle information recorded in main DB 14, standardization of processing program 27 in personal computer 3 in compliance with a card drive and the like having genome-related information recording medium 24 mounted thereon is facilitated.

Figure 8:
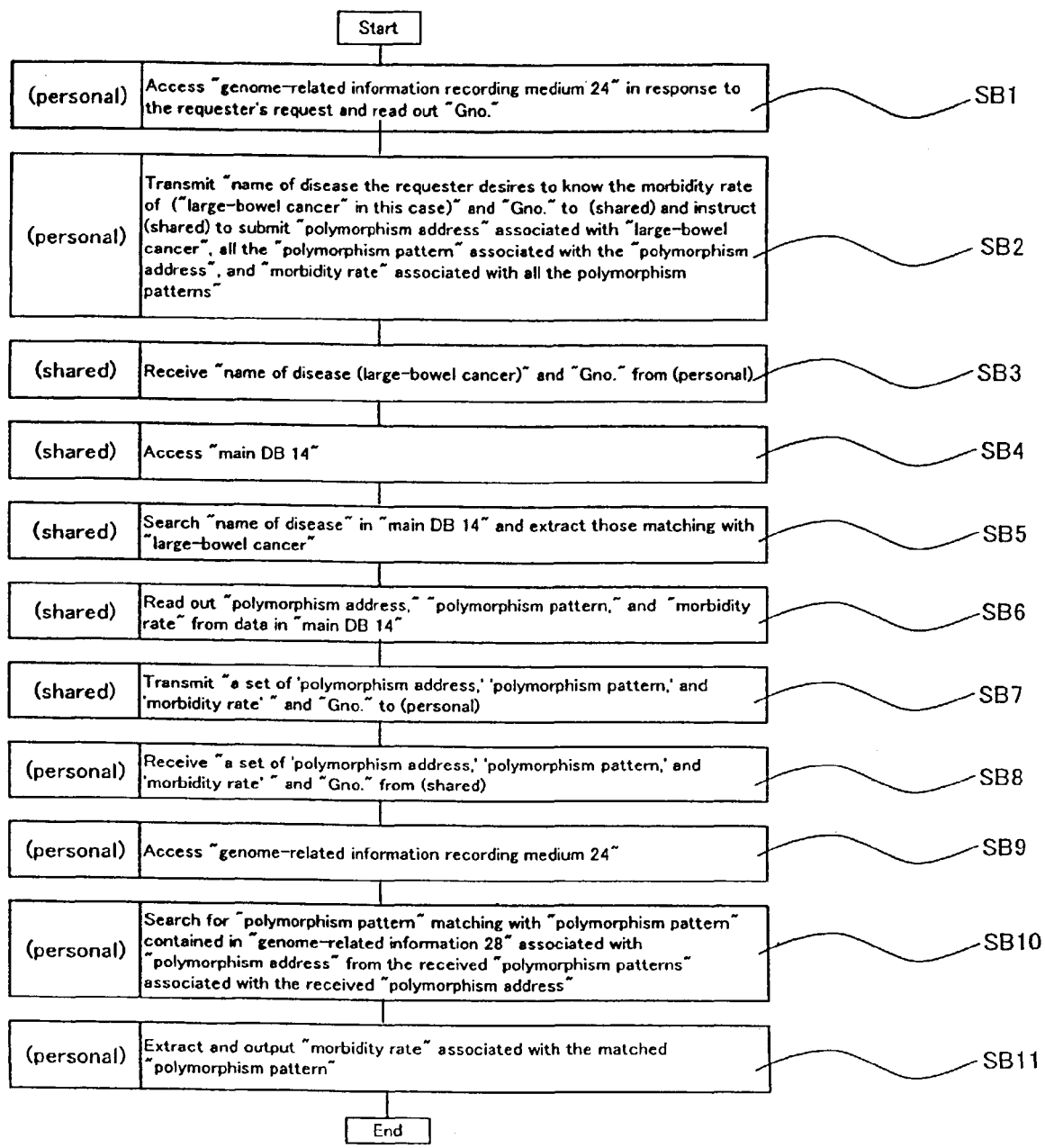
FIG. 8 is a flow chart showing other processing in a shared computer and a personal computer in a system for providing a morbidity rate of a predetermined disease.

In the system for processing information, processing program 13 recorded in storage 7 of shared computer 2 and processing program 27 recorded in storage 23 of personal computer 3 may process information in accordance with, for example, the flow chart shown in FIG. 8. Also in the flow chart shown in FIG. 8, a step described as "(shared)" refers to processing in shared computer 2 and a step described as "(personal)" refers to processing in personal computer 3.

When utilizing the system, the requester first starts processing program 27 recorded in storage 23 in step B1 (SB1). Processing program 27 drives reading apparatus 25 in personal computer 3 and accesses genome-related information recording medium 24, thereby reading out a "Gno." recorded in genome-related information recording medium 24 as data I. The read-out "Gno." is stored in memory section 26.

In step B2 (SB2), based on a screen image displayed by processing program 27 on display device 22, information which the requester wishes to receive, for example, the "morbidity rate of large-bowel cancer" (request information), is input to personal computer 3. At the same time, the "morbidity rate of large-bowel cancer" and "Gno." are transmitted to shared computer 2 from personal computer 3 through communication network 1. Concurrently requested is the submission of "polymorphism address" in which "classification (name of disease)" in main DB 14 is large-bowel cancer, all the "polymorphism patterns" associated with the "polymorphism address," and the "morbidity rate" implied by all the "polymorphism patterns" respectively. More specifically, in step B2, the requester requests information comprising the "polymorphism address" in which "classification (name of disease)" in main DB 14 is large-bowel cancer, all the "polymorphism patterns" associated with the "polymorphism address," and the "morbidity rate" implied by all the "polymorphism patterns" respectively.

In step B3 (SB3), shared computer 2 receives the request information. Shared computer 2 starts processing program 13 upon reception of the request information and, in step B4 (SB4), accesses main DB 14 in accordance with processing program 13.

In step B5 (SB5), in accordance with processing program 13, "classification (name of disease)" recorded in main DB 14 is searched and information matching with the requested "morbidity rate of large-bowel cancer" (large-bowel cancer) is extracted. In step B6 (SB6), main DB 14 is accessed according to processing program 13 to read out the "polymorphism address" associated with "classification (name of disease)" (large-bowel cancer) that matches the "morbidity rate of large-bowel cancer," all the "polymorphism patterns" associated with the polymorphism address, and the "morbidity rate" in all the polymorphism patterns. The read-out "polymorphism address," "polymorphism pattern," and "morbidity rate" are stored in memory section A10 in association with the request information. Specifically, the "polymorphism address," the "polymorphism pattern," and the "morbidity rate" are recorded in memory section A10 for a predetermined "Gno."

In step B7 (SB7), the "Gno." "polymorphism address," "polymorphism pattern," and "morbidity rate" recorded in memory section A10 are transmitted to personal computer 3 through communication network 1. In step B8 (SB8), the "Gno." "polymorphism address," "polymorphism pattern," and "morbidity rate" transmitted from the shared computer 2 are received. The received "Gno." "polymorphism address," "polymorphism pattern," and "morbidity rate" are recorded in memory section 26.

In step B9 (SB9), data II, recorded on genome-related information recording medium 24, is accessed according to processing program 27. In this case, data I, recorded on genome-related information recording medium 24, is also accessed and whether the received "Gno." is correct or not is preferably confirmed.

In step B10 (SB10), the polymorphism pattern in the polymorphism address matching with the received "polymorphism address" is extracted from genome-related information 28 according to processing program 27. In step B10 (SB10), polymorphism pattern matching with the extracted polymorphism pattern is searched from all the received "polymorphism patterns" associated with the received polymorphism address.

In step B11 (SB11), the "morbidity rate" associated with the matching polymorphism pattern among all the received "polymorphism patterns" associated with the received polymorphism address is extracted and the extracted "morbidity rate" is output. This enables the requester to obtain the morbidity rate of large-bowel cancer (semantic information). In step B11, additional information recorded in data III, data IV, and data V is simultaneously read out and the morbidity rate of large-bowel cancer may be corrected by the additional information and then output.

More specifically, in accordance with the flow chart shown in FIG. 8, genome-related information 28 recorded on genome-related information recording medium 24 is output only to personal computer 3 and other than this is not output at all to the outside. That is, genome-related information 28 is transmitted/received only between genome-related information recording medium 24 and personal computer 3. Thus, the system can more accurately prevent leakage of highly confidential genome-related information 28 peculiar to the individual.

Figure 9:
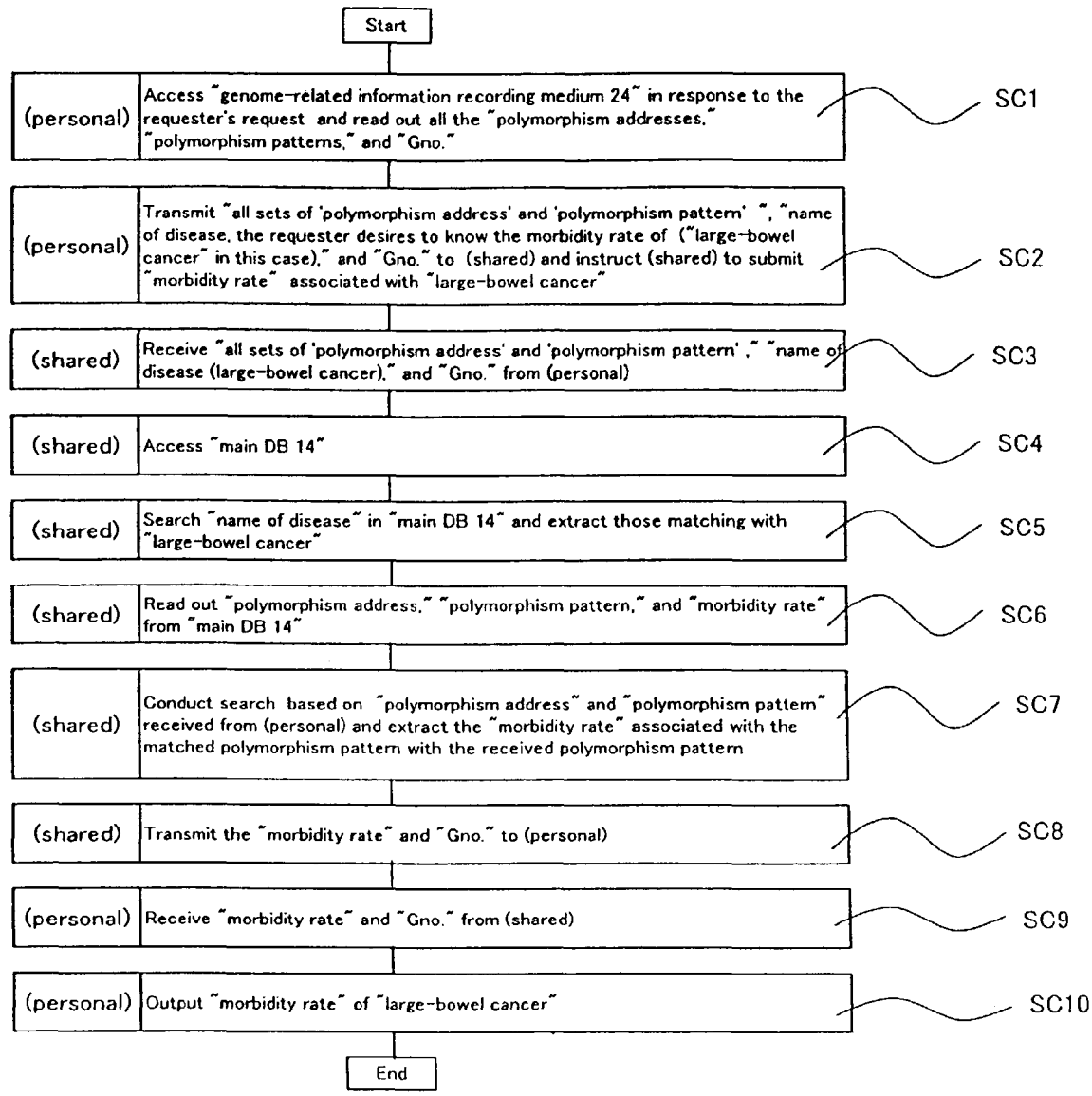
FIG. 9 is a flow chart showing further processing in a shared computer and a personal computer in a system for providing a morbidity rate of a predetermined disease.

In the system for processing information, processing program 13 recorded in storage 7 of shared computer 2 and processing program 27 recorded in storage 23 of personal computer 3 may process information, for example, in accordance with the flow chart shown in FIG. 9. In the flow chart shown in FIG. 9, a step described as "(shared)" refers to processing in shared computer 2 and a step described as "(personal)" refers to processing in personal computer 3.

When utilizing the system, the requester first starts processing program 27 recorded in storage 23 in step C1 (SC1). Processing program 27 drives reading apparatus 25 in personal computer 3 and accesses genome-related information recording medium 24 to read out a "Gno." recorded therein as data I and all "polymorphism addresses" and "polymorphism patterns" recorded therein as data II. The read-out "Gno.", "polymorphism address", and "polymorphism pattern" are stored in memory section 26.

In step C2 (SC2), based on a screen image displayed by processing program 27 on display device 22, information which the requester wishes to receive, for example the "morbidity rate of large-bowel cancer" (request information), is input to personal computer 3. At the same time, the "morbidity rate of large-bowel cancer" and "Gno.", "polymorphism address," and "polymorphism pattern" recorded in memory section 26 are transmitted to shared computer 2 from personal computer 3 through communication network 1.

In step C3 (SC3), shared computer 2 receives "morbidity rate of large-bowel cancer," "Gno.", "polymorphism address," and "polymorphism pattern." The received "morbidity rate of large-bowel cancer" is recorded as request information in memory section A10 and "Gno.", "polymorphism address" and "polymorphism pattern" are also stored in memory section A10. Shared computer 2 starts processing program 13 upon reception of the request information and, in step C4 (SC4), accesses main DB 14 in accordance with processing program 13.

In step C5 (SC5), in accordance with processing program 13, "classification (name of disease)" recorded in main DB 14 is searched and classification matching with the requested "morbidity rate of large-bowel cancer" (large-bowel cancer) is extracted.

In step C6 (SC6), main DB 14 is accessed in accordance with processing program 13 to read out from main DB 14 the "polymorphism address" classified into "large-bowel cancer", all the "polymorphism patterns" associated with the polymorphism address, and the "morbidity rate" in all the polymorphism patterns. The read-out "polymorphism address," "polymorphism pattern," and "morbidity rate" are stored in memory section A10.

In step C7 (SC7), the data stored in memory section A10 in step C6 is searched based on the "polymorphism address" and the "polymorphism pattern" received in step C3, and a morbidity rate associated with polymorphism pattern matching with the received "polymorphism pattern" is extracted from memory section A10.

In step C8 (SC8), the result of step C7, that is, the morbidity rate extracted according to which polymorphism pattern in main DB 14 matches with the polymorphism pattern contained in the received information in step C3, is transmitted to personal computer 3 through communication network 1. In this case, shared computer 2 transmits the extracted morbidity rate together with the requester's "Gno."

In step C9 (SC9), the "Gno." and "morbidity rate (semantic information)" transmitted from shared computer 2 is received. The received "Gno." and "morbidity rate" are recorded in memory section 26. At this time, data I recorded on genome-related information recording medium 24 is accessed and whether the received "Gno." is correct or not can be confirmed.

In step C10 (SC10), in accordance with processing program 27, the morbidity rate of large-bowel cancer is displayed on display device 22 based on semantic information recorded in memory section 26. Instead of steps C8 to C10, shared computer 2 can read out (prepare) a screen that displays semantic information in accordance with processing program 13, and display it on display device 22 of personal computer 3 through communication network 1. Also in this case, semantic information is considered to be transmitted from shared computer 2 to personal computer 3. This enables the requester to obtain the morbidity rate of large-bowel cancer using genome-related information 28 recorded on genome-related information recording medium 24.

More particularly, in accordance with the flow chart shown in FIG. 9, all the genome-related information 28 recorded on genome-related information recording medium 24 is output to shared computer 2 and semantic information to provide to the requester is obtained in shared computer 2. In accordance with the flow chart shown in FIG. 9, even with a relatively small number of times of reception/transmission of information between personal computer 3 and shared computer 2, the requester can obtain semantic information. Therefore, in accordance with the flow chart shown in FIG. 9, even if the information processing capacity of personal computer 3 is relatively low, the desired semantic information can be adequately provided. In addition, the requester can obtain semantic information in a very simple manner.

As described above, according to the system, on genome-related information recording medium 24 and in main DB 14, standardization of only "polymorphism addresses" and the "polymorphism patterns" thereof eliminates the need for standardization of other specific data. Thus, the system can be utilized in a wide range of industries. That is, when providing information using genome-related information recording medium 24, the provider of objects or services can provide information in various manners without the need to standardize semantic information to correspond to the polymorphism pattern or a unified standard such as a method for transmitting/receiving data.

Furthermore, according to the system, a third party or third organization can easily monitor and control shared computer 2 by examining main DB 14. Accordingly, as the system can, for example, execute administrative control over the provider of semantic information, adequate and ethical control over the provider of semantic information can be executed.

Meanwhile, in the system for processing information, a recording medium in which information contained in data II is removed from a genome-related information recording medium, that is, a recording medium having only data I and additionally data III to V, may be used. In this case, information contained in data II is recorded in an external database (genome-related information recording medium) connected to personal computer 3 through communication network 1. In such a system, for example, in above-described step A10, the external database is accessed through communication network 1 and a polymorphism pattern in the instructed polymorphism address is read out, and the polymorphism pattern can be recorded in association with the polymorphism address in memory section 26. Thus, in this system, as with the flow charts shown in FIGS. 6 and 7, 8, and 9, the requester can obtain semantic information.

In the system for processing information, the requester may have a genome-related information recording medium 24 connected to personal computer 3 through communication network 1 instead of the requester him/herself has genome-related information recording medium 24 or a recording medium in which information contained in data II is removed from the genome-related information recording medium. In such a system, the requester can access genome-related information recording medium 24 through communication network 1 to download information such as "polymorphism addresses" and "polymorphism patterns" recorded on genome-related information recording medium 24 into personal computer 3. In this case, genome-related information recording medium 24 may have genome-related information of a plurality of individuals for each individual (each "Gno.") recorded thereon.

In addition, the present invention is not limited to the above-described construction in which shared computer 2 comprises main DB 14, and, for example, is applicable to a system for processing information equipped with main DB 14 connected to shared computer 2 through communication network 1. In this case, shared computer 2 accesses main DB 14 through communication network 1 as shown in the flow charts in FIGS. 6 and 7, 8, or 9. In this case also, according to the system for processing information, the requester can also obtain desired semantic information in accordance with the flow charts shown in FIGS. 6 and 7, 8, or 9.

More specifically, shared computer 2 can access a plurality of main DBs 14 owned by different organizations or groups through communication network 1 and can utilize semantic information contained in these plurality of main DBs 14, thereby providing information to the requester. That is, in the system for processing information, in step A5 in the flow charts shown in FIGS. 6 and 7, in step B5 in the flow chart shown in FIG. 8, or in step C5 in the flow chart shown in FIG. 9, shared computer 2 accesses various main DBs 14 having information on the morbidity rate of large-bowel cancer as semantic information. According to the system for processing information, therefore, the requester can obtain information on the morbidity rate of large-bowel cancer from information contained in various main DBs 14.

In this system, as shown in the flow charts shown in FIGS. 6 and 7, 8, or 9, shared computer 2 may transmit, at least, the request information received from personal computer 3 to a so-called agent and obtain semantic information ("morbidity rate of large-bowel cancer" in this embodiment) through the agent.

2. Second Embodiment

Next, a system for processing information for providing a medicament appropriate for the diathesis, such as regarding responsiveness to a medicament or immunity to substances, is explained as a second embodiment to which the present invention has been applied. Regarding the system for processing information explained as the present embodiment, explanation of the constitution, operation, and terms thereof is omitted by employing the same appellations, symbols, and definitions for the same constitution and terms as with the system for processing information according to the above described first embodiment. The present embodiment is directed to explanation of a system for providing an object (a medicament) in accordance with request information from the user, and thus, is explained as a simple model for the convenience of the explanation. More specifically, semantic information (drug type) and the like, as shown in FIG. 10, is recorded in main DB 14 in the present embodiment.

Figure 12:
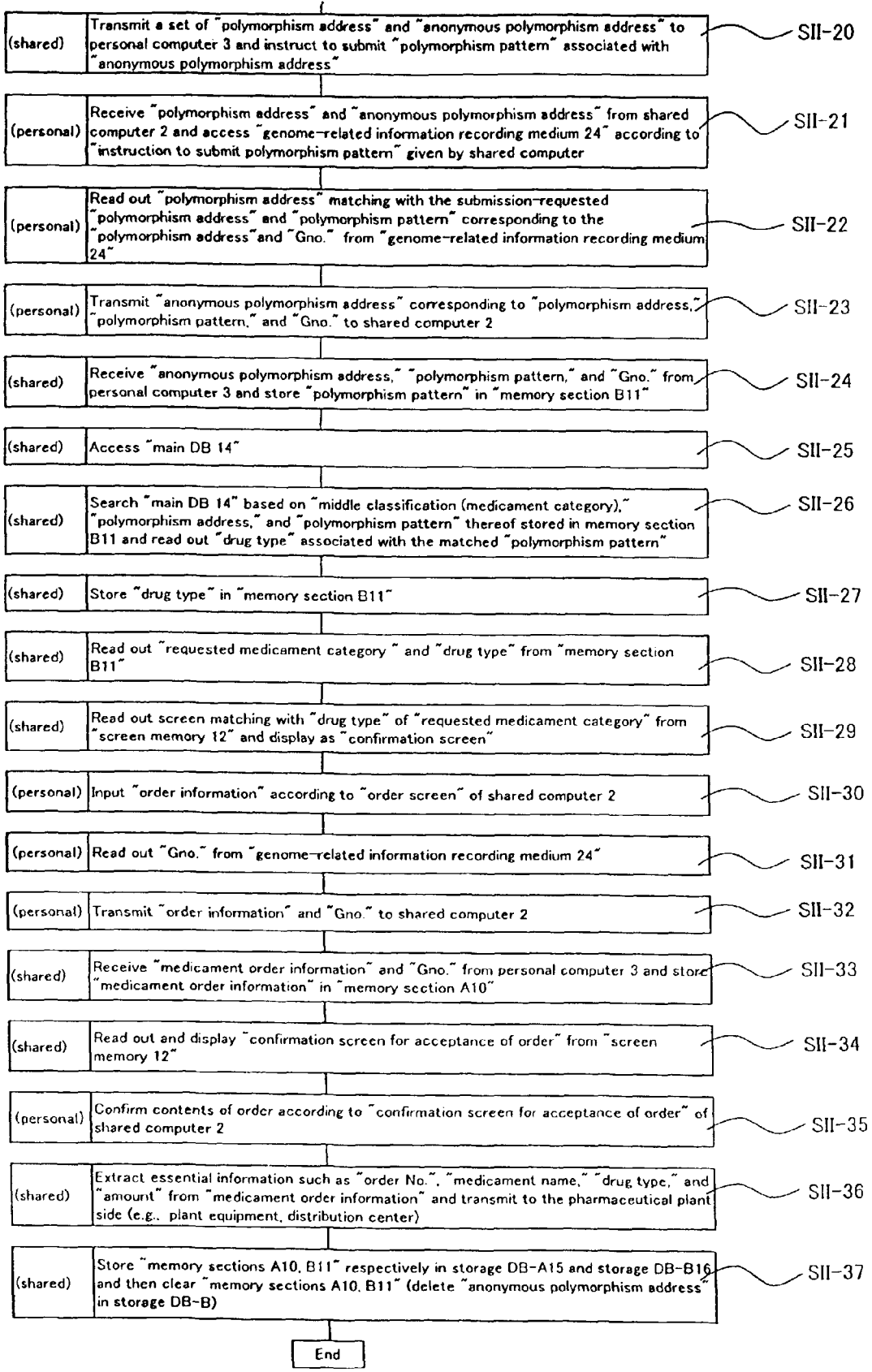
FIG. 12 is a flow chart, which is a continuation of FIG. 11, showing processing in a shared computer and a personal computer in a system for providing a medicament that is appropriate for the diathesis.

The system for processing information for providing a medicament can provide the most suitable medicament to the user, for example, as according to the flow charts shown in FIGS. 11 and 12. In the flow charts shown in FIGS. 11 and 12, a step described as "(shared)" refers to processing in shared computer 2 and a step described as "(personal)" refers to processing in personal computer 3.

In step II-1 (SII-1), the requester first accesses, for example, shared computer 2 of a pharmaceutical company from personal computer 3 through communication network 1. Shared computer 2 of a pharmaceutical company may be, for example, an exclusive computer, a computer for controlling an order for a medicament and information on ordering and shipping, or a computer for controlling production of a desired medicament by controlling a pharmaceutical plant. Shared computer 2 is not limited to those belonging to a pharmaceutical company and it may belong to an agency or institution for providing information, such as a type of drug or number of medicaments to be provided, to a provider of a medicament such as a pharmaceutical company.

Examples of requesters in the present embodiment include individuals possessing genome-related information recording medium 24, medical institutions possessing genome-related information recording medium 24, and medical institutions utilizing genome-related information recording medium 24 possessed by individuals.

Figure 13:
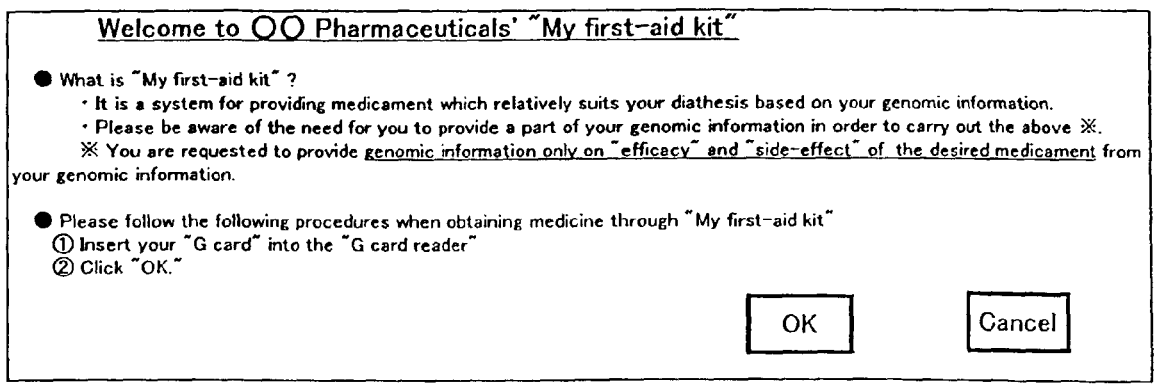
FIG. 13 shows a screen image indicated as an example of a portal screen for a tailor-made non-prescription pharmaceuticals.

In step II-2 (SII-2), in shared computer 2, processing program 13 is started in response to the requester's access and a "portal screen for tailor-made non-prescription pharmaceuticals" is read from screen memory 12 to display on display device 22 of personal computer 3. Examples of the "portal screen for tailor-made non-prescription pharmaceuticals" include a screen image as shown in FIG. 13.

In step II-3 (SII-3), the requester equips genome-related information recording medium 24 into reading apparatus 25 in accordance with an instruction on the "portal screen for tailor-made non-prescription pharmaceuticals" so as to enable access to genome-related information recording medium 24 using personal computer 3. In this case, whether or not the requester is an authorized user of genome-related information recording medium 24 is preferably authenticated. In step II-4 (SII-4), the requester then clicks an "OK" button displayed on the "portal screen for tailor-made non-prescription pharmaceuticals" to transmit one's intent to utilize the system to shared computer 2.

Figure 14:
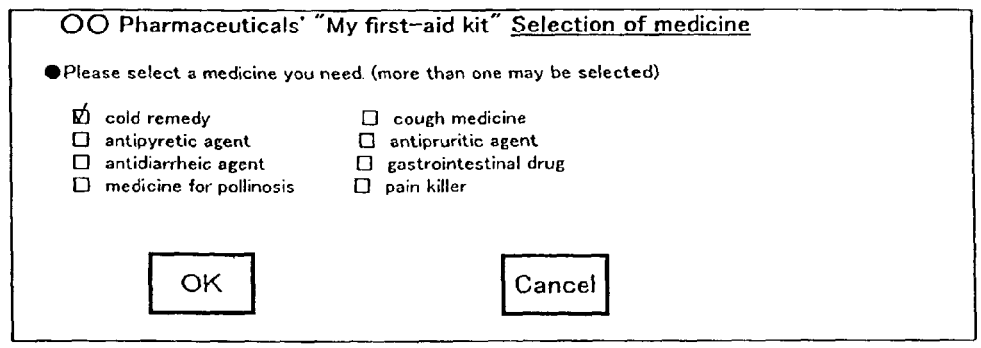
FIG. 14 shows a screen image indicated as an example of a medicament category menu screen.

In step II-5 (SII-5), a "medicament category menu" screen is read from screen memory 12 in shared computer 2 in accordance with processing program 13 and displayed on display device 22 of personal computer 3. Examples of a "medicament category menu" screen include a screen image as shown in FIG. 14.

In step II-6 (SII-6), the requester selects the desired medicament category (medicament) in accordance with the "medicament category menu" screen that has been accessed with personal computer 3.

In step II-7 (SII-7), reading apparatus 25 of personal computer 3 accesses genome-related information recording medium 24 and reads out "Gno." from data I. In step II-8 (SII-8), "Gno." read out in step II-7 and the "medicament category" (request information) selected in step II-6 are transmitted to shared computer 2 through communication network 1.

In step II-9 (SII-9), shared computer 2 receives "Gno." and "medicament category" and the "Gno." and the "medicament category" are stored in memory section A10. In the present embodiment, the "level of disclosure" is associated with semantic information that is recorded in main DB 14. The "level of disclosure" in this embodiment indicates whether or not semantic information and information associated with the semantic information should be disclosed to the user of the information. More specifically, recorded, in association with semantic information, are: "level of disclosure A" designating a level that may be disclosed only when the requester has been authenticated; "level of disclosure B" designating a level that may be disclosed to any requester irrespective of whether the requester has been authenticated or not; and "prohibition against disclosure" designating a level that should not be disclosed to any requester.

Shared computer 2 comprises, for example, a database having "information regarding the authenticated requester such as 'requester No.'" (not shown, hereinafter referred to as "requester information database") previously recorded in database 8.

The requester transmits the "requester No." to shared computer 2 together with "Gno." and request information. When services using semantic information associated with "level of disclosure A" and information associated with the semantic information are to be provided to the requester, shared computer 2 accesses the "requester information database" to judge, based on the received "requester No.", whether or not the requester has been authenticated.

When the requester is judged to be authenticated, shared computer 2 registers "level of disclosure A" in association with the "Gno." received from personal computer 3 in storage 7. In the subsequent step, shared computer 2 searches the "level of disclosure" in main DB 14 based on the registered "level of disclosure A" and provides services using semantic information associated with "level of disclosure A" and information associated with the semantic information to the requester. On the other hand, when the requester is judged to be unauthenticated, shared computer 2 immediately cancels processing or registers "level of disclosure B" in association with the received "Gno." in storage 7. In the subsequent step, shared computer 2 searches the "level of disclosure" in main DB 14 based on the registered "level of disclosure B" and provides services using semantic information associated with "level of disclosure B" and information associated with the semantic information to the requester. Thus, use of the "level of disclosure" enables the determination whether or not the disclosure of semantic information and information associated with the semantic information is approved.

In the present embodiment, because the system is one for providing non-prescription medicaments, the requesters are an unspecified large number of people without the need of previous authentication. This system, therefore, eliminates the need to judge whether or not the requester has been authenticated. For this reason, in step II-9, upon the receipt of request information (medicament category), "level of disclosure B" is automatically selected and registered in strorage 7 in association with the "Gno."

Next, in step II-10 (SII-10), main DB 14 is accessed in accordance with processing program 13. Then, in step II-11 (SII-11), from the polymorphism addresses contained in main DB 14, processing program 13 selects the polymorphism address which matches with the received "medicament category" and for which disclosure is approved by the "level of disclosure," that is, one for which "level of disclosure B" has been set. In this case, as shown in FIG. 10, "major classification," "middle classification," and "minor classification" are recorded in association with one another based on predetermined polymorphism addresses in main DB 14. Among them, the middle classification categorizes the medicament category. Thus, a polymorphism address which matches with the received ("medicament category" can be selected by searching "middle classification" based on the received "medicament category." For example, in the "medicament category menu" in step II-5, when, in addition to a non-prescription medicament, there is a prescription medicament to be provided as an option only to a user with authentication for "level of disclosure A," if a requester without the authentication for "level of disclosure A" requests both the non-prescription medicament and the prescription medicament, the request for the prescription medicament will be denied based on the level of disclosure in main DB 14, and in step II-11, only the polymorphism address associated with the non-prescription medicament is selected.

In step II-12 (SII-12), the selected "polymorphism address" "medicament category" and "Gno." are recorded in memory section B11. At this time, in step II-13 (SII-13), in the system, an "anonymous polymorphism address" (secondary positional information) is set in compliance with a predetermined regulation and the like based on the "polymorphism address" (positional information) which is recorded in memory section B11, and linked to the "polymorphism address" in memory section B11 to record the "anonymous polymorphism address" in memory section B11. This "anonymous polymorphism address" is linked only to the "polymorphism address" selected in step II-11 whereas the "polymorphism address" itself directly represents a position of the polymorphism pattern in a nucleotide sequence. That is, the "anonymous polymorphism address" does not directly represent a position of a polymorphism pattern in a nucleotide sequence. In other words, "the anonymous polymorphism address" is set by allocating, for example, serial numbers, alphabetical characters, or random numbers to the "polymorphism address" selected in step II-11.

Figure 15:
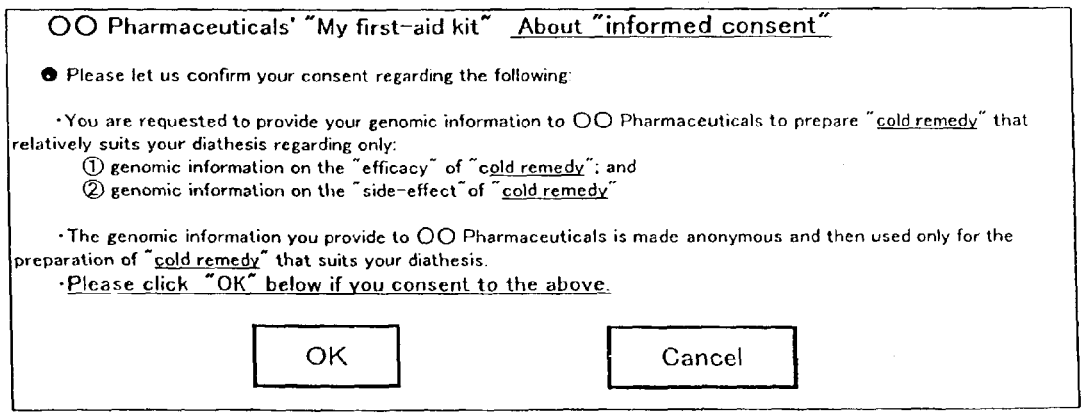
FIG. 15 shows a screen image shown as an example of an input screen for individual IC confirmation.

In step II-14 (SII-14), in accordance with processing program 13, informed consent (hereinafter abbreviated to "IC") concerning the submission of polymorphism patterns is asked of the requester. Specifically, in step II-14 (SII-14), an "input screen for individual IC confirmation" is read from screen memory 12 in accordance with processing program 13 and information on the received "medicament category" is incorporated therein. Then, the "input screen for individual IC confirmation" is displayed on display device 22 of personal computer 3. Examples of an "input screen for individual IC confirmation" include a screen image as shown in FIG. 15.

In step II-15 (SII-15), in accordance with the "input screen for individual IC confirmation" displayed on display device 22 of personal computer 3, the requester inputs their consent for submission of polymorphism patterns. This indicates that the requester has consented to submit polymorphism patterns.

In step II-16 (SII-16), data I on genome-related information recording medium 24 is accessed to read out "Gno." In step II-17 (SII-17), the read-out "Gno." and the "individual IC confirmation" input in step II-15 are transmitted to shared computer 2.

In step II-18 (SII-18), shared computer 2 receives the "Gno." and "individual IC confirmation" transmitted from personal computer 3, and the received "individual IC confirmation" is stored in memory section A10. When storing the "individual IC confirmation," the "individual IC confirmation" is associated with the "Gno." in the data stored in memory section A10 that matches with the received "Gno."

In step II-19 (SII-19), the "polymorphism address" and the "anonymous polymorphism address" stored in steps II-12 and II-13 are read from memory section B11.

In step II-20 (SII-20), the read-out "polymorphism address" is transmitted to personal computer 3 in association with the read-out "anonymous polymorphism address," and instruction information that instructs the submission of the polymorphism pattern corresponding to the "polymorphism address" and the "anonymous polymorphism address" associated with the polymorphism pattern is output to personal computer 3.

In step II-21 (SII-21), the "polymorphism address" and "anonymous polymorphism address" transmitted from shared computer 2 as well as the instruction information are received, and genome-related information recording medium 24 is accessed in accordance with processing program 27. In step II-22 (SII-22), from data II in genome-related information 28, the processing program 27 extracts and reads out the polymorphism address as well as the polymorphism pattern corresponding to the polymorphism address requested by the instruction information, and reads out "Gno." from data I.

In step II-23 (SII-23), the read-out polymorphism pattern is associated with the anonymous polymorphism address set for the polymorphism address of the polymorphism pattern, and these are transmitted together with "Gno." from personal computer 3 to shared computer 2. Specifically, in step II-23, the anonymous polymorphism address, the polymorphism pattern, and the Gno. are transmitted from personal computer 3 to shared computer 2 through communication network 1. In this case, the polymorphism address is not transmitted in association with the polymorphism pattern from personal computer 3. Also, the anonymous polymorphism address does not directly represent a position of the polymorphism pattern in a nucleotide sequence. Thus, even if the content transmitted in step II-23 is leaked externally due to unforeseen circumstances, the position of the polymorphism pattern in the nucleotide sequence cannot be determined.

In step II-24 (SII-24), the anonymous polymorphism address, the polymorphism pattern associated with the anonymous polymorphism address, and "Gno." transmitted from personal computer 3 are received, and the received polymorphism pattern is stored in memory section B11. When storing the "polymorphism pattern," the "polymorphism pattern" is associated with the "Gno." and the "anonymous polymorphism address" in the data stored in memory section B11 that match with the received "Gno." and "anonymous polymorphism address." According to the procedure in step II-24, the "Gno.", the "polymorphism address," the "anonymous polymorphism address" set for each polymorphism address and "polymorphism pattern" are recorded in association with one another in memory section B11.

In step II-25 (SII-25), main DB 14 is accessed in accordance with processing program 13. In step II-26 (SII-26), main DB 14 is searched based on the "middle classification (medicament category)," the "polymorphism address," and the "polymorphism pattern" thereof stored in memory section B11, and the "drug type" associated with the matching polymorphism pattern is read out (see FIG. 10). "Drug type" herein is, in the medicament category classified by the "middle classification" as shown in FIG. 10, semantic information implying information such as a component, a dose, and the like suitable for individuals having predetermined polymorphism patterns. When a plurality of pieces of semantic information is associated with one polymorphism pattern, each piece of semantic information is read out.

In step II-27 (SII-27), the obtained "drug type" is stored in memory section B11 in accordance with processing program 13. In step II-28 (SII-28), the "medicament category" and "drug type" are read from memory section B11 in accordance with processing program 13. In step II-29 (SII-29), a "confirmation screen" corresponding to the read-out "medicament category" and "drug type" is read from screen memory 12 in accordance with processing program 13 and displayed on display device 22 of personal computer 3. Examples of a "confirmation screen" include a screen image as shown in FIG. 16.

In step II-30 (SII-30), the requester clicks an "order screen" button on the "confirmation screen" of personal computer 3 upon confirmation of "name of medicament," "drug type" and the like on the "confirmation screen" to thereby read out the "order screen" (not shown) from screen memory 12 and input order information. Order information includes information for identifying the requester, the quantity with respect to a medicament name falling within the drug type displayed on the order screen, the methods for reception and payment, and the like.

In step II-31 (SII-31), a "Gno." is read from data I of genome-related information 28 by accessing genome-related information recording medium 24 in accordance with processing program 27. In step II-32 (SII-32), the read-out "Gno." and order information input in step II-30 are transmitted to shared computer 2 in accordance with processing program 27.

In step II-33 (SII-33), shared computer 2 receives "Gno." and "order information" transmitted from personal computer 3 and stores the order information in memory section A10. When storing the order information, among the data stored in memory section A10, the "order information" is associated with a "Gno." matching the received "Gno."

In step II-34 (SII-34), a "confirmation screen for acceptance of order" (not shown) is read from screen memory 12 in accordance with processing program 13 to display the "confirmation screen for acceptance of order" on display device 22 of personal computer 3. In step II-35 (SII-35), the requester then confirms the order contents in accordance with the instructions on the "confirmation screen for acceptance of order". The requester, by the above processes, thus completes ordering of a medicament suitable for the individual possessing genome-related information recording medium 24.

Meanwhile, in step II-36 (SII-36), essential information such as "medicament name (information associated with semantic information)," "drug type (semantic information)" and "quantity" is extracted from order information stored in memory section A10 and the extracted information is then transmitted to a provider of medicaments (the user of semantic information and information associated with the semantic information) such as a pharmaceutical plant or distribution center. Essential information refers to information which is required in the production or delivery of medicaments requested by the requester. A provider of medicaments includes a producer of medicaments suitable for the requester through the adjustment of medicament ingredients, component ratio and the like in accordance with the "medicament name" and the "drug type," or a provider of medicaments that provides medicaments by selecting from plural types of medicaments that were previously produced with varying medicament ingredients, component ratios and the like based on the "medicament name" and "drug type". According to the above procedures, the provider of medicaments produces or delivers medicaments suitable for individuals possessing genome-related information recording medium 24.

In shared computer 2, the procedure finally advances to step II-37 (SII-37). In step II-37, the contents stored in memory section A10 and memory section B11 are separately stored in storage DB-A15 and storage DB-B16 respectively. The contents stored in memory section A10 and memory section B11 are then deleted. At this time, the "anonymous polymorphism address" in the content stored in memory section B11 is preferably deleted.

Steps II-34 and II-35 are directed to a final confirmation of the order by the requester, and thus, are not essential in the system. Specifically, the system may proceed in such a manner that step II-33 is followed by step II-36. In this case, the requester completes ordering of medicaments suitable for an individual possessing genome-related information recording medium 24 in step II-32.

According to the flow charts shown in FIGS. 11 and 12, information associated with the semantic information recorded in main DB 14 as the "drug type" can be utilized using genome-related information 28 having individuals' polymorphism patterns in association with polymorphism addresses recorded therein. According to the system, therefore, a medicament suitable for an individual possessing genome-related information recording medium 24 can be obtained based on the diathesis, including responsiveness to a medicament or immunity against substances, of the individual.

More particularly, semantic information is corrected and increases the number of types thereof as described above. Thus by updating main DB 14 the semantic information becomes more accurate and includes a wider range of information. According to this system, individuals can utilize the newest semantic information by updating main DB 14 in line with such increase, correction or the like of semantic information.

In accordance with flow charts such as shown in FIGS. 11 and 12, using the level of disclosure which has been previously recorded in main DB 14, the allowable range of disclosure of semantic information and information associated with the semantic information can be limited depending on the requester. According to the system, therefore, the disclosure of highly confidential semantic information and information associated with the semantic information in response to a request made by an unapproved requester can be prevented. Thus, use of the level of disclosure enables the observation of laws, regulations, behavioral standards of an organization having the shared computer 2 or the like.

Further, in the flow charts as shown in FIGS. 11 and 12, in step II-23 the anonymous polymorphism addresses and polymorphism patterns are transmitted from personal computer 3 to shared computer 2 through communication network 1. In the system, therefore, even if information transmitted in step II-23 was leaked externally due to unforeseen circumstances, the position of the polymorphism pattern in a nucleotide sequence contained in the information cannot be determined. In other words, use of the anonymous polymorphism address in the system can prevent leakage of an individual's information without the use of a highly developed encryption technique. Therefore, the concealment of an individual's information is enhanced in the system since information transmitted in step II-23 is unavailable to others. Furthermore, in the transmission of the information in step II-23, if the information is encrypted in accordance with a commonly performed system, concealment can be further enhanced.

In accordance with the flow charts shown in FIGS. 11 and 12, memory section A10 has the "Gno.", "requested medicament category," "IC confirmation," and "order information" stored therein, as shown in FIG. 17, and memory section B11 has the "Gno.", "requested medicament category," "polymorphism address," "anonymous polymorphism address," "polymorphism pattern," and "drug type" stored therein, as shown in FIG. 18. Linking of the information for identifying the requester and the genetic information of the requester is made complicated by separating memory section A10, which stores the "order information" containing information to identify the requester from memory section B11, which stores the "polymorphism pattern" as genetic information of the requester oneself. This can conceal the correlation between a specific "polymorphism pattern" and information identifying the individual described in the "order information." The specific "polymorphism pattern" is linked to the "order information" through "Gno." and thus they can be associated with each other if necessary.

In the system, information stored in memory section A10 and information stored in memory section B11 are separately stored in storage DB-A15 and storage DB-B16 respectively. Thus, even when the "order information", "polymorphism address" and "polymorphism pattern" of the requester is stored for a long period of time, the correlation between information for identifying the individual described in the "order information" and the "polymorphism address" and "polymorphism pattern" can be concealed according to the system. In this case, therefore, security against information leakage can be further enhanced.

In the system, when transmitting information to the provider of medicaments such as a pharmaceutical plant or a distribution center in step II-36, "Gno." is not contained in the information. Instead, the information preferably comprises, for example, the "order No.", the "medicament name," the "drug type," the "number of tablets," the "number of boxes," and the like, as shown in FIG. 19. In this case, information transmitted to the provider of medicaments contains no "Gno.", and thus the "Gno." cannot be identity from the information. This makes it impossible to specify the individual who possesses the genome-related information recording medium 24 corresponding to the "Gno." In this case, therefore, the "polymorphism pattern" and "order information" of an individual can be surely concealed and the security against information leakage can be further enhanced.

In the above embodiment, the system for processing information for providing medicaments suitable for individuals using polymorphism addresses and polymorphism patterns contained in genome-related information 28 was described. The system, however, is not limited to medicaments but is also applicable to the provision of objects such as foods, cosmetics, or organism-related materials. In this case, for example, as semantic information implied by the polymorphism pattern and information associated with semantic information, a type of substance contained in an object such as food, cosmetics, or organism-related materials is selected using, for example, immunity against substances or responsiveness to medicaments as an index. A suitable object for the individual can be provided by producing or selecting an object in accordance with the type of selected substances and the like.

As described above, according to the system, on genome-related information recording medium 24 and in main DB 14, standardization of only "polymorphism addresses" and the "polymorphism patterns" thereof eliminates the need for standardization of other specific data. Thus, the system can be utilized in a wide range of industries. That is, when providing information using genome-related information recording medium 24, the provider of objects or services can provide information in various manners without the need to standardize semantic information to correspond to the polymorphism pattern or a unified standard such as a method for transmitting/receiving data.

Furthermore, according to the system, a third party or third organization can easily monitor and control shared computer 2 by examining main DB 14. Accordingly, as the system can, for example, execute administrative control over the provider of semantic information, adequate and ethical control over the provider of semantic information can be executed.

3. Third Embodiment

Next, a system for processing information is explained as a third embodiment to which the present invention has been applied, wherein suitable medical examination items are provided to the individual based on the morbidity rate of a predetermined disease.

Regarding the system for processing information explained as the present embodiment, the explanation of its constitution, operation, and terms thereof is omitted by employing the same appellations, symbols, and definitions for the same constitution and terms as with the system for processing information according to the above described the first and the second embodiments. The present embodiment is directed to explanation of a system for providing medical examination items based on request information from the user and, thus, is explained as a simple model for the convenience of explanation.

More specifically, semantic information and the like such as is shown in FIG. 20 is recorded in main DB 14 in the present embodiment. Main DB 14 according to the present embodiment has semantic information that is implied by a polymorphism pattern in association with the polymorphism pattern of a predetermined polymorphism address as "annotative information on the polymorphism pattern." In this "annotative information on the polymorphism pattern," five value levels are set from the highest level "5," which represents a high morbidity rate with respect to a disease classified in the "minor classification," to "1," which represents a low morbidity rate. When indicating the morbidity rate of the predetermined disease by a combination of the polymorphism pattern of the predetermined polymorphism address with a polymorphism pattern of other polymorphism address, a value "Z" is set in "annotative information on the polymorphism pattern" corresponding to the predetermined polymorphism address and a value "Y" is set in "annotative information on the polymorphism pattern." corresponding to the other polymorphism address, In the present embodiment, link DB 30 as shown in FIG. 21 is used, which represents a correspondence between a polymorphism address with the value "Z" being set in "annotative information on the polymorphism pattern" and a polymorphism address where the value "Y," which is to be combined with the polymorphism address with the value "Z," is set. In link DB 30, a possible polymorphism pattern (described as "pattern Z" in FIG. 21) of the polymorphism address with the value "Z" being set (described as "polymorphism address Z" in FIG. 21) is associated with a possible polymorphism pattern (described as "pattern Y" in FIG. 21) of the polymorphism address with the value "Y" being set (described as "polymorphism address Y" in FIG. 21) which is to be combined with the "polymorphism address Z". Further, in link DB 30, the morbidity rate is associated with a combination of "pattern Z" and "pattern Y". Link DB 30 may be stored in database 8 of shared computer 2 or may be provided externally to shared computer 2.

Main DB 14 described in the present embodiment may be controlled by, for example, a public organization or group. In this case, information that is not directly required when selecting medical examination items, which have been classified in a major classification according to, for example, "responsiveness to drug" or "drug side-effect," is also included.

Meanwhile, in the present embodiment genome-related information recording medium 24 on which polymorphism addresses and polymorphism patterns as shown in FIG. 22 are recorded is exemplified and explained. Exemplified in FIG. 22 are a polymorphism address, which corresponds to the polymorphism address exemplified in main DB 14 shown in FIG. 20, and a polymorphism pattern thereof.

Figure 23:
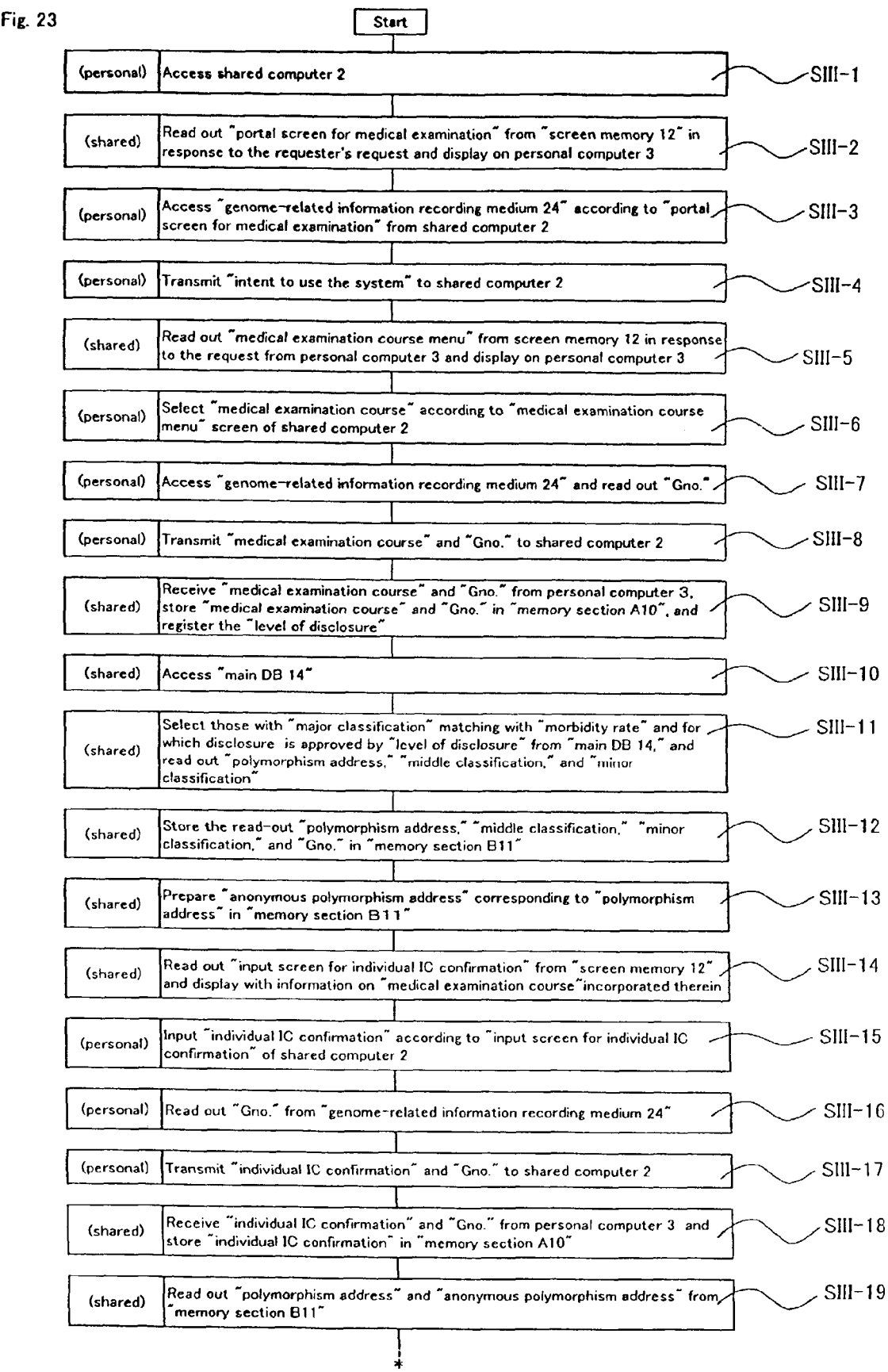
FIG. 23 is a flow chart showing processing in a shared computer and a personal computer in a system for providing medical examination items depending on the diathesis.
Figure 24:
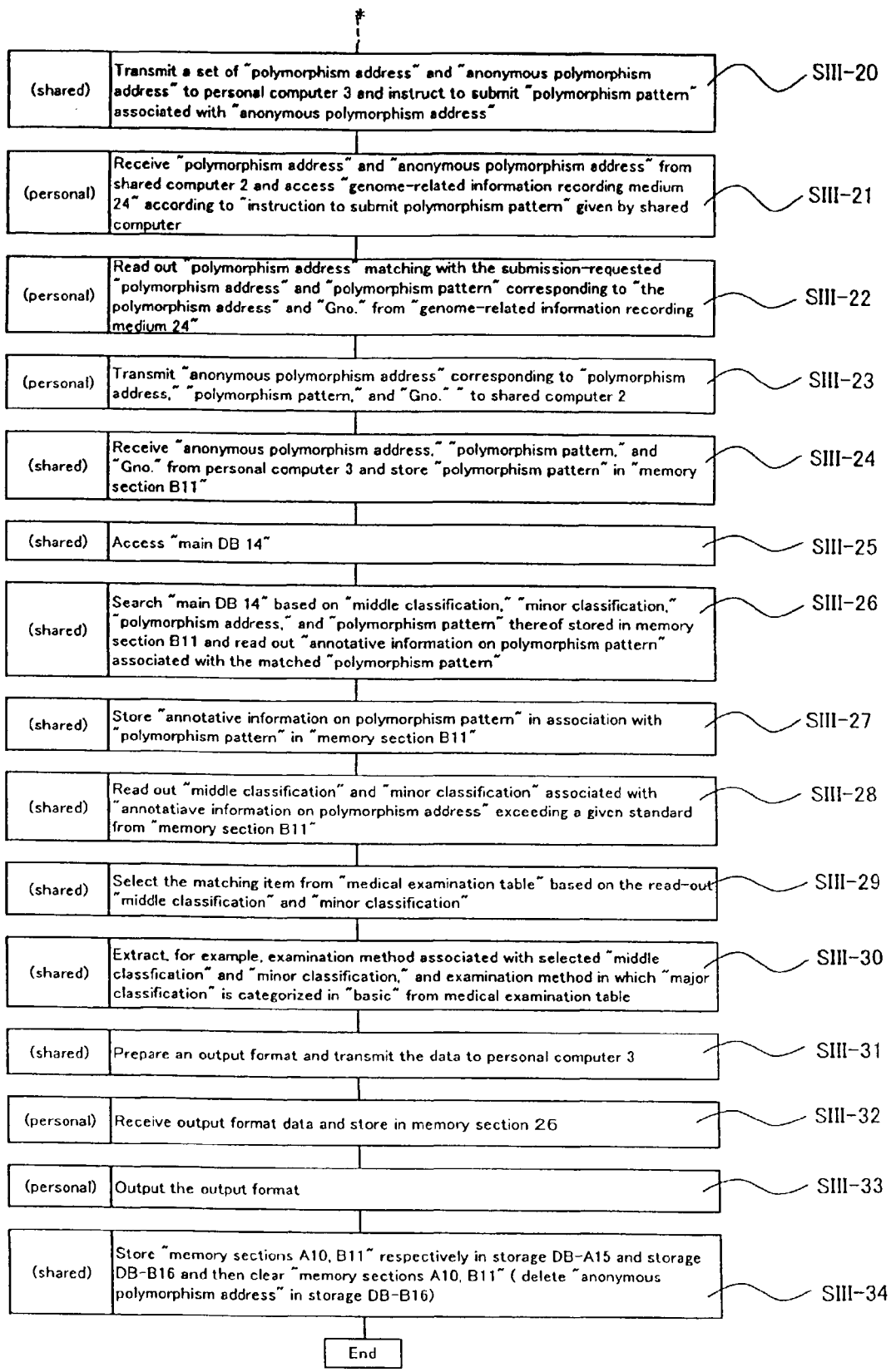
FIG. 24 is a flow chart, which is a continuation of FIG. 23, showing processing in a shared computer and a personal computer in a system for providing medical examination items depending on the diathesis.

According to the system for processing information that provides medical examination items, the most suitable medical examination can be provided to the user in accordance with, for example, the flow charts shown in FIGS. 23 and 24. In the flow charts shown in FIGS. 23 and 24, a step described as "(shared)" refers to processing in shared computer 2 and a step described as "(personal)" refers to processing in personal computer 3.

In step III-1 (SIII-1), the requester first accesses shared computer 2 belonging to, for example, a medical examination center (hereinafter referred to as a "medical center"), from personal computer 3 through communication network 1. Examples of the requester include individuals who possess genome-related information recording medium 24, medical institutions that possess genome-related information recording medium 24, and medical institutions that utilize genome-related information recording medium 24 possessed by individuals.

When individuals possess genome-related information recording medium 24, a card-type recording medium can be exemplified as genome-related information recording medium 24 and the individuals, the medical institutions using genome-related information recording medium 24 of the individuals, or the like utilize the system as the requester. In contrast, when medical institutions possess genome-related information recording medium 24, examples of genome-related information recording medium 24 include a database-type recording medium having a plurality of pieces of genome-related information 28 of a plurality of individuals recorded thereon and the medical institutions utilize the system as the requester.

In the present embodiment, an individual possesses genome-related information recording medium 24 and the individual (the examinee) is the subject of a medical examination, while the medical institution that carries out the medical examination on the examinee is the requester. Thus, personal computer 3 belongs to a medical institution in the following description.

Shared computer 2 may be that of an agent or group for providing desired information on medical examination items and information associated therewith to a requester of information on medical examination items as well as that of a medical center.

Figure 25:
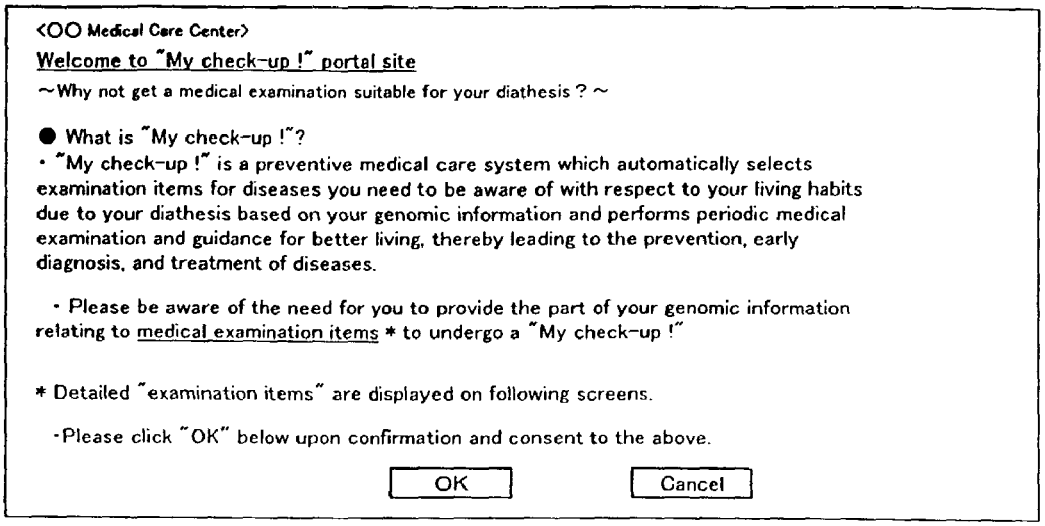
FIG. 25 shows a screen image indicated as an example of a portal screen for medical examination.

In step III-2 (SIII-2), processing program 13 is started upon access by the requester and a "portal screen for medical examination" is read from screen memory 12 in shared computer 2 to display on display device 22 of personal computer 3. Examples of "a portal screen for medical examination" include a screen image as shown in FIG. 25.

In step III-3 (SIII-3), the requester loads genome-related information recording medium 24 into reading apparatus 25 in accordance with instructions on the "portal screen for medical examination," thereby enabling access to genome-related information recording medium 24 using personal computer 3. In this case, whether or not the requester is an authorized user of genome-related information recording medium 24 is preferably confirmed. Thereafter, in step III-4 (SIII-4), the requester clicks an "OK" button displayed on the "portal screen for medical examination" to transmit their intent to utilize the system to shared computer 2.

Figure 26:
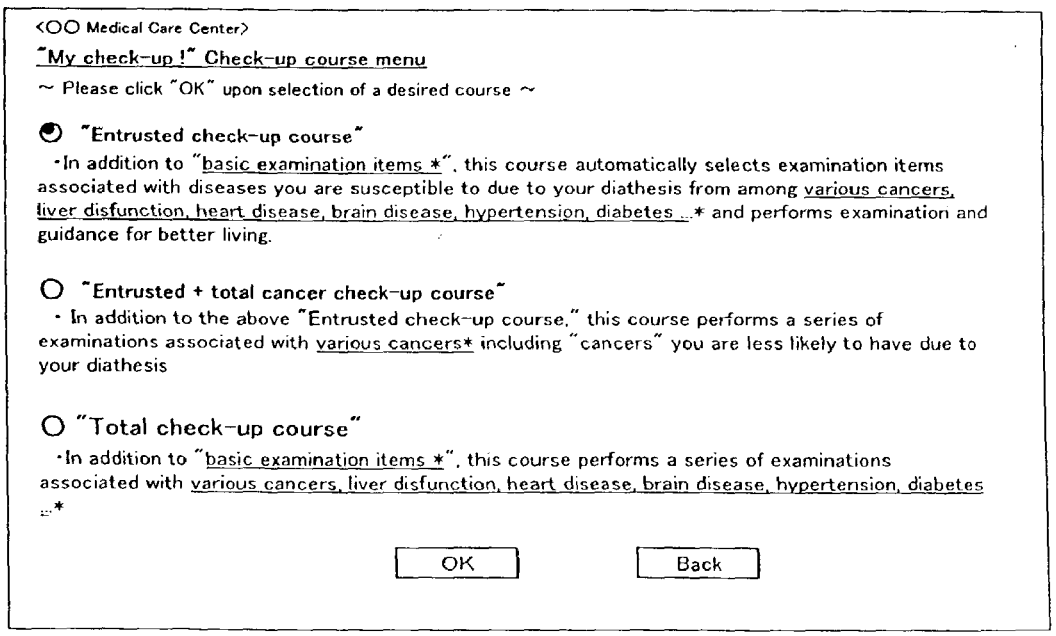
FIG. 26 shows a screen image indicated as an example of a medical examination course menu screen.

In step III-5 (SIII-5), a "medical examination course menu" screen is read from screen memory 12 in accordance with processing program 13 in shared computer 2 and displayed on display device 22 of personal computer 3. Examples of the "medical examination course menu" screen include a screen image as shown in FIG. 26.

In step III-6 (SIII-6), in accordance with the "medical examination course menu" screen to which the requester has accessed with personal computer 3, the requester selects a desired medical examination course for the examinee based on the intent of the examinee. The present embodiment describes the case where an "entrusted check-up course" was selected from among the medical examination courses. The "entrusted check-up course" refers to a course that conducts a medical examination using a combination of examination items that are common for all courses and specific examination items selected according to the medical examinee's diathesis and the like, i.e., examination items to be selected when the morbidity rate of a predetermined disease of the examinee is high.

Shared computer 2 has a "medical examination table" as a database, which has a series of examination items that were used in medical examinations previously accumulated therein. In this "medical examination table," for example, as shown in FIG. 27, "major classification," "middle classification," and "minor classification" are associated with information on the examination method, examinee preparation and the like. "Major classification" categorizes examination items which are common among all medical examination courses as "basic" regardless of the level of morbidity rate, and examination items which are selected when the morbidity rate is high are categorized as "morbidity rate." However, even though an examination item is classified as "basic," it is also classified in the "morbidity rate" category when the morbidity rate is preferably judged prior to the medical examination from the viewpoint of guidance for improvement of living conditions after the medical examination. The "morbidity rate" in "major classification" in the medical examination table corresponds to the "morbidity rate" in "major classification" in main DB 14. Also, "middle classification" and "minor classification" in the medical examination table correspond to "middle classification" and "minor classification," respectively, in main DB 14.

In step III-7 (SIII-7), reading apparatus 25 of personal computer 3 accesses genome-related information recording medium 24 to read out "Gno." from data I. In step III-8 (SIII-8), "Gno." read out in step III-7 and "medical examination course (entrusted check-up course)" (request information), which was selected in step III-6, are transmitted to shared computer 2 through communication network 1.

In step III-9 (SIII-9), shared computer 2 receives the "Gno." and the "medical examination course," and the "Gno." and the "medical examination course" are stored in memory section A10. In the present embodiment, the "level of disclosure" is associated with semantic information that is recorded in main DB 14. The "level of disclosure" in this embodiment indicates whether or not semantic information and information associated with the semantic information should be disclosed to the user of the information. More specifically, recorded, in association with semantic information, are: "level of disclosure A" designating a level that may be disclosed only when the requester has been authenticated; "level of disclosure B" designating a level that may be disclosed to any requester irrespective of whether the requester has been authenticated or not; and "prohibition against disclosure" (not shown in FIG. 20) designating a level that should not be disclosed to any requester.

Shared computer 2 comprises, for example, a database having "information regarding the authenticated requester such as 'requester No.'" (not shown, hereinafter referred to as "requester information database") previously recorded in database 8.

The requester transmits the "requester No." to shared computer 2 together with "Gno." and request information. When services using semantic information associated with "level of disclosure A" and information associated with the semantic information are to be provided to the requester, shared computer 2 accesses the "requester information database" to judge, based on the received "requester No.", whether or not the requester has been authenticated.

When the requester is judged to be authenticated, shared computer 2 registers "level of disclosure A" in association with the "Gno." received from personal computer 3 in strorage 7. In the subsequent step, shared computer 2 searches the "level of disclosure" in main DB 14 based on the registered "level of disclosure A" and provides services using semantic information associated with "level of disclosure A" and information associated with the semantic information to the requester. On the other hand, when the requester is judged to be unauthenticated, shared computer 2 immediately cancels processing or registers "level of disclosure B" in association with the received "Gno." in storage 7. In the subsequent step, shared computer 2 searches the "level of disclosure" in main DB 14 based on the registered "level of disclosure B" and provides services using semantic information associated with "level of disclosure B" and information associated with the semantic information to the requester. Thus, use of the "level of disclosure" enables the determination whether or not the disclosure of semantic information and information associated with the semantic information is approved.

In the present embodiment, because the system is one for providing medical examination items and examinee is an unspecified large number of people, the requesters need not to be authenticated previously. This system, therefore, eliminates the need to judge whether or not the requester has been authenticated. For this reason, in step III-9, upon the receipt of request information (medical examination course), "level of disclosure B" is automatically selected and registered in storage 7 in association with the "Gno." Examples of a case where "level of disclosure A" is selected include the case in which the requester is an authenticated medical institution or the like that intends to obtain all the information necessary for treating a patient (e.g., morbidity rate and responsiveness to medicaments).

Next, in step III-10 (SIII-10), main DB 14 is accessed in accordance with processing program 13. In step III-11 (SIII-11), from main DB 14, processing program 13 selects polymorphism address that is classified as "morbidity rate" in "major classification" and for which "level of disclosure B" has been set, and reads out the "polymorphism address," "middle classification," and "minor classification." More specifically, since "entrusted check-up course" was received as request information in step III-9, examination items should be selected by judging the level of morbidity rate of the predetermined disease of the examinee in advance. In order to comply with the request information, "morbidity rate" classified in the major classification of main DB 14 (i.e. having "morbidity rate" as semantic information) is selected and the "polymorphism address" corresponding thereto is read out. That is to say, the "polymorphism address" corresponding to the request information is read out.

In step III-12 (SIII-12), the "polymorphism address," "middle classification," "minor classification," and "Gno.", which were read-out in accordance with the request information, are recorded in memory section B11. At this time, according to the present system, in step III-13 (SIII-13), an "anonymous polymorphism address" is set for the "polymorphism address" recorded in memory section B11 and linked with the "polymorphism address" in memory section B11, thereby recording the "anonymous polymorphism address" in memory section B11. This "anonymous polymorphism address" is of the same concept as the "anonymous polymorphism address" described in the second embodiment.

In step III-14 (SIII-14), in accordance with processing program 13, informed consent (hereinafter abbreviated to "IC") concerning the submission of genome-related information 28 and the content of semantic information and information associated with the semantic information is asked of the requester. Specifically, in step III-14, an "input screen for individual IC confirmation" is read from screen memory 12 in accordance with processing program 13 and information on the received "medical examination course" is incorporated therein. Then, the "input screen for individual IC confirmation" is displayed on display device 22 of personal computer 3. Examples of the "input screen for individual IC confirmation" include a screen image as shown in FIG. 28.

In step III-15 (SIII-15), in accordance with the "input screen for individual IC confirmation" displayed on display device 22 of personal computer 3, the requester obtains the consent of the examinee regarding the submission of the polymorphism patterns and the content of semantic information and information associated with the semantic information, and inputs the fact that the examinee has consented. This indicates that the examinee has consented to the submission of the polymorphism pattern and the content of semantic information and information associated with the semantic information. The consent to the submission of polymorphism patterns and the content of semantic information and information associated with the semantic information in step III-15 may be carried out by using the "medical examination portal" screen in step III-2 or the "medical examination course menu" screen in step III-5.

In step III-16 (SIII-16), the requester accesses data I of genome-related information recording medium 24 to read out "Gno." In step III-17 (SIII-17), the readout "Gno." and the "individual IC confirmation" input in step III-15 are transmitted to shared computer 2.

In step III-18 (SIII-18), shared computer 2 receives the "Gno." and "individual IC confirmation" transmitted from personal computer 3 and stores the received "individual IC confirmation" in memory section A10. When storing the "individual IC confirmation," among the data stored in memory section A10, "individual IC confirmation" is associated with a "Gno." matching with the received "Gno."

In step III-19 (SIII-19), the "polymorphism address" and the "anonymous polymorphism address," stored in steps III-12 and III-13, are read out from memory section B11. In step III-20 (SIII-20), the read-out "polymorphism address" is transmitted to personal computer 3 in association with the read-out "anonymous polymorphism address" and instruction information that instructs the submission of the polymorphism pattern corresponding to the "polymorphism address" and the "anonymous polymorphism address" associated with the polymorphism pattern is output to personal computer 3.

In step III-21 (SIII-21), the "polymorphism address" and "anonymous polymorphism address" transmitted from shared computer 2 as well as instruction information are received. At the same time, genome-related information recording medium 24 is accessed in accordance with the instruction information. At this time, the received "polymorphism address" and "anonymous polymorphism address" are stored in memory section 26. In step III-22 (SIII-22), in accordance with the instruction information, processing program 27 extracts and reads out the requested polymorphism address and the polymorphism pattern corresponding to the polymorphism address from data II of genome-related information 28, and reads out "Gno." from data I.

In step III-23 (SIII-23), the polymorphism pattern read-out in step III-22 is transmitted in association with the anonymous polymorphism address corresponding to the polymorphism address corresponding to the polymorphism pattern, together with the "Gno." from personal computer 3 to shared computer 2. At this time, personal computer 3 transmits the polymorphism pattern and the anonymous polymorphism address associated with the polymorphism pattern, although personal computer 3 does not transmit any polymorphism address associated with the polymorphism pattern. Since the anonymous polymorphism address does not directly represent a position of the polymorphism pattern in the nucleotide sequence, the position of the polymorphism pattern in the nucleotide sequence cannot be determined even if the contents transmitted in step III-23 are leaked externally due to unforeseen circumstances.

In step III-24 (SIII-24), the anonymous polymorphism address, the polymorphism pattern associated with the anonymous polymorphism address and "Gno." transmitted from personal computer 3 are received and the received polymorphism pattern is stored in memory section B11. When storing the "polymorphism pattern," the "polymorphism pattern" is associated with the "Gno." and "anonymous polymorphism address" in the data stored in memory section B11 that match with the received "Gno." and "anonymous polymorphism address".

In step III-25 (SIII-25), main DB 14 is accessed in accordance with processing program 13. In step III-26 (SIII-26), main DB 14 is searched based on "middle classification," "minor classification," "polymorphism address" and the "polymorphism pattern" thereof stored in memory section B11, and the "annotative information on polymorphism pattern" associated with the matching polymorphism pattern is read out (see FIG. 20). The "annotative information on the polymorphism pattern" herein is semantic information implying the morbidity rate of the disease classified in the "middle classification" and the "minor classification" as shown in FIG. 20. When a plurality of pieces of semantic information is associated with one polymorphism pattern, each piece of semantic information is read out.

The "annotative information on the polymorphism pattern" in the present embodiment includes five levels of values that indicate morbidity rate, a value "Z" that indicates the morbidity rate of a predetermined disease by combining a polymorphism pattern of a predetermined polymorphism address with the polymorphism pattern of an other polymorphism address, and a value "Y" that indicates the other polymorphism address.

In step III-26, when the read-out "annotative information on the polymorphism pattern" is value "Z," processing program 13 accesses link DB 30 shown in FIG. 21. Processing program 13 first searches link DB 30 based on the "polymorphism address" and the "polymorphism pattern" associated with value "Z," and selects the other polymorphism address (polymorphism address Y) to be combined with the "polymorphism address Z." Subsequently, based on the selected polymorphism address Y, the polymorphism pattern (pattern Y) of the polymorphism address Y is read from memory section B11. Link DB 30 is then searched based on the read-out pattern Y of the polymorphism address Y to select the combination corresponded to the pattern Z of the polymorphism address Z and the pattern Y of the polymorphism address Y. The morbidity rate associated with the selected combination is read out from link DB 30.

In step III-27 (SIII-27), in accordance with processing program 13, the obtained "annotative information on the polymorphism pattern," that is, a morbidity rate, is stored in memory section B11 in association with the "polymorphism pattern." Thus, as shown in FIG. 29, "annotative information on the polymorphism pattern" is associated with the "middle classification" and "minor classification" in memory section B11. Thus, for example, a morbidity rate of the disease indicated by "middle classification" and "minor classification" is associated. In memory section A10, "Gno.", "name of medical examination course," and "IC confirmation" are stored in association with one another as shown in FIG. 30.

In step III-28 (SIII-28), in accordance with processing program 13, among the items in "middle classification," "minor classification," and "annotative information on the polymorphism pattern" stored in memory section B11, those items in which morbidity rate exceeds a given level are read out. For example, "middle classification" and "minor classification" items for which the value for morbidity rate in the "annotative information on polymorphism pattern" is at least "4" with respect to the five levels, are read out.

In step III-29 (SIII-29), a medical examination table (FIG. 27) is searched based on the read-out "middle classification" and the "minor classification," and those items corresponded to the read-out "middle classification" and the "minor classification" are selected.

In step III-30 (SIII-30), essential items are extracted from the medical examination table. More specifically, examination methods, examination items, examinee preparation, inquiry items and the like, for the "middle classification" and the "minor classification" selected in step III-29, are read out. Further, examination methods, examination items, examinee preparation, inquiry items, and the like, which are items classified into "basic" by the "major classification" in the medical examination table, are also read out.

In step III-31 (SIII-31), an output format as shown in, for example, FIG. 31 is prepared based on the examination methods, examination items, examinee preparation, inquiry items and the like, which were extracted in step III-30, and the output format data is transmitted to personal computer 3. The output format includes examination items that are common among all medical examination courses (classified into "basic" by the major classification in the medical examination table) and specific examination items concerning a disease for which the morbidity rate exceeds a given level (classified into "morbidity rate" by the major classification in the medical examination table). The examination items concerning diseases for which the morbidity rate exceeds a given level are "information associated with semantic information" induced from semantic information (morbidity rate).

This output format is used in a medical institution conducting the medical examination on the examinee. On the other hand, an output format for an examinee receiving a medical examination on which the examination classification and the examinee preparation are displayed, may be output. In this case, information such as the method and purpose of the examination from which the examinee can ascertain his or her own morbidity rate is not disclosed to the examinee. Thus, the imparting of anxiety to the examinee can be prevented. Also in this case, a medical institution conducting the medical examination can suitably select examining methods for the disease in such a manner that, for example, the examinee would not know what disease is subject of examination.

In step III-31, the output format may be directly transmitted to the examinee instead of being transmitted to a medical institution conducting the medical examination. In this case, the output format transmitted to the examinee does not preferably contain any information that would impart anxiety to the examinee, such as a morbidity rate of a predetermined disease. However, information that may impart anxiety to the examinee can be disclosed in accordance with IC.

In step III-32 (SIII-32), personal computer 3 receives the output format data that was output by shared computer 2 and stores it in memory section 26. Then, in step III-33 (SIII-33), by outputting the output format, the requester can obtain information on medical examination items including specific examination items that are appropriate for the diathesis of the individual possessing genome-related information recording medium 24.

In shared computer 2, in step III-34 (SIII-34) subsequent to step III-31, the contents stored in memory section A10 and memory section B11 are separately stored in storage DB-A15 and storage DB-B16, respectively, and the contents stored in memory section A10 and memory section B11 may then be deleted. At this time, the "anonymous polymorphism address" among the contents stored in memory section B11 is preferably deleted.

As described above, with this system, by following the flow charts shown in FIGS. 23 and 24, the requester can obtain information on medical examination items based on the individual's (the examinee's) diathesis and the like. The column for "category" on the output format shown in FIG. 31 includes "basic," which implies examination items that are common among predetermined medical examination courses, and "specific," which implies examination items for diseases having a high morbidity rate that were obtained in step III-29. Through utilization of this system, medical examination services including "specific" examination items that are appropriate for the individual can be provided.

Further, in the system, even when semantic information is associated with a combination of polymorphism patterns in a plurality of polymorphism addresses, using link DB 30, semantic information which is specific to the individual possessing genome-related information recording medium 24 can be obtained.

In the system, the output format may be prepared by constructing a database in which additional information regarding the medical examinees, such as the results of past medical examination, has been accumulated as a history, reading the history of the results of past medical examination of the examinee from the database, and associating the history with the "annotative information on the polymorphism pattern" and information associated therewith. This database may be provided in shared computer 2 or may be provided in personal computer 3 or genome-related information recording medium 24. According to the system, the output format shows the history of the results of medical examination of the examinee, and thus, comparison with the results of medical examination thereafter enables the provision of enhanced medical examination services. The results of medical examination, for example, include the presence or absence of oxidative damage in genes or gene expression found by genetic testing in addition to the results of conventional medical examination. Further, in the system, in step III-9, as request information in addition to the desired "medical examination course," for example, a request for "functional food that prevents diseases in respect of which the morbidity rate of the examinee is high" is received, and the requested functional food can be provided together with information on medical examination items based on the examinee's diathesis.

In the present embodiment, the system for providing medical examination services including examination items that are "specific" for the examinee in which the requester utilizes a medical center having main DB 14 was described although the system is not limited thereto. The system may comprise personal computer 3 belonging to the examinee who handles genome-related information 28, a medical center having a database in which polymorphism addresses are recorded in a manner capable of corresponding to the request information, and organizations or groups other than the medical center having main DB 14. The examinee may be the requester in the system for processing information. In this case, the examinee accesses the medical center to request the medical examination services, and the medical center accesses main DB 14 of the other organization, to provide medical examination services containing "specific" examination items appropriate for the examinee (requester). More particularly, the other organization having main DB 14 provides semantic information and information associated with semantic information without handling genome-related information 28 and the medical center handles genome-related information 28 without possessing main DB 14. In this case, main DB 14 of the other organization can be utilized in a plurality of medical centers. Further, the other organization performs control, updating, or the like of main DB 14 and the medical center handles genome-related information 28 of the requester. This enables the requester to receive the medical services through the medical center. In this case, medical examination items, which contain the "specific" examination items appropriate for the examinee are transmitted to the examinee through the medical center. However, it may not be limited to this and the medical examination items may be directly transmitted from the other organization to the examinee. Alternatively, the medical examination items may be transmitted to the third organization actually conducting the medical examination from the other organization.

As described above, according to the system, on genome-related information recording medium 24 and in main DB 14, standardization of only "polymorphism addresses" and the "polymorphism patterns" thereof eliminates the need for standardization of other specific data. Thus, the system can be utilized in a wide range of industries. That is, when providing information using genome-related information recording medium 24, the provider of objects or services can provide information in various manners without the need to standardize semantic information to correspond to the polymorphism pattern or a unified standard such as a method for transmitting/receiving data.

Furthermore, according to the system, a third party or third organization can easily monitor and control shared computer 2 by examining main DB 14. Accordingly, as the system can, for example, execute administrative control over the provider of semantic information, adequate and ethical control over the provider of semantic information can be executed.

4. Fourth Embodiment

Next, a system for donor registration for registering an individuals' own polymorphism pattern based on solicitation for a predetermined purpose, and a system for processing information that provides information on other individual organisms having properties compatible with a "given property" of the requester in relation to the predetermined purpose are described as the fourth embodiment to which the present invention has been applied. For the convenience of explanation, it is described as a simple model.

Regarding the system for processing information explained as the present embodiment, the explanation of its constitution, operation, and terms thereof is omitted by employing the same appellations, symbols, and definitions for the same constitution and terms as with the system for processing information according to the above described the first, the second and the third embodiments. More particularly, semantic information (an individual property type, a compatible type) or the like as shown in FIG. 32 is recorded in main DB 14 according to the present embodiment. In main DB 14, the "polymorphism address" and the "polymorphism pattern" in the polymorphism address are recorded in association with each other depending on the "classification" for categorizing a predetermined property. In main DB 14 is also recorded an "individual property type" implied by a predetermined "polymorphism pattern" (information on a predetermined individual organism) and a "compatible type" indicating a compatible type with the "individual property type" (information on an other individual organism) as semantic information. The "level of disclosure" defining whether information on the "individual property type" and the "compatible type" in the predetermined polymorphism address can be disclosed or not may be further recorded in main DB 14 in association with this information.

More specifically, polymorphism addresses "1000" and "2000" are associated with the "given property," and the individual property type implied by a possible combination of polymorphism patterns in these polymorphism addresses is recorded as "a" and "b." The compatible types of these individual property types "a" and "b" are recorded as "b" and "a," respectively. That is to say, FIG. 32 demonstrates that, for example, when polymorphism patterns in polymorphism addresses "1000" and "2000" are respectively "A" and "C," the individual property type regarding the "given property" is "a," and the compatible type that is compatible to individual property type "a" is "b."

The present embodiment is explained by using genome-related information recording medium 24 having polymorphism addresses and polymorphism patterns as shown in FIG. 33 recorded thereon as an example. Exemplified in FIG. 33 is genome-related information recording medium 24 containing polymorphism addresses and polymorphism patterns thereof corresponding to the polymorphism addresses ("1000" and "2000") exemplified in main DB 14 in FIG. 32.

Figure 34:
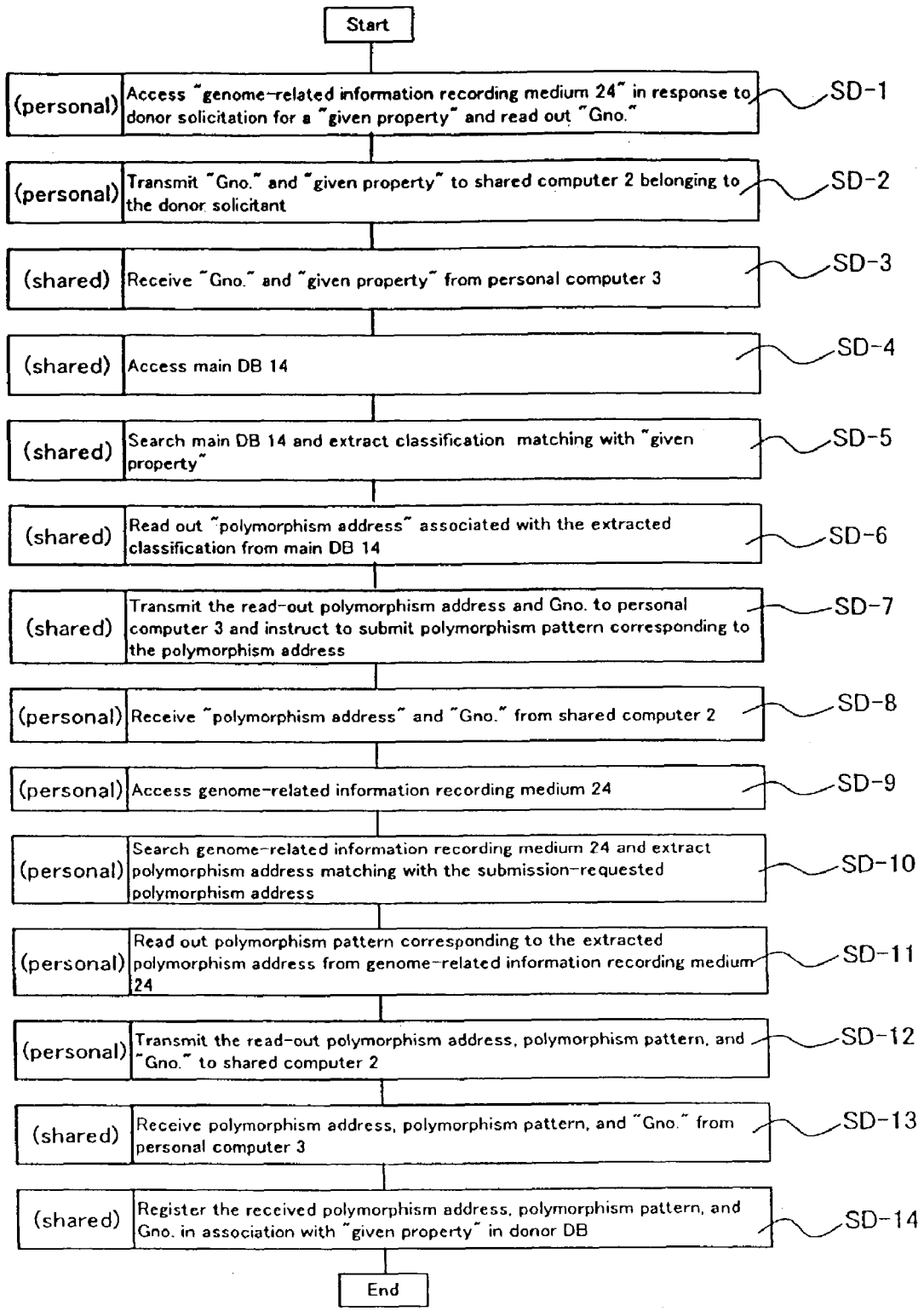
FIG. 34 is a flow chart showing processing in a shared computer and a personal computer in a system for donor registration for registering an individual's own polymorphism pattern.

First, a system for donor registration for registering an individual's own polymorphism pattern based on solicitation for a predetermined purpose is explained. In the system for donor registration, for example, as in accordance with the flow chart shown in FIG. 34, a donor database (hereinafter referred to as a "donor DB") for a predetermined purpose such as shown in FIG. 35 can be constructed. In the flow chart shown in FIG. 34, a step described as "(shared)" refers to processing in shared computer 2 and a step described as "(personal)" refers to processing in personal computer 3.

In the system, processing program 27, which is recorded in storage 23 of personal computer 3, is first started based on solicitation for donors in step D-1 (SD-1). In step D-1, processing program 27 drives reading apparatus 25 of personal computer 3 and accesses genome-related information recording medium 24 to read out a "Gno." recorded thereon as data I. The read-out "Gno." is stored in memory section 26.

In step D-2 (SD-2), the read-out "Gno." is transmitted together with a "given property," which is registration-request information, through communication network 1 to shared computer 2 belonging to the party soliciting donors. This enables declaration of intention (i.e., request for services) to register as a donor for the "given property," using the system.

At this time, strict enforcement of obtainment of informed consent (hereinafter abbreviated to "IC") is preferably conducted regarding the purpose of donor registration and its content and the method and range of utilization thereof.

In step D-3 (SD-3), shared computer 2 receives the "Gno." and "given property" transmitted from personal computer 3. After reception of the "Gno." and "given property," shared computer 2 starts processing program 13. The received "Gno." and "given property" are stored in memory section A10.

In step D-4 (SD-4), main DB 14 is accessed in accordance with processing program 13. In step D-5 (SD-5), main DB 14 is searched based on the "given property" as request information in accordance with processing program 13 to extract the classification corresponded to the "given property."

In step D-6 (SD-6), the "polymorphism address" associated with the extracted "given property" is read from main DB 14 in accordance with processing program 13. The read-out "polymorphism address" is stored in memory section A10.

In step D-7 (SD-7), "Gno." and "polymorphism address" stored in memory section A10 are read out in accordance with processing program 13, "Gno." and "polymorphism address" are transmitted to personal computer 3, and instruction information instructing submission of the "polymorphism pattern" corresponding to the transmitted "polymorphism address" is transmitted to personal computer 3. In this case, the submission of additional information such as anamnesis and characteristics may be optionally instructed within a range regulated by the IC.

In step D-8 (SD-8), the "Gno." and "polymorphism address" transmitted from shared computer 2 are received. The received "Gno." and "polymorphism address" are recorded in memory section 26. In step D-9 (SD-9), data II which is recorded on genome-related information recording medium 24 is accessed in accordance with the received instruction information ("Gno." and "polymorphism address").

In step D-10 (SD-10), data II on genome-related information recording medium 24 is searched to extract the instructed polymorphism address. In step D-11 (SD-11), data II on genome-related information recording medium 24 is searched in accordance with the extracted polymorphism address to read out the corresponding polymorphism pattern. The read-out polymorphism pattern is recorded in association with the polymorphism address in memory section 26. At this time, data I is preferably accessed to confirm whether the "Gno." contained in instruction information is correct or not. In step D-10, additional information recorded in data III, data IV, and data V may be simultaneously read out in addition to the polymorphism pattern to record in memory section 26 if necessary.

In step D-12 (SD-12), the temporarily-recorded polymorphism pattern associated with the polymorphism address and the optionally-recorded additional information in memory section 26 are output to shared computer 2 through communication network 1 together with the "Gno." In step D-13 (SD-13), shared computer 2 receives the polymorphism pattern associated with the polymorphism address, the Gno., and the optionally-recorded additional information. The received polymorphism pattern is recorded in memory section A10 in association with the polymorphism address.

In step D-14 (SD-14), the polymorphism pattern and the Gno., which are recorded in memory section A10, and additional information are associated with the "given property" and then registered in the donor DB as shown in FIG. 35. In this donor DB, the polymorphism address associated with a given property and the polymorphism pattern of the polymorphism address are recorded for each "Gno."

A donor DB is provided in, for example, database 8 (memory) of shared computer 2 although it is not limited thereto. For example, a donor DB may be provided in a memory external to shared computer 2.

As described above, donor registration can be very easily carried out according to the system without the necessity to conduct any examination, investigation, or test when soliciting for the predetermined purpose. In particular, in the system, when performing donor registration in accordance with the flow chart shown in FIG. 34, all of genome-related information 28 which has been recorded on genome-related information recording medium 24 is not necessarily output through communication network 1. Instead, only the part of genome-related information 28 for which submission has been instructed may be output. According to the system, therefore, donor registration can be carried out while preventing leakage of highly confidential polymorphism addresses and polymorphism patterns that are peculiar to individuals. Also in the system, use of the "anonymous polymorphism address" can further prevent leakage of polymorphism addresses and polymorphism patterns.

Meanwhile, in the system, a donor DB may comprise a polymorphism address and a polymorphism pattern associated with the "given property" as well as semantic information implied by the polymorphism pattern recorded therein. More specifically, the "individual property type" and the "compatible type," which are recorded in main DB 14, may be recorded in the donor DB in association with the "Gno." or "polymorphism pattern."

Next, a system for processing information that provides information on other individual organisms having properties compatible with the "given property" of the requester (referred to as a "recipient" in the present embodiment) for a predetermined purpose is described. This system for processing information utilizes main DB 14 shown in FIG. 32 and the donor DB shown in FIG. 35 and can provide information on other individual organisms in accordance with, for example, the flow charts shown in FIGS. 36 and 37. In the flow charts shown in FIGS. 36 and 37, a step described as "(shared)" refers to processing in shared computer 2 and a step described as "(personal)" refers to processing in personal computer 3.

In the system, a recipient first starts processing program 27 recorded in storage 23 of personal computer 3 in step R-1 (SR-1) in order to obtain information on other individual organisms that is compatible with the recipient's "given property." In step R-1, processing program 27 drives reading apparatus 25 of personal computer 3 and accesses genome-related information recording medium 24 to read out a "Gno." recorded as data I on genome-related information recording medium 24. The read-out "Gno." is stored in memory section 26.

In step R-2 (SR-2), the read-out "Gno." and the "given property" that are the request information are transmitted through communication network 1 to shared computer 2 of the provider of information. This enables declaration of intention to request information on other individual organisms which are compatible with respect to the "given property," utilizing the system. At this time, strict enforcement of obtainment of IC is preferably conducted regarding acceptable use regulations for information on the polymorphism pattern and the compatible other individual organisms.

In step R-3 (SR-3), shared computer 2 receives the "Gno." and "given property" transmitted from personal computer 3. After reception of the "Gno." and "given property," shared computer 2 starts processing program 13. The received "Gno." and "given property" are stored in memory section A10.

In step R-4 (SR-4), main DB 14 is accessed in accordance with processing program 13. In step R-5 (SR-5), main DB 14 is searched in accordance with processing program 13 and based on the "given property," and the classification matching with the "given property" is extracted.

In step R-6 (SR-6), the "polymorphism address" associated with the extracted classification "given property" is read from main DB 14 in accordance with processing program 13. The read-out "polymorphism address" is stored in memory section A10. More specifically, in the case of main DB 14 shown in FIG. 32, "1000" and "2000" are extracted and stored as polymorphism addresses associated with the "given property."

In step R-7 (SR-7), "Gno." and "polymorphism address" stored in memory section A10 are read out in accordance with processing program 13, the "Gno." and the "polymorphism address" are transmitted to personal computer 3, and instruction information instructing the submission of the "polymorphism pattern" corresponding to the transmitted "polymorphism address" is transmitted to personal computer 3. At this time, the submission of additional information such as anamnesis and characteristics may be optionally instructed within a range regulated by IC.

In step R-8 (SR-8), personal computer 3 receives the "Gno." and the "polymorphism address" transmitted from shared computer 2. The received "Gno." and "polymorphism address" are recorded in memory section 26. In step R-9 (SR-9), data II recorded on genome-related information recording medium 24 is accessed in accordance with the received instruction information ("Gno." and "polymorphism address").

In step R-10 (SR-10), data II on genome-related information recording medium 24 is searched and the instructed polymorphism address is extracted. In step R-11 (SR-11), data II on genome-related information recording medium 24 is searched based on the extracted polymorphism address to read out the corresponding polymorphism pattern. The read-out polymorphism pattern is recorded in memory section 26 in association with the polymorphism address. In this case, data I is preferably accessed to confirm whether the "Gno." contained in the instruction information is correct or not. Also, in step R-10, additional information recorded in data III, data IV and data V is simultaneously read out in addition to the polymorphism pattern and it may be recorded in memory section 26 if necessary. More specifically, in the case of genome-related information recording medium 24 shown in FIG. 33, polymorphism patterns "A (corresponding to polymorphism address 1000)" and "C (corresponding to polymorphism address 2000)" are read out in compliance with the instructed polymorphism address.

In step R-12 (SR-12), the temporarily-recorded polymorphism pattern associated with the polymorphism address and the optionally-recorded additional information in memory section 26 are output to shared computer 2 through communication network 1 together with the "Gno." In step R-13 (SR-13), shared computer 2 receives the polymorphism pattern associated with the polymorphism address, the Gno., and the optionally-recorded additional information. The received polymorphism pattern is recorded in memory section A10 in association with the polymorphism address. More specifically, polymorphism pattern "A" corresponding to polymorphism address "1000" and polymorphism pattern "C" corresponding to polymorphism address "2000" are recorded in memory section A10.

In step R-14 (SR-14), main DB 14 is accessed in accordance with processing program 13. In step R-15 (SR-15), main DB 14 is searched based on the received polymorphism address and the polymorphism pattern thereof to extract the "individual property type" associated with the matched polymorphism pattern (information on the predetermined individual organisms). Specifically, in the case of FIG. 32, the individual property type "a" is extracted for the combination in which the polymorphism patterns of polymorphism addresses "1000" and "2000" are "A" and "C" respectively.

In step R-16 (SR-16), main DB 14 is searched based on the "individual property type" extracted in step R-15, and the "compatible type" being compatible to the "individual property type" (information on other individual organisms) is extracted. More specifically, in the case of FIG. 32, since the individual property type is "a," "b" is extracted as the compatible type for the individual property type "a."

In step R-17 (SR-17), main DB 14 is searched based on the extracted compatible type, and an individual property type which is the same as the compatible type is searched. The polymorphism pattern, associated with the searched individual property type, and the polymorphism address thereof are read out. Specifically, in the case of FIG. 32, since the extracted compatible type is "b," the polymorphism pattern having "b" as the individual property type and the polymorphism address thereof are read out. That is, in the case of FIG. 32, a combination in which the polymorphism pattern of polymorphism address "1000" is "G" and the polymorphism pattern of polymorphism address "2000" is "C" and a combination in which the polymorphism pattern of polymorphism address "1000" is "A" and the polymorphism pattern of polymorphism address "2000" is "T" are read out.

In step R-18 (SR-18), a donor DB is accessed in accordance with processing program 13. The donor DB (for example, as shown in FIG. 35) is constructed as described above and polymorphism addresses and the polymorphism pattern thereof associated with a "given property" for a plurality of individual organisms are recorded.

In step R-19 (SR-19), the donor DB is searched in accordance with processing program 13 based on the polymorphism address and the polymorphism pattern thereof that were read out in step R-17, and a "Gno." (information for discriminating an individual organism) having a combination of the polymorphism address and the polymorphism pattern matching with the combination of the polymorphism address and the polymorphism pattern thereof, which were read out in step R-17, is extracted. More specifically, in the case of FIG. 35, when searching for a "Gno." having combination in which "1000" is "G" and "2000" is "C" and a "Gno." having combination in which "1000" is "A" and "2000" is "T," "Gno." 0003 and "Gno." 0004 can be extracted. The extracted "Gno." is information associated with semantic information, that was induced from semantic information.

In step R-20 (SR-20), the extracted "Gno." is transmitted to personal computer 3. At this time, the "Gno." and other information may be transmitted to personal computer 3 within the range regulated by the IC made by the donor registrant. Examples of other information include information that was recorded when constructing the donor DB shown in FIG. 35, for example, additional information recorded in data III, data IV, and data V on genome-related information recording medium 24. More specifically, in the case of FIG. 35, "Gno." 0003 and "Gno." 0004 are transmitted to personal computer 3.

In step R-21 (SR-21), personal computer 3 receives the "Gno." and other information transmitted from shared computer 2. In step R-22 (SR-22), the received "Gno." and other information are output, thereby obtaining information on other individual organisms having properties compatible with the "given property." That is, the recipient can obtain information on other individual organisms which is compatible with respect to the recipient's "given property." In the case of FIG. 35, the recipient can obtain information associated with semantic information, i.e., that other individual organisms which are compatible with respect to the "given property" are "Gno." 0003 and "Gno." 0004. In step R-20, the results of extraction may be simultaneously transmitted to an other organization providing objects or services to the requester using the result of extraction.

Figure 36:
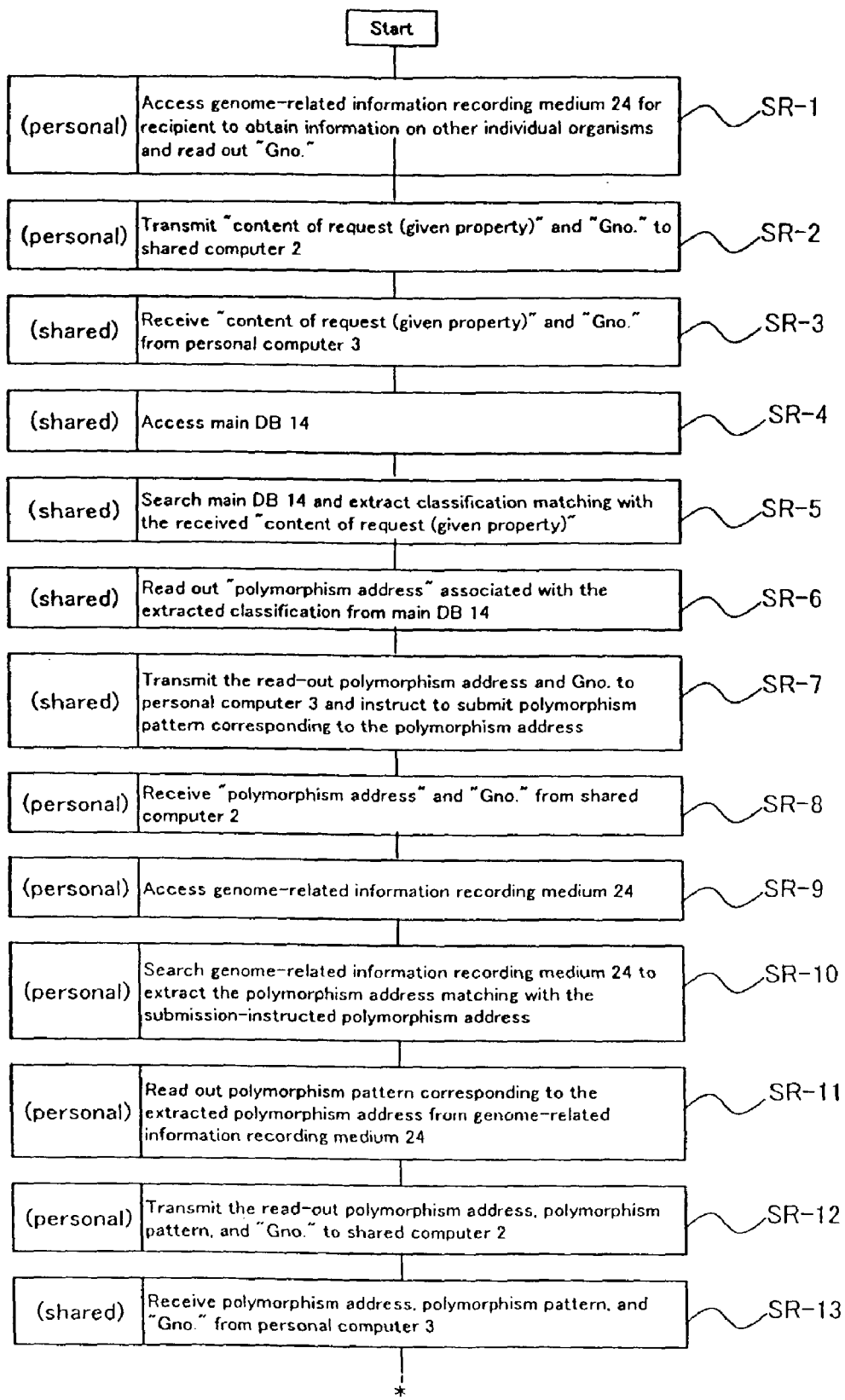
FIG. 36 is a flow chart showing processing in a shared computer and a personal computer in a system for providing information on other individual organisms having properties compatible with a "given property" of the requestor.
Figure 37:
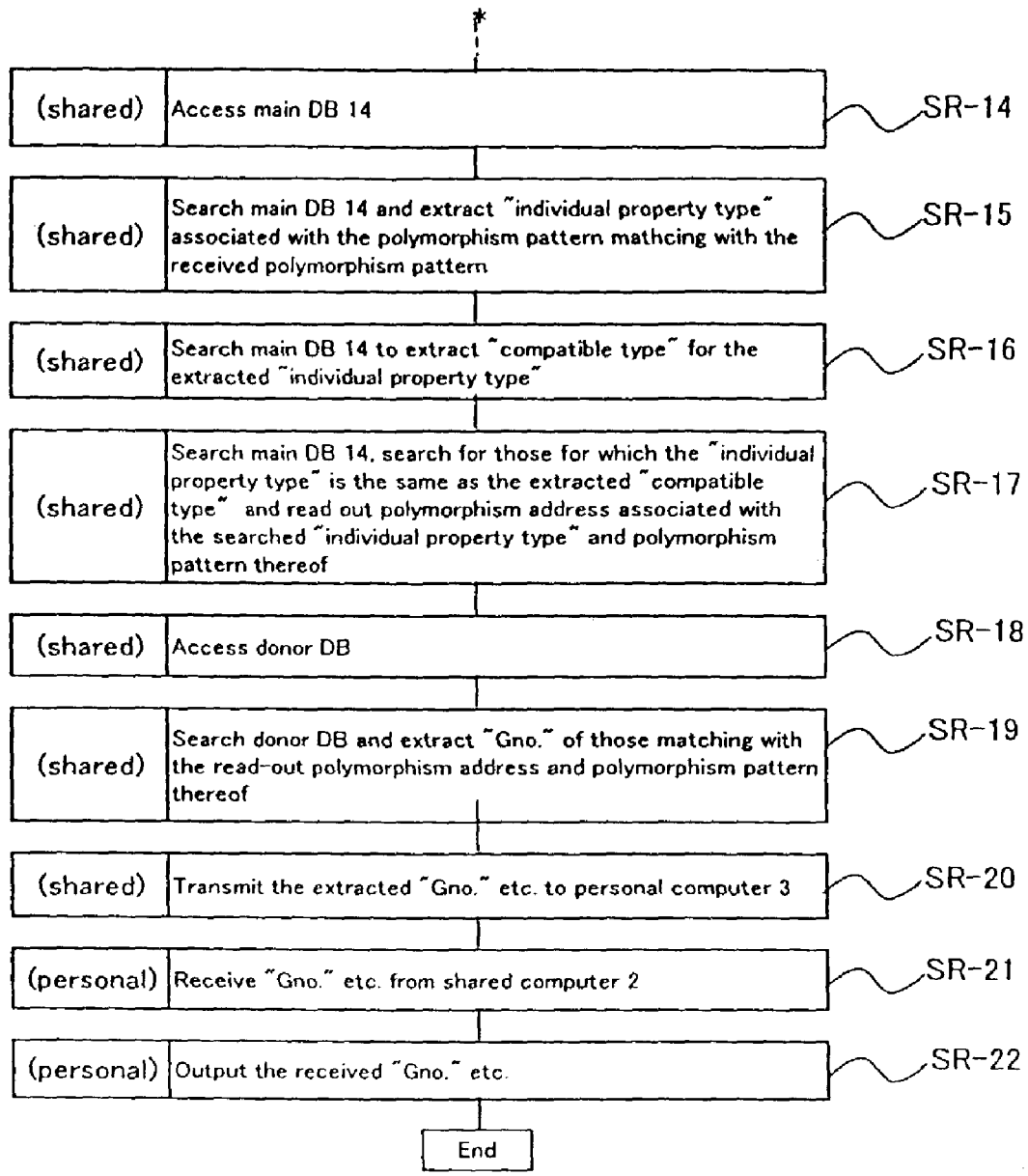
FIG. 37 is a flow chart, which is a continuation of FIG. 36, showing processing in a shared computer and a personal computer in a system for providing information on other individual organisms having properties compatible with a "given property" of the requestor.

As described above, information on an other individual organism which has a property compatible with the recipient's "given property" for a predetermined purpose can be obtained in accordance with the flow charts shown in FIGS. 36 and 37 according to the system. More particularly, in this case, all of genome-related information 28 recorded on genome-related information recording medium 24 is not necessarily output through communication network 1, and instead, only the part of genome-related information 28 for which submission has been instructed may be output. According to the system, therefore, leakage of highly confidential polymorphism addresses and polymorphism patterns peculiar to the individuals can be prevented. Also in the system, use of the "anonymous polymorphism address" can further prevent leakage of the polymorphism addresses and polymorphism patterns.

In the system, since a classification such as "given property" and "compatible type," which is compatible with the individual property type, are corrected and increases in the number of its type, a more accurate and wider range of information is included through updating of main DB 14. In addition, if many individual organisms are registered as donors in accordance with the flow charts shown in FIG. 34, a large amount of donor information is accumulated in the donor DB. According to the system, updating of main DB 14 in compliance with such increase, correction and the like of information and increase in the amount of information in the donor DB enable the recipient to utilize the newest information.

Furthermore, according to the system, a third party or third organization can easily monitor and control shared computer 2 by examining main DB 14 and donor DB. Accordingly, as the system can, for example, execute administrative control over the provider of information on other individual organisms, adequate and ethical control over the provider of information on other individual organisms can be executed.

When the donor DB has semantic information implied by the polymorphism pattern recorded therein, shared computer 2 searches main DB 14 based on, for example, the polymorphism pattern and the Gno. received in step R-13 (SR-13) to extract the "individual property type" and the "compatible type" of the recipient (step R-15). Shared computer 2 searches the "individual property type" of other individual organisms recorded in the donor DB based on the "individual property type" and "compatible type" of the recipient without conducting steps R-16 to R-19, and extracts other individual organisms having the "individual property type" that matches with the recipient's "compatible type." Subsequently, conducting steps R-20 to R-22, the recipient can obtain information on other individual organisms that are compatible with the recipient regarding the "given property." In this case, in step R-20, the results of extraction may be simultaneously transmitted to another organization for providing objects or services to the requester using the results of extraction.

Further in the system, a donor registrant utilizing the system for donor registration can obtain information on other individual organisms as a recipient. In this case, donor registration is carried out through steps D-1 to D-14 shown in FIG. 34 and then advanced to step R-14, and information on other individual organisms can be obtained for the "given property" in the same manner as described. In this case, the user performs donor registration for a "given property" and at the same time can obtain information on other individual organisms for the "given property." When an individual organism which has conducted donor registration afterwards becomes a recipient, shared computer 2 accesses the donor DB after steps R-1 and R-2 and the "polymorphism address" matching with the "Gno." of the recipient and the "polymorphism pattern" thereof are read out, and the process then advances to step R-14. Information on other individual organisms for the "given property" can be obtained in the same manner as described. Also in this case, the user performs donor registration for a "given property" and at the same time can obtain information on other individual organisms for the "given property."

As described above, according to the system, on genome-related information recording medium 24 and in main DB 14, standardization of only "polymorphism addresses" and the "polymorphism patterns" thereof eliminates the need for standardization of other specific data. Thus, the system can be utilized in a wide range of industries. That is, when providing information using genome-related information recording medium 24, the provider of objects or services can provide information in various manners without the need to standardize semantic information to correspond to the polymorphism pattern or a unified standard such as a method for transmitting/receiving data.

In the above fourth embodiment, the system for processing information for obtaining information on other individual organisms having a "compatible type" compatible with an "individual property type," as the "individual property type," was explained. The system for processing information, however, is not limited to such embodiment. For example, the system may be directed to obtaining information on other individual organisms having a "compatible type" that is incompatible with an "individual property type" as the "individual property type." In this case, an "individual property type" implied by a predetermined "polymorphism pattern" (information on a predetermined individual organism) and an "incompatible type" (information on an other individual organism) indicating a type incompatible with the "individual property type" are recorded as semantic information in main DB 14.

EFFECT OF THE INVENTION

As is apparent from the foregoing detailed description, a system for processing information can be constructed according to the present invention in which differences in information on nucleotide sequences among individual organisms are effectively utilized in order to provide semantic information and/or information associated with the semantic information that is useful for each individual. More particularly, the present invention enables use of the newest semantic information through updating, correction or the like of semantic information. Therefore, the present invention can provide high-quality objects and/or services relating to request information.

What is claimed is:

1. An apparatus for processing information on a nucleotide sequence, in which the apparatus is configured to access a database storing positional information representing a position in the nucleotide sequence, polymorphism information, and semantic information, comprising:

a transmitter/receiver that is configured to receive request information from a request computer, via a communication network, corresponding to an object or service, and wherein the request information does not include genome-related information; and a CPU that is configured to:
search the database for positional information corresponding to the received request information, and retrieve the positional information;
cause the transmitter/receiver to transmit, via the communication network, the retrieved positional information, which corresponds to the received request information, to a computer which is configured to access a recording medium storing polymorphism information regarding an individual;
obtain polymorphism information based on the transmitted positional information, received by the transmitter/receiver via communication network;
search the database for semantic information or search for information corresponding to the semantic information that is stored in the database or another database based on the received polymorphism information, and retrieve the semantic information or information corresponding to the semantic information; and
output the semantic information or information corresponding to the retrieved semantic information to the request computer or a device that utilizes the semantic information or information corresponding to the semantic information to comply with a request substantially included in the request information.

2. The apparatus for processing information on a nucleotide sequence according to claim 1, wherein the CPU is configured to set secondary positional information corresponding to the retrieved positional information, the transmitter/receiver is configured to transmit the retrieved positional information along with the secondary positional information, and the CPU, followed by the received polymorphism information along with the secondary positional information, is configured to retrieve semantic information or information corresponding to the semantic information based on the received polymorphism information and the received secondary positional information.

3. The apparatus for processing information on a nucleotide sequence according to claim 1, wherein the at least one of the databases further stores a level of disclosure corresponding to the semantic information, said level of disclosure determining whether output of the semantic information or the information corresponding to the semantic information is approved or not.

4. The apparatus for processing information on a nucleotide sequence according to claim 1, wherein the CPU is configured to retrieve a plurality of pieces of positional information corresponding to the request information, wherein the transmitter/receiver is configured to receive polymorphism information corresponding to each of the plurality of pieces of the retrieved positional information; and wherein the CPU is configured to retrieve semantic information or information corresponding to the semantic information based on the received plurality of pieces of polymorphism information.

5. The apparatus according to claim 1, wherein the CPU is configured to cause the transmitter/receiver to transmit the retrieved positional information, which corresponds to the received request information, to the request computer.

* * * * *